(12) United States Patent
Hall et al.

(10) Patent No.: US 11,395,474 B2
(45) Date of Patent: Jul. 26, 2022

(54) HARVESTING AND INCUBATING SYSTEMS FOR CULTIVATION OF INSECTS

(71) Applicant: Aspire Food Group LTD, Toronto (CA)

(72) Inventors: Michael Todd Hall, Austin, TX (US); Gabriel Mott, Austin, TX (US); Mohammed Ashour, Austin, TX (US)

(73) Assignee: ASPIRE FOOD GROUP LTD, Toronto (CA)

( * ) Notice: Subject to any disclaimer, the term of this patent is extended or adjusted under 35 U.S.C. 154(b) by 225 days.

(21) Appl. No.: 16/551,074

(22) Filed: Aug. 26, 2019

(65) Prior Publication Data

US 2019/0387704 A1 Dec. 26, 2019

Related U.S. Application Data

(63) Continuation of application No. 15/591,699, filed on May 10, 2017, now abandoned.

(60) Provisional application No. 62/334,022, filed on May 10, 2016.

(51) Int. Cl.
 *A01K 67/033* (2006.01)
 *A01K 1/01* (2006.01)
 *B07B 1/04* (2006.01)
 *B65G 47/248* (2006.01)

(52) U.S. Cl.
 CPC .............. *A01K 1/01* (2013.01); *A01K 67/033* (2013.01); *B07B 1/04* (2013.01); *B65G 47/248* (2013.01)

(58) Field of Classification Search
 USPC ................................................ 119/6.5, 6.6
 See application file for complete search history.

(56) References Cited

U.S. PATENT DOCUMENTS

| | | | | |
|---|---|---|---|---|
| 3,893,420 | A * | 7/1975 | Andreev | A01K 67/033 119/6.6 |
| 6,688,255 | B2 * | 2/2004 | Donaldson | A01K 67/033 119/6.5 |
| 8,733,284 | B2 * | 5/2014 | Courtright | A01K 67/033 119/6.6 |
| 10,362,772 | B2 * | 7/2019 | Arsiwalla | A01K 67/0332 |
| 10,772,309 | B2 * | 9/2020 | Sobecki | A01K 67/033 |
| 10,926,295 | B1 * | 2/2021 | Greeley | A01K 67/033 |
| 2011/0081452 | A1 | 4/2011 | Hem et al. | |
| 2012/0329135 | A1 | 12/2012 | Lopez-Cervantes | |
| 2013/0319334 | A1 | 12/2013 | Newton et al. | |
| 2016/0037808 | A1 | 2/2016 | Miller | |
| 2017/0042131 | A1 | 2/2017 | Unger | |

(Continued)

FOREIGN PATENT DOCUMENTS

BR 102015028820 A 5/2017
CN 106279727 A 1/2007

(Continued)

*Primary Examiner* — David J Parsley
(74) *Attorney, Agent, or Firm* — Lee & Hayes, P.C.

(57) ABSTRACT

A system for harvesting insects from a habitat. The system configured to separate waste, live insects, and dead insects in a manner that the live insects may undergo a first processing procedure and the dead insects may undergo a second processing procedures. For example, the first processing procedure may include processing the insects for human consumption and the second processing procedure may include processing the dead insects for minerals or materials.

20 Claims, 45 Drawing Sheets

(56) References Cited

U.S. PATENT DOCUMENTS

| | | |
|---|---|---|
| 2017/0202193 A1 | 7/2017 | Ogose et al. |
| 2017/0251700 A1 | 9/2017 | Doane et al. |

FOREIGN PATENT DOCUMENTS

| | | |
|---|---|---|
| CN | 206078668 U | 4/2007 |
| CN | 104756956 A | 7/2015 |
| CN | 104770326 A | 7/2015 |
| CN | 106269811 A | 1/2017 |
| CN | 106305632 A | 1/2017 |
| CN | 106359306 A | 2/2017 |
| CN | 106359311 A | 2/2017 |
| CN | 106508823 A | 3/2017 |
| CN | 106509504 A | 3/2017 |
| CN | 206043148 U | 3/2017 |
| CN | 206062034 U | 4/2017 |
| CN | 206101346 U | 4/2017 |
| CN | 106614400 A | 5/2017 |
| CN | 106719453 A | 5/2017 |
| CN | 106733666 A | 5/2017 |
| CN | 106902958 A | 6/2017 |
| CN | 106942163 A | 7/2017 |
| CN | 106942164 A | 7/2017 |
| CN | 206334847 U | 7/2017 |
| CN | 206334868 U | 7/2017 |
| CN | 206354225 U | 7/2017 |
| CN | 206423511 U | 8/2017 |
| CN | 206442964 U | 8/2017 |
| CN | 107114325 A | 9/2017 |
| CN | 107136025 A | 9/2017 |
| DE | 102016115189 B3 | 8/2017 |
| KR | 101691584 B | 1/2017 |
| KR | 101695548 B | 1/2017 |
| KR | 101716763 B | 3/2017 |
| KR | 101716766 B | 3/2017 |
| KR | 20170030402 A | 3/2017 |
| KR | 101741999 B | 5/2017 |
| KR | 20170058564 A | 5/2017 |
| KR | 101747927 B | 6/2017 |
| KR | 101747928 B | 6/2017 |
| KR | 20170068752 A | 6/2017 |
| KR | 101755167 B | 7/2017 |
| KR | 20170080988 A | 7/2017 |
| KR | 20170085337 A | 7/2017 |
| PL | 413266 A | 1/2017 |
| PL | 413267 A | 1/2017 |
| RU | 2615636 C | 4/2017 |
| WO | WO16153338 A1 | 9/2016 |
| WO | WO16153339 A1 | 9/2016 |
| WO | WO16166465 A1 | 10/2016 |
| WO | WO16166471 A1 | 10/2016 |
| WO | WO17007309 A1 | 1/2017 |
| WO | WO17007310 A1 | 1/2017 |

\* cited by examiner

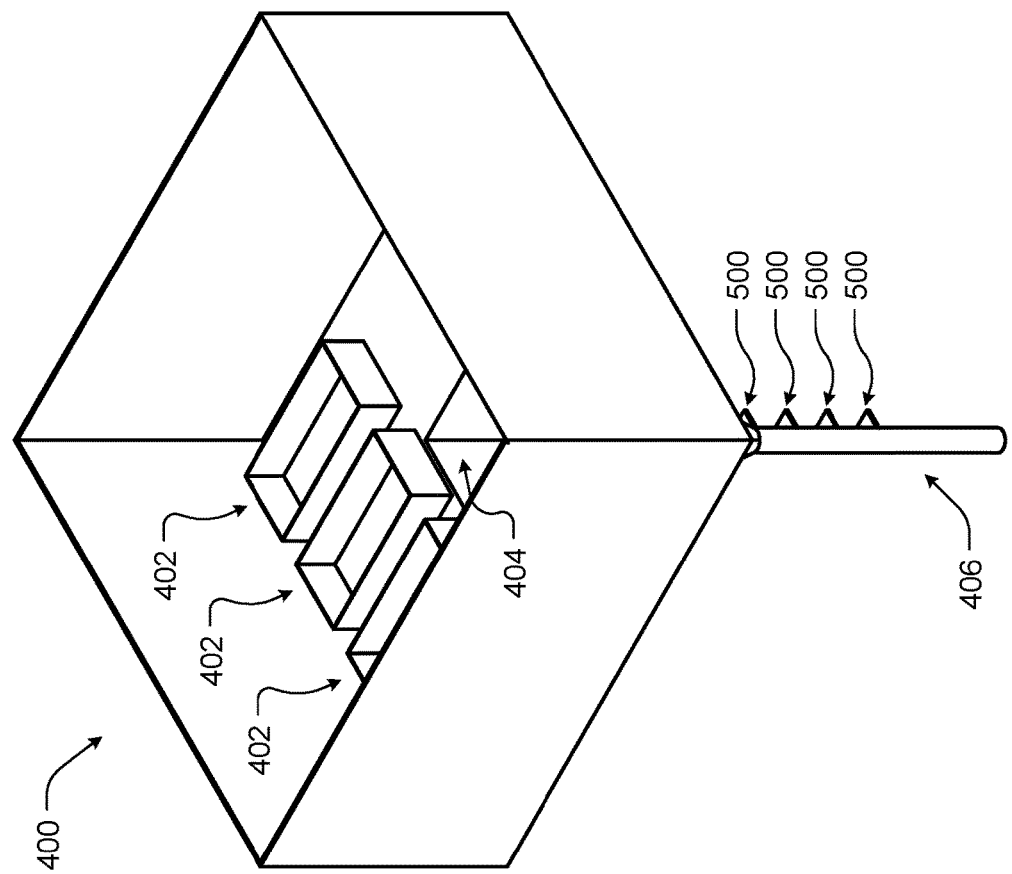
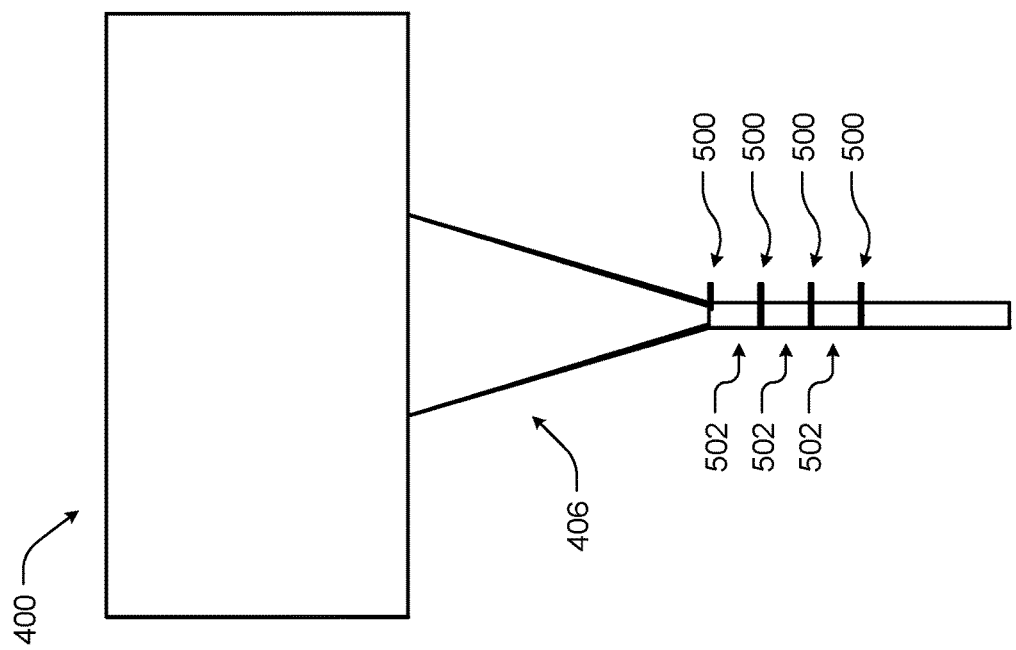
FIG. 5

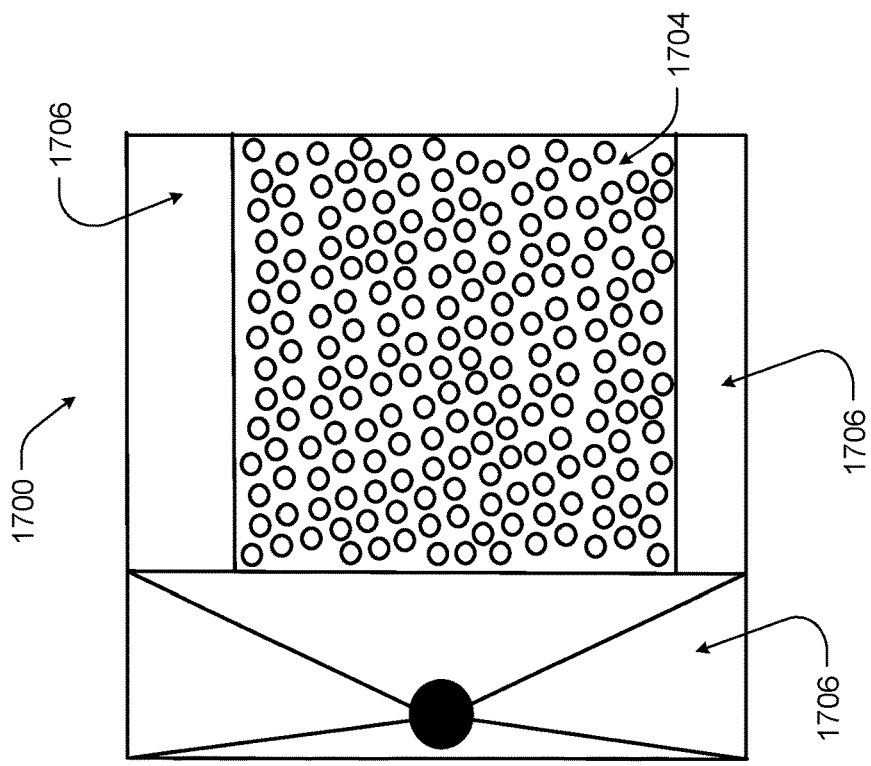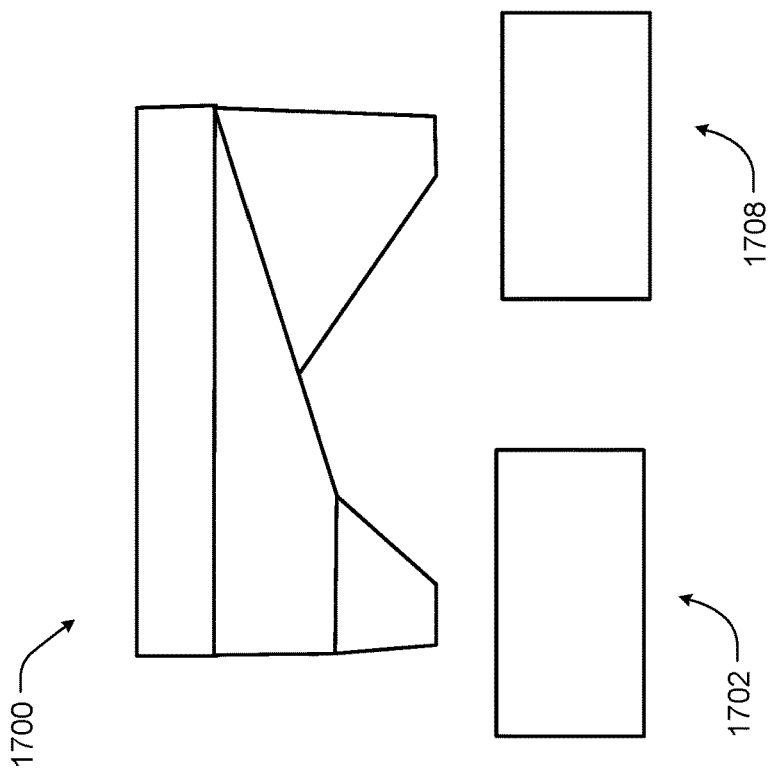
FIG. 18

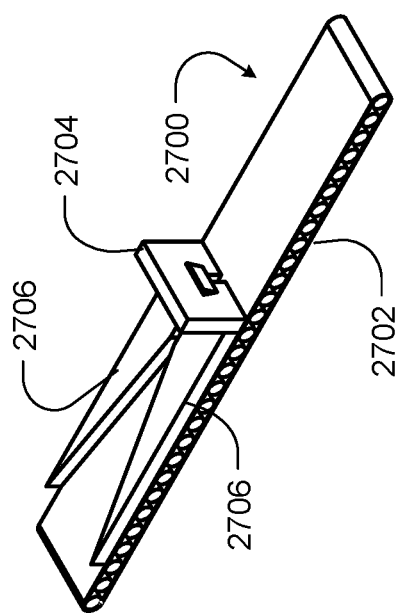
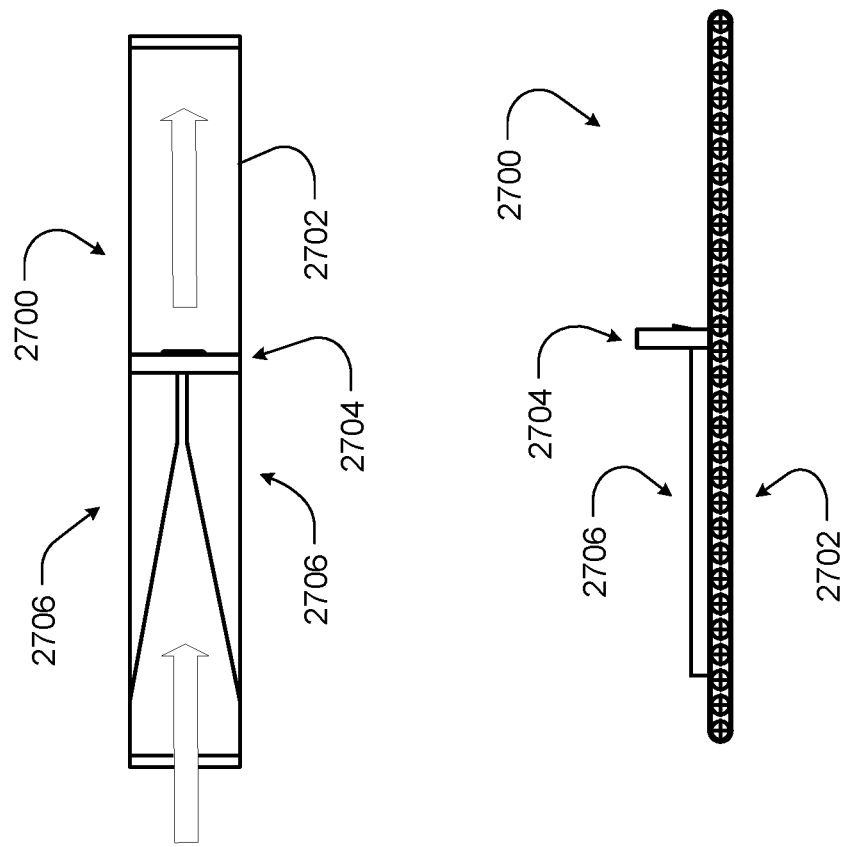
FIG. 27

HARVESTING AND INCUBATING SYSTEMS FOR CULTIVATION OF INSECTS

CROSS REFERENCE TO RELATED APPLICATIONS

This application is a continuation of and claims priority to U.S. application Ser. No. 15/591,699 to Hall et al., entitled "Harvesting and Incubating Systems for Cultivation of Insects," filed May 10, 2017 which claims priority to U.S. Provisional Application No. 62/334,022 to Hall et al., entitled "Harvesting and Incubating Systems for Cultivation of Insects," filed May 10, 2016, the entirety of which are incorporated herein by reference thereto.

BACKGROUND

Today most insects that are cultivated for human consumption are housed in single use cardboard boxes, plastic bins, or immobile large troughs made of wood or concrete. Cardboard boxes are disposed of manually after each use and add significant expense to the cultivating and harvesting process. Additionally, the harvesting process typically includes shaking or dumping out the cardboard or plastic boxes and manually collecting or picking out the live insects. This is a time consuming and labor intensive activity that is further subject to human error and may result in substantial economic loss and wastage.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 5 illustrates another view of the separation enclosure of FIG. 4 according to some implementations.

FIG. 18 illustrates the example system of FIG. 17 for use in the waste separation area of FIG. 1 according to some implementations.

FIG. 27 illustrates another example system for use in the processing area according to some implementations.

DETAILED DESCRIPTION

Figure 1:
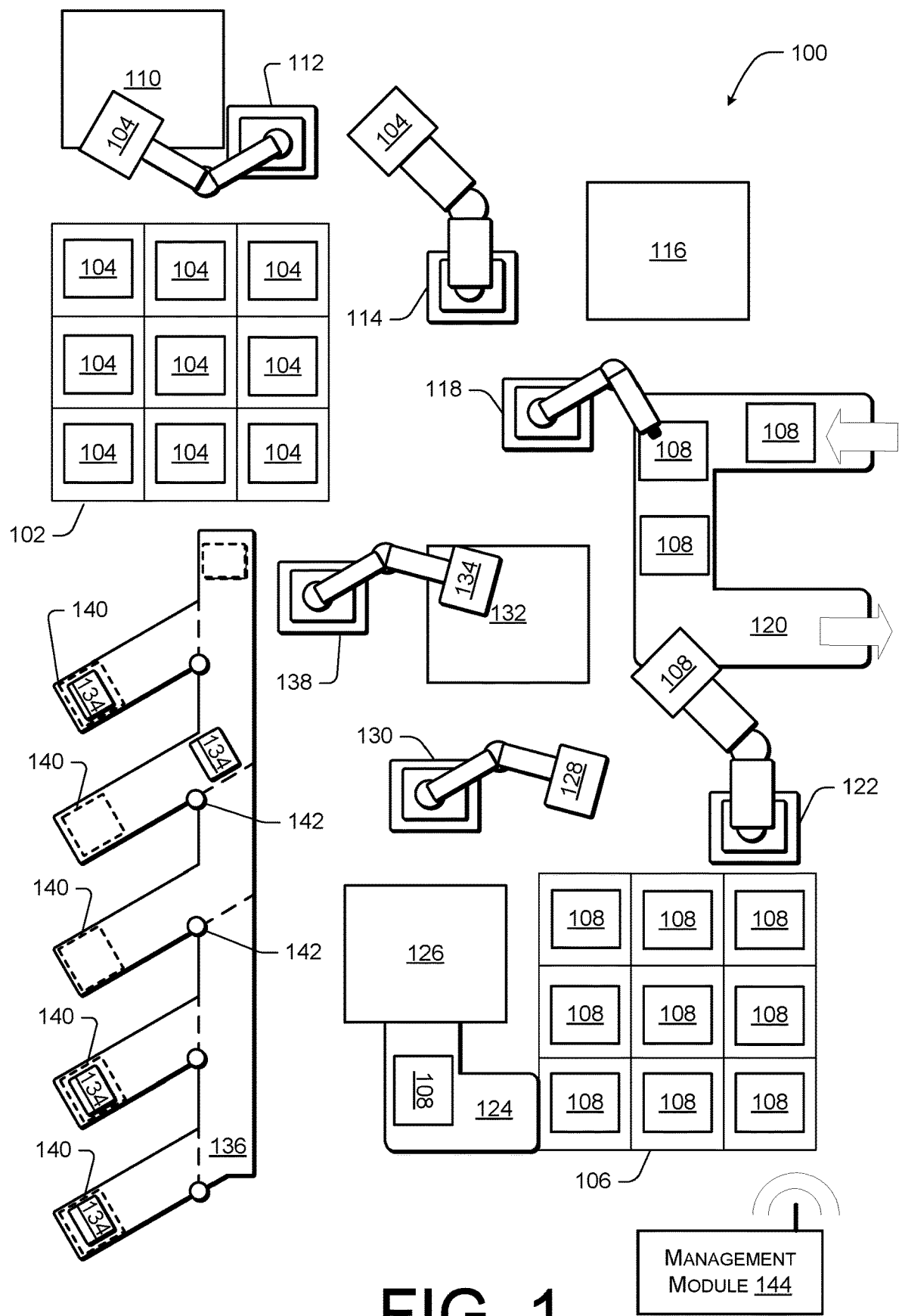
FIG. 1 illustrates an example system for cultivating and harvesting insects according to some implementations.

Described herein are implementations and techniques for providing an automated systems for sorting, incubating, and harvesting insects. For example, the system may include apparatuses to separate live insects from dead insects or other waste. In other examples, the system may include apparatuses for counting and isolating eggs or insect larva for placement in growing or cultivating habitats. In still other examples, the system may include apparatuses for separating the insects into parts for further processing such as the production of flour, chitin, or various vitamins or minerals.

In general, the systems are designed to improve the efficiency of raising and harvesting live insects, such as crickets, grasshoppers, mealworms, and other insects that have a flightless stage, and to minimize the insect's exposure to human interaction or contact in addition to reducing exposure to invasive pathogens. In some implementations, the apparatuses may be configured to separate the egg or larvae insects from the medium in which the eggs or larvae are incubated in. Separation of the eggs from the medium is also useful for accurate measurement of eggs and tracking of population die off during cultivation. In some cases, a die off rate above a threshold may indicate a contaminated habitat that may need to be discarded or destroyed rather than harvested. The apparatus may also be configured to select or group eggs based on a desired population of adult insects within a habitat, in addition to reducing inbreeding depression for the purpose of improving multi-generational fitness. Overpopulating a habitat results in too many adult insects and leads to massive losses of product as the insects die off until a stable population is achieved.

A sieve apparatus may be utilized to separate the eggs or larvae from the medium in which the eggs are incubated. For instance, the medium may be a fine grain sand that may pass through openings that are too small for the eggs. Thus, a sieve including a screen or mesh may be provided to first separate the medium from the eggs. The eggs may then be collected from the screen. For instance, the screen or mesh portion of the sieve may retract or tilt to cause the eggs to roll or fall into a collection bin or container located separate from the bin or container used to collect the medium. In one particular case, the mesh or screen is a conveyor belt which may move the eggs into a collection container or to a second apparatus for sorting.

In another example, the medium may include a dissolvable foam. In this example, the eggs may be injected into the foam and incubated. When the eggs are ready to hatch, the eggs may be moved to a separating apparatus. In some cases, the separating apparatus may include a multi-chambered stack. The egg-filled foam may be moved over the multi-chambered stack via, for example, a conveyor belt and a first retractable panel may be opened to allow the egg-filled foam to fall into a first chamber of the multi-chambered stack. The first chamber may be filled with a solvent that is safe for the eggs, such as water, other liquids, a gas, or a gaseous mixture, among others. In other instances, the first chamber may be equipped with light sources tuned to produce a specific wavelengths of light that will cause the foam to dissolve. In yet other instances, the first chamber may be configured to vibrate or apply mechanical motion to the foam in a way to break up or dissolve the foam. The first chamber may then be drained leaving the eggs behind.

Once the foam is removed, a second retractable panel may be opened to allow the eggs to fall into a second chamber of the multi-chambered stack. The second chamber may include a scale or weighing device to allow the eggs to be counted prior to separation and placement in habitats. Alternatively, the second chamber may be a collection area in which the eggs may be stored prior to counting, separation, and placement in habitats. In one example, the second chamber may include a retractable floor or other type of opening. The opening may be connected to a tube or cone having a gradually reducing size. Sensors may be placed within the tube to count the eggs as the eggs slide past. The end of the tube may include multiple storage compartments. Each of the storage compartments may receive a desired number of eggs based on a size of a habitat allocated to cultivate the adult insects. Once full, the storage compartment may be closed and the next compartment may be filled.

In one specific example, the storage compartments may be removable and a mechanical arm or other conveyor may move each of the storage compartments into a habitat, release or open the storage compartment, and deposit the eggs into a second medium within the habitat where the eggs will ultimately hatch and the adult insects will be cultivated.

In some implementations, rather than counting and separating eggs from the medium in which the eggs are laid, the egg laying process may be controlled to result in a particular egg to medium density or an egg to adult habitat ratio. For example, a breeding enclosure may be equipped with environmental controls and or sensors. For example, the environmental controls may be used to stimulate or sedate the breeding insects to increase or decrease the number of eggs being laid within the breeding enclosure. In one example, the density of eggs laid per unit of volume of breeding insects (or egg laying females) given particular environmental settings (e.g., temperature, moisture, humidity, wind, light, etc.) may be known. Thus, the environmental controls within the breeding enclosure may be set to encourage a particular egg density.

The sensors may include image sensors, thermal sensors, weight sensors, etc. that may track groups of insects or individual insects. For instance, a thermal sensor may be utilized to distinguish egg bearing females from other insects and the image sensors may be used to track or identify each egg laying event, such that a number of egg bearing females or eggs may be determined within the breeding enclosure. Alternatively, the image data may be used to distinguish male from female insects (e.g., based on features such as size, color, movement pattern, activity, etc.), determine female egg laying viability (e.g., based on size and other distinguishable features) track the female insects, and identify egg laying events. The environmental controls may then activate based upon an analysis of the sensor data to control the number of eggs laid within the breeding enclosure. Once a desired amount of eggs are achieved the breeding insects and/or the egg laying medium may be removed.

In another example, an amount of medium having a known weight may be placed in a breeding enclosure for a period of time. In some cases, the period of time may be selected to achieve a desired egg density (for example, using the environmental controls and sensor data described above). The egg bearing medium may then be removed and weighed. Using an average weight per egg and the known weight of the medium, the number of eggs may be determined. The medium may be divided and placed into individual habitats to achieve a desired adult insect population. In some cases, medium from multiple breeding enclosures may be combined and mixed to achieve an approximate medium to egg density ratio. The mixed medium is then divided and placed into the habitats in amounts selected to achieve the desired adult insect populations.

In some instances, rather than sorting eggs and/or egg bearing medium into the adult habitats, newly hatched insects may be herded, counted, separated, and placed in the habitats. In this manner, the number of live insects per habitat is more easily achieved as a number of the eggs typically fail to hatch or do not produce viable offspring. Thus, by introducing live insects into the habitats the desired population may be more accurately achieved. Unfortunately, the newly hatched insects are easily crushed when handled. Thus, some implementations described herein include apparatus for herding the newly hatched insects into adult habitats. For instance, in one example, egg bearing media or boxes filled with the egg bearing medium may be placed within a separation enclosure. The separation enclosure may include an opening connected to a funnel or cone having a gradually reducing size.

As the newly hatched insects move around the separation enclosure, each viable newly hatched insects eventually enters the opening and is processed via the funnel. Thus, the viable newly hatched insects separate themselves from the non-viable newly hatched insects. Sensors may be placed within the funnel to count the newly hatched insects as the newly hatched insects move past. The end of the funnel may include multiple storage compartments. Each of the storage compartments may receive a desired number of newly hatched insects based on a size of a habitat allocated to cultivate the adult insects. Once full, the storage compartment may be closed and the next compartment may be filled. In one specific example, the storage compartments may be removable and a mechanical arm or other conveyor may move each of the storage compartments into a habitat and release or open the storage compartment to deposit the newly hatched insects into the habit.

In another examples, the egg bearing medium may be placed in a separation enclosure. The separation enclosure may include an air source, such as a vent, fan, propeller, or jet to apply directional air flow over the egg bearing medium. The air flow may cause newly hatched insects to be pushed, moved, or herded into a collection chute or funnel, as discussed above. In some cases, the air flow may blow the newly hatched insects that escape the medium (e.g., the newly hatched insects with enough viability to burrow out of the medium) down the chute for collection, counting, and separation.

In another implementation, the insects are separated from waste product. In some cases, the insects may be raised on a habitat insert that is removed from the habitat and may be shaken over an empty collection bin to dislodge the insects from the insert. In this manner, the waste remains in the habitat and the live insects are deposited into the collection bins for further processing. In general, the habitat inserts may include a grid or matrix of vertical walls that provide living space for the insects and increase the overall surface area of the habitat, thereby, increasing the overall population density of the habitat. In other cases, the inserts may include horizontal walls, sloping walls or angular walls depending on the type and developmental level of the insects. In some cases, the inserts may also include perforations to allow the insects to move between sections of the habitat.

In one example, when the habitats are ready to be harvested, the habitat may be moved or placed upon a conveyor (such as a belt or track) which may move the habitats past a robotic arm. The robotic arm may be configured to attach or secure to the habitat insert, remove the insert from the habitat, position the insert over a collection bin, and vibrate or actuate the insert to cause the insects to dislodge from the insert and deposit the insects within the collection bin. During the period at which the robotic arm is collecting the insects within the collection bin, the conveyor may cause the habitat to flip over or upside-down to cause the remaining waste within the habitat to be dumped or removed. In some cases, the conveyor may vibrate or actuate to cause the habitats to vibrate and further assist with the waste removal. The habitats may then be moved to a wash station which may remove any remaining waste prior to having an insert placed back within the habit. The habitat may be moved to a position within the system at which the newly hatched insects or eggs may then be placed and a new population of insects cultivated within.

In another example, the inserts may be configured to attach or secure to the habitat (such that the inserts may be removed for cleaning or remain within the habitat when the habitat is flipped over). In this example, rather than utilizing a robotic arm to remove the insert and place the insects into a collection bin, a vacuum may be configured to run either the width or length (it can also be smaller and moved similar to a computer numerical control (CNC) mill) of the habitat. The habitat, including the insert, may be passed under the vacuum (or alternatively, the vacuum is moved over a stationary habitat). The vacuum may be configured to suction out the insects located on the walls of the habitat as the habitat moves under the vacuum. The suction level of the vacuum may be configured based on a depth of the habitat such that material within the bottom 1%, 5%, 10% or 15% remains in the habitat while material within the top portion of the habitat is removed. Thus, the waste deposited at the bottom of the habitat while the insects grow within the habitat remains within the habitat and the insects located on the walls of the inserts are removed. The vacuum system may include a tube connected to one or more collection bins for depositing the insects within the collection bins for further processing. Additionally, the insects have a lower density than the waste product the insects create and, thus, are removed from the habitat via a lower suction level than the waste product.

In one specific example, the vacuum or the habitats may include a sensor system that allows the system to determine the level of waste within the habitat and to adjust the suction of the vacuum to substantially optimize the removal of live insects while preventing waste from being deposited into the collection bins. In some cases, the vacuum may be sized to seal with the habitat. The vacuum system may be configured with a gas applicator to inject a gas (such as carbon dioxide $CO_2$ or freezing air) into the sealed habitats to kill the insects prior to removing via the vacuum. In some cases, the vacuum may make several passes with respect to the habitat to ensure that substantially all of the live insects are removed. For example, the vacuum and/or the habitat may include a motion sensor (or an image sensor, thermal sensor, other imaging device, or other sensor) able to detect the movement of the insects. The vacuum may make additional passes with respect to the habitat until a level of motion determined based on the data collected by the motion sensor indicates the motion is below a motion threshold.

In another example, because only insects alive at the time of harvesting are desirable for some uses (such as using the insects for human consumption). In these uses, various compounds may be added into the insect foods. For instance, the food may include fluoresce additives or dyes to improve the ability to track the movement of the live insects within the habit, ferrous material such that a magnet may be used to remove the insects in lieu of the vacuum.

In some specific examples, the habitat inserts may be configured to provide an electric charge which attracts and holds the insects to the insert walls prior to removal by the robotic arm or vacuum system. In another example, the walls of the inserts may be configured to release a chemical compound to attract the insects to the walls or a chemical additive that causes the insects to stick or adhere to the walls during a period of time prior to and during removal of the inserts. For instance, the walls of the inserts may include pores that allow chemicals stored or injected into the walls to seep out during the removal process.

In some implementations, rather than removing insects from the habitat the insects may be encouraged or herded into the collection bins. For example, the contents of the habitat may be dumped or deposited onto a mesh or screen that allows some material to pass but retains the live insects. The mesh or screen may be surrounded by or adjacent to a collection area, tube, or funnel that the live insects eventually move into. The live insects may then be transferred to the collection bin (e.g., by sliding down the tube having a low friction wall). After a period of time following the placement of the contents on to the mesh or screen, the screen may open and the remaining material may be deposited with the other waste. Thus, at least a portion of the live insects migrate into the collection tubes.

In some examples, an agitator, such as light, air, temperature, gas or sound, may be introduced via an environmental stimulus device to the insects to cause the insects to move in a particular direction away from the environmental stimulus device towards the collection area. For example, a strobe light may be utilized to cause the insects to move in the opposite direction from the source. In some cases, the screen or floor the insects are placed on may vibrate in sections or irritate the insects to cause them to move toward the collection area. In another example, an attractor, such as pheromones or food, may be introduced via an attractor device at a location to cause the insects to move toward the attractor device and the collection area.

Once the insects are collected within bins, the insects may be placed into various harvesting apparatus to remove or separate, for example, the chitin, appendages, or exoskeleton from the remainder of the insects, such that the chitin, appendages, or exoskeleton may be processed to produce various supplements, such as B12, iron, calcium, omega-6, amino acids, tryptophan, combinations thereof, or others. The remainder of the insect (e.g., the abdomens) may then be processed to produce a flour that may be used for cooking.

In one implementation, a tumbler may be associated with one or more of the collection bins or the collection tubes/areas as described above. For example, a majority of the chitin is present in the limbs and head of the insects. Thus the tumbler may include an inner section with corrugated exterior portions (the size of the corrugation to allow the limbs portion to pass but not the bodies). The inner section may be configured to spin and as the insects spin the limbs and heads to become detached from the abdomens. The limbs may fall through the corrugation on the exterior portion. Thus, the tumbler may utilize a combination of gravity and centrifugal force to separate the limbs and heads of the insects from the abdomens of the insects. The limbs may then be removed from the tumbler. After tumbling, the remaining abdomens and heads may be released from the inner section into a powdering section. The powdering section may include an environmental stimulus that powderizes the abdomens as the tumbler spins. As the abdomens are softer than the heads, the heads remain intake during the powderization. The bottom of the tumbler may then open to a screen or mesh to allow the powder to be removed from the tumbler leaving behind the heads. The screen may then release to collect the heads. In this manner, the limbs, heads, and abdomens may be separated and processed into different components.

In another implementation, a vibration plate may be used to separate the limbs, heads, and abdomens of the insects. For example, the vibration plate may utilize a combination of friction and movement to separate the limbs and head from the abdomens. In one case, a conveyor or belt may move over a plurality of vibrating plates/sections that vibrate a different frequencies to cause the body parts to separate. The conveyor or belt may include a fine mesh that allows the limbs or appendages of the insects to pass through following separation. The heads and abdomens may be passed into a tumbler to powderize the abdomens as discussed above.

In another example, rather than using a tumbler, a centrifuge device may apply large centripetal forces to the insects. The centrifuge may also be lined with a screen or mesh that allows the limbs to pass and retains the abdomens and heads. In some cases, the large centripetal forces applied from the mesh onto the insects cause them to reduce in size based on the sizing of the mesh. In one example, the centripetal forces may be controlled such that different density and structurally rigid components of the insects are separated at different instances. Thus, the different components may be collected independently from one another. Similarly, some types of insects shed exoskeletons as the insects mature. The exoskeletons (or chitins) collect with the waste in the habitat. In some examples, the waste material may be placed in the centrifuge to remove the waste product leaving behind the chitinous material, which may be processed for various supplements and compounds as described above.

In yet another implementation, the limbs, head, and abdomens may be separated via alignment slicing. Alignment slicing is the process of translationally and rotationally adjusting insects such that each insect shares an orientation. Once the specific orientation is achieved, the insects can be separated mechanically via cutting and/or slicing. In one example, the insect moves across a conveyor. As the insect moves translationally each insect impacts geometry (e.g., a wall with specific orientation) that forces the insect to orient to a specific direction. Once oriented, the insects are moved into a slicing/cutting device. The slicing/cutting device separates the insect into portions by slicing the limbs or appendages and head from the abdomens.

In another example, the insects or parts of insects may be processed chemically to separate the limbs, head, or abdomens. For example, the insects may be treated with specific chemicals, including plant-based oils, to separate limbs and appendages from the abdomens of an insect. In one example, the insects may be herded or passed through a chemical bath or spray via a conveying system. After the chemical treatment, the remaining portions of the insect may be separated by component using the system described above, such as a sieve system. Similarly, some types of insects shed exoskeletons as the insects mature. The exoskeletons (which consist of chitin) collect with the waste in the habitat. In some examples, the waste material may be treated with chemicals to dissolve the waste product leaving behind the chitinous material, which may be processed for various supplements and compounds as described above.

In some cases, oils may be removed from the insects or portions of the insects, such as the appendages, head, or abdomens. In these cases, the insects or portions of the insects may be pressed or compressed by a pressing machine. For example, the pressing machine may include a screw or twist based system that closes, exerts pressure on, or presses the insects placed within the press. As the insects are compressed, the oils are released and may be collected in the bottom of the pressing machine or escape into a collection area through opening in the bottom of the pressing machine. In some instances, the pressing machine may produce the oil and the insect remains may be processed to produce products that are relatively oil free when compared to similar insect based products.

FIG. 1 illustrates an example system 100 for cultivating and harvesting insects according to some implementations. In the illustrated example, the system 100 includes an incubation area 102 having multiple incubation enclosures 104 for incubating insect eggs and a cultivating area 106 including multiple habitats 108 for cultivating insects from infant stages to adulthood. In some implementations, the cultivating area 106 may include multiple areas for different developmental stages of the insect (such as newly hatched insects, child, adolescent, and adult) as each stage of development may require different environments to achieve substantially optimal environments.

Prior to placement in the incubation area 102, egg bearing females are stimulated to produce eggs in a controlled environment in an egg laying area 110. For instance, as described above, various environmental controls and tracking systems may be used to control the egg density per incubation enclosure 104. A first conveyor 112 may be used to move the incubation enclosure 104 into the incubation area 102 once the desired egg density is achieved.

Once the eggs within an incubation enclosure 104 are ready to hatch, the incubation enclosure 104 or the egg bearing medium may be moved by a second conveyor 114 to an egg or newly hatched insect collection area 116. For example, the egg or newly hatched insects collection area may include apparatus and systems for separating the medium from the egg and/or apparatus and systems for separating the newly hatched insects from the medium.

The eggs and/or newly hatched insects are counted and grouped to produce a desired population density within an insect habitat 106. For example, the eggs or newly hatched insects may be collected in tubes or vials that may be moved into a habitat 108 by a third conveyor 118. Each habitat 108 may then be moved to the cultivating area 106 via a fourth conveyor 120 and loaded onto a rack within the cultivating area 106 by a fifth conveyor 122.

Once the adult insects are ready to be harvested, a sixth conveyor 124 may move the habitats 108 to a waste separation area 126. At the waste separation area 126, the live insects may be separated from the waste product, exoskeletons, and other dead insects, as described above. The live insects may be gathered in a collection bin 128 and moved by a seventh conveyor 130 to a processing area 132. At the processing area 132, the insects may be sorted into various parts, as described above. For example, the limbs, heads, and abdomens may be separated.

Additional collection bins 134, each containing different parts of the insects (e.g., the limbs, heads, and abdomens) may be moved to a loading area 136 by an eighth conveyor 138. At the loading area 136, the collection bins 134 may be sorted into final collection areas 140 based on the contents of each collection bin 134. Each of the collection bins 134 may be guided to the correct collection area 140 by various gates, generally indicated by 142, which may open and shut to route the collection bins 134 to the desired collection area 140.

In some examples, the various conveyors and gates may be controlled by a management module 144 to coordinate the movement of the enclosures 104, habitats 108, collection bins 128 and 134 throughout the system 100.

In the illustrated example, various types of conveyors including robotic arms and conveyor belts are shown. However, it should be understood that any type of conveyor including robotic arms, free moving robots, tracks, conveyor belts, etc. may be used to move the various containers from one area to another. Additionally, in some cases, multiple conveyors may be combined such that a single conveyor may perform the operations of one or more of the conveyors in the illustrated example. For example, each of the conveyors may be replaced with a single mounted track system that allows the enclosures 104 and habitats 108 to move within the system 100.

Figure 2:
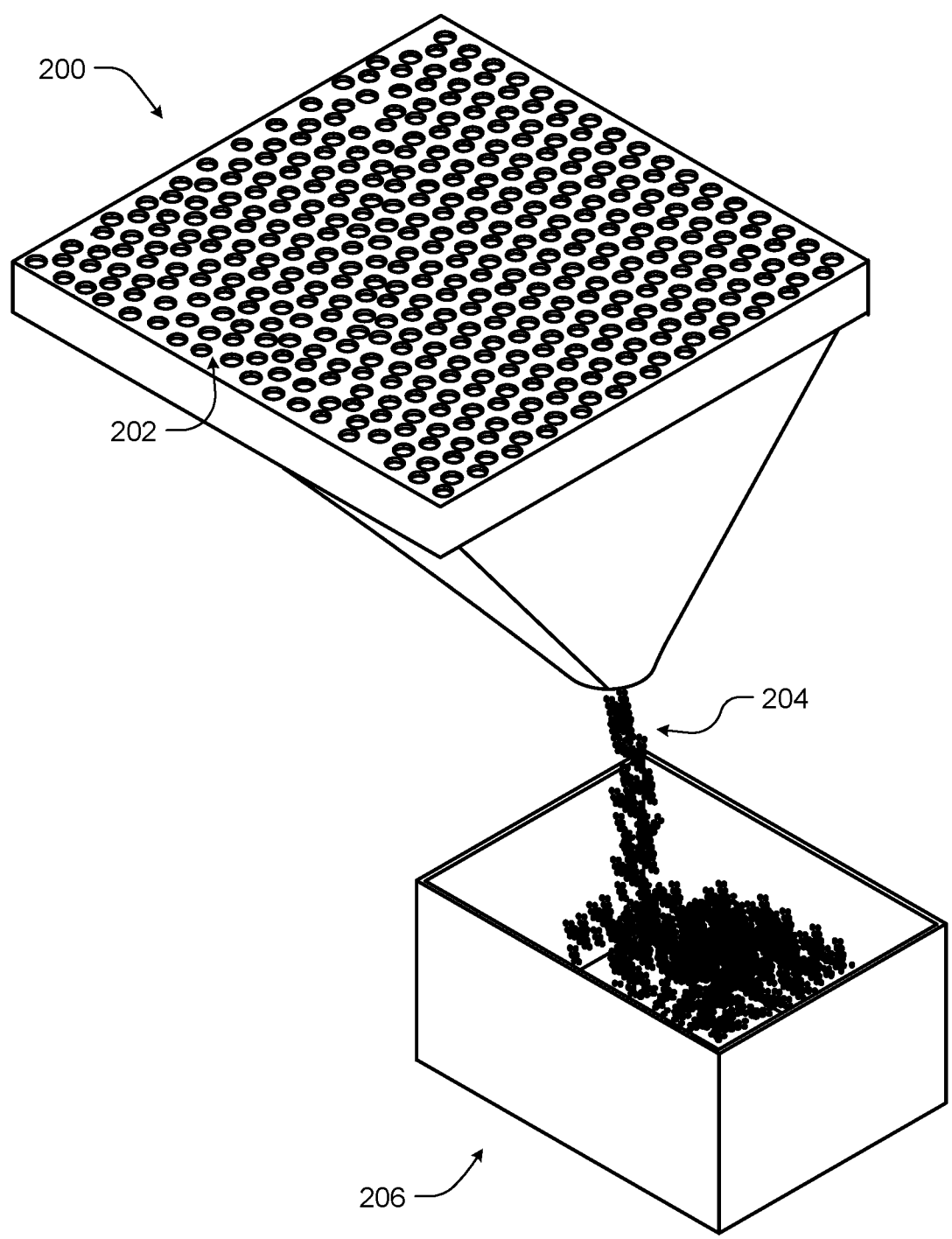
FIG. 2 illustrates an example device for use in the egg or newly hatched insect collection area of FIG. 1 according to some implementations.

FIG. 2 illustrates an example device 200 for use in an egg or newly hatched insect collection area 116 of FIG. 1 according to some implementations. In the illustrated example, the device 200 includes a mesh or screen 202 that the egg bearing medium 204 may be placed upon. The medium 204 may pass through the opening in the screen 202 to separate the eggs which remain on top of the screen 202 from the medium 204 which is deposited into a collection bin 206. In some cases, the screen 202 may separate to allow the eggs to fall into a second collection bin (not shown) after the medium 204 is removed.

Figure 3:
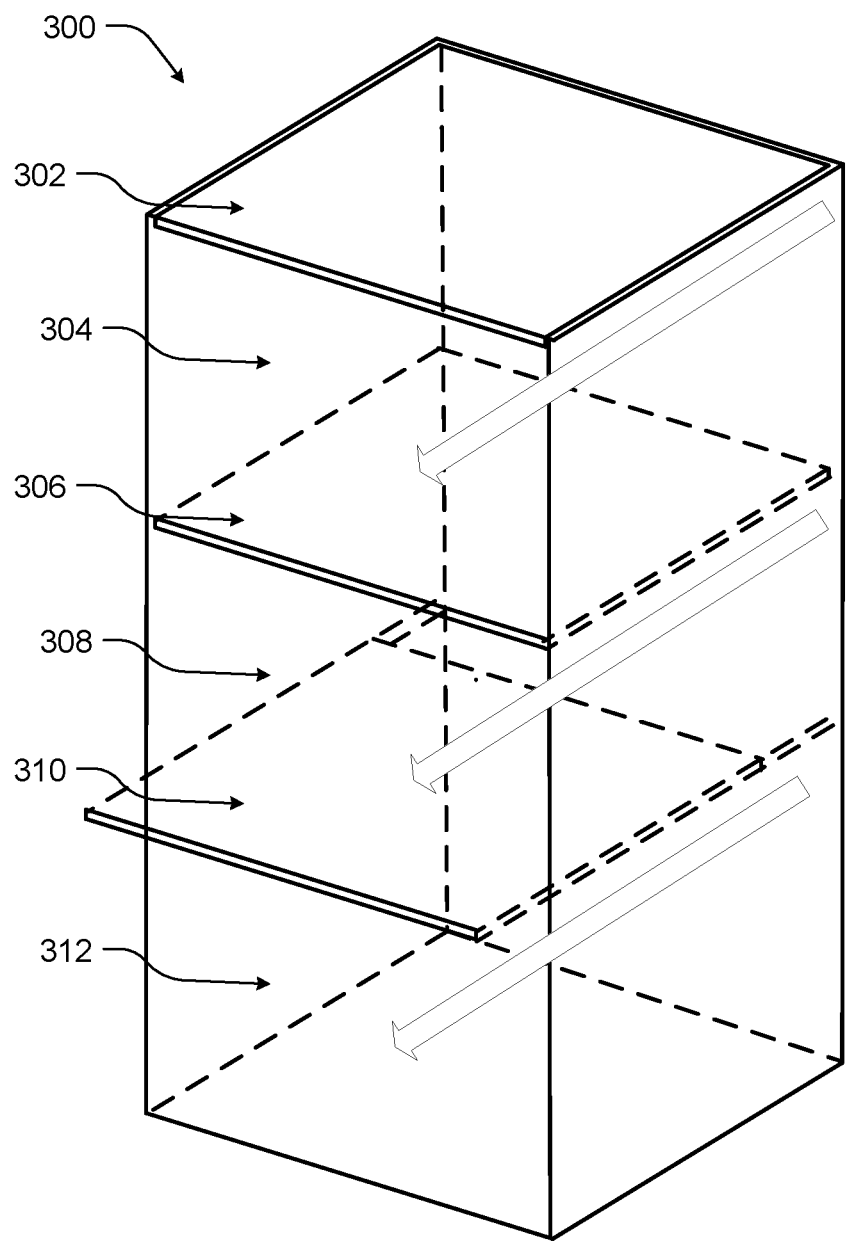
FIG. 3 illustrates another example device for use in an egg or newly hatched insect collection area of FIG. 1 according to some implementations.

FIG. 3 illustrates another example device for use in an egg or newly hatched insect collection area 116 of FIG. 1 according to some implementations. In the illustrated example, the medium may include a dissolvable foam. In this example, the eggs may be injected into the foam and incubated. When the eggs are ready to hatch, the eggs may be moved to a separating device. In some cases, the separating device may be a multi-chambered stack 300. The egg bearing foam may be moved over the multi-chambered stack 300 via, for example, a conveyor belt and a first retractable panel 302 may be opened to allow the egg bearing foam to fall into a first chamber 304 of the multi-chambered stack 300. The first chamber 304 may be filled with a solvent that is safe for the eggs, such as water, other liquids, a gas, or a gaseous mixture, among others. In other instances, the first chamber 304 may be equipped with lights sources tuned to produce a specific wavelengths of light that will cause the foam to dissolve. In yet other instances, the first chamber 304 may be configured to vibrate or apply mechanical motion to the foam in a way to break up or dissolve the foam. The first chamber 304 may then be drained leaving the eggs behind.

Once the foam is removed, a second retractable panel 306 may be opened to allow the eggs to fall into a second chamber 308 of the multi-chambered stack 300.

The second chamber may include a scale or weighing device to allow the eggs to be counted prior to separation and placement in habitats. Alternatively, the second chamber 308 may be a collection area in which the eggs may be stored prior to counting, separation, and placement in habitats. In the illustrated example, a third retractable panel 310 and third camber 312 may be included to allow for the placement of the separated eggs into a habitat.

Figure 4:
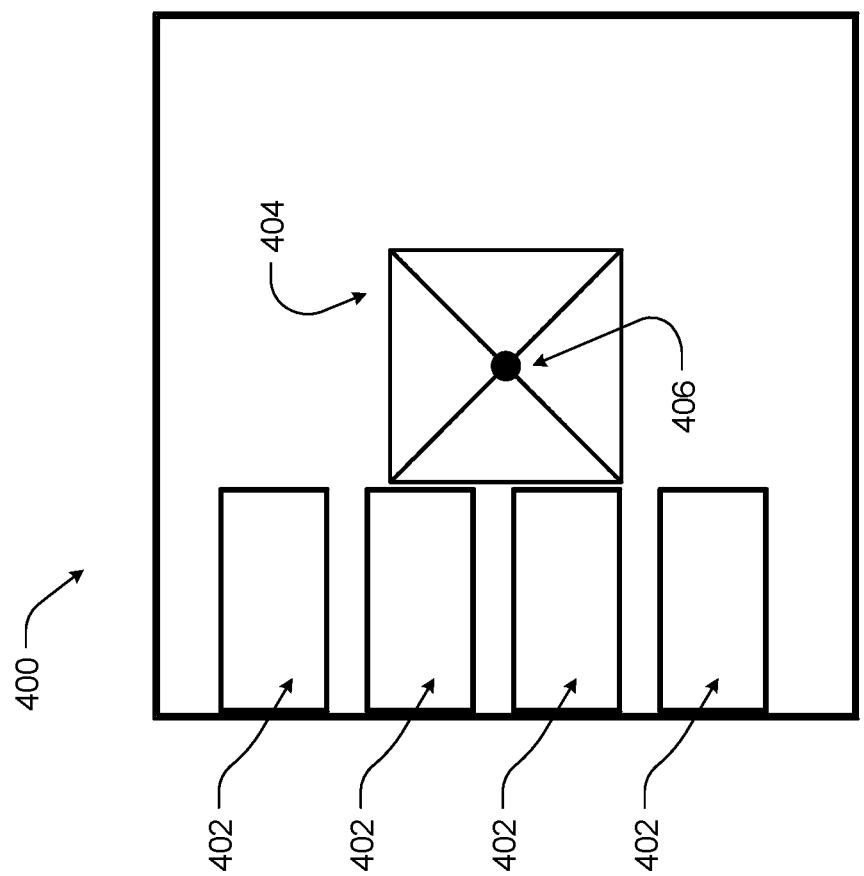
FIG. 4 illustrates an example device for use in the egg or newly hatched insect collection area of FIG. 1 according to some implementations.

FIG. 4 illustrates yet another example device for use in an egg or newly hatched insect collection area 116 of FIG. 1 according to some implementations. In the illustrated example, rather than sorting eggs and/or egg bearing medium as described above with respect to FIGS. 2 and 3, baby insects known as newly hatched insects may be herded, counted, separated, and placed in the habitats. In this manner, the number of live insects per habitat is more easily achieved as a number of the eggs typically fail to hatch or do not produce viable offspring. Thus, by introducing live insects into the habitats the desired population may be more accurately achieved.

For instance, in the current example, egg bearing medium or boxes 402 filled with the egg bearing medium may be placed within a separation enclosure 400. The separation enclosure 400 may include an opening 404 connected to a funnel or cone 406 having a gradually reducing size.

As the newly hatched insects move around the separation enclosure 400, each viable newly hatched insects eventually enters the opening 404 and is processed via the funnel 406. Thus, the viable newly hatched insects separate themselves from the non-viable newly hatched insects. Sensors may be placed within the funnel 406 to count the newly hatched insects as the newly hatched insects move past. The end of the funnel 406 may include multiple storage compartments. Each of the storage compartments may receive a desired number of newly hatched insects based on a size of a habitat allocated to cultivate the adult insects. Once full, the storage compartment may be closed and the next compartment may be filled.

FIG. 5 illustrates another view of the separation enclosure 400 of FIG. 4 according to some implementations. In the current example, egg bearing medium or boxes 402 filled with the egg bearing medium may be placed within a separation enclosure 400. The separation enclosure 400 may include an opening 404 connected to a funnel or cone 406 having a gradually reducing size. As discussed above, each viable newly hatched insects eventually enters the opening 404 and is processed via the funnel 406. Thus, the viable newly hatched insects separate themselves from the non-viable newly hatched insects. Sensors may be placed within the funnel 406 to count the newly hatched insects as the newly hatched insects move past. The end of the funnel 406 may include multiple storage compartments 502. Each of the storage compartments 502 may receive a desired number of newly hatched insects based on a size of a habitat allocated to cultivate the adult insects. Once full, the storage compartment 502 may be closed and the next compartment 502 may be filled. In one specific example, the storage compartments 502 may be removable and a mechanical arm or other conveyor may move each of the storage compartments 502 into a habitat and release or open the storage compartment 502 to deposit the newly hatched insects into the habit.

In the current example, the each storage compartment 502 includes a retractable floor 504 or other type of opening. The retractable floor 504 may be connected to a tube or cone 406. Sensors (not shown) may be placed within the tube 406 to count the newly hatched insects as the newly hatched insects slide past. Once each of the storage compartments 502 receive a desired number of newly hatched insects the retractable floor 504 may close to separate the storage compartments 502 prior to removal.

Figure 6:
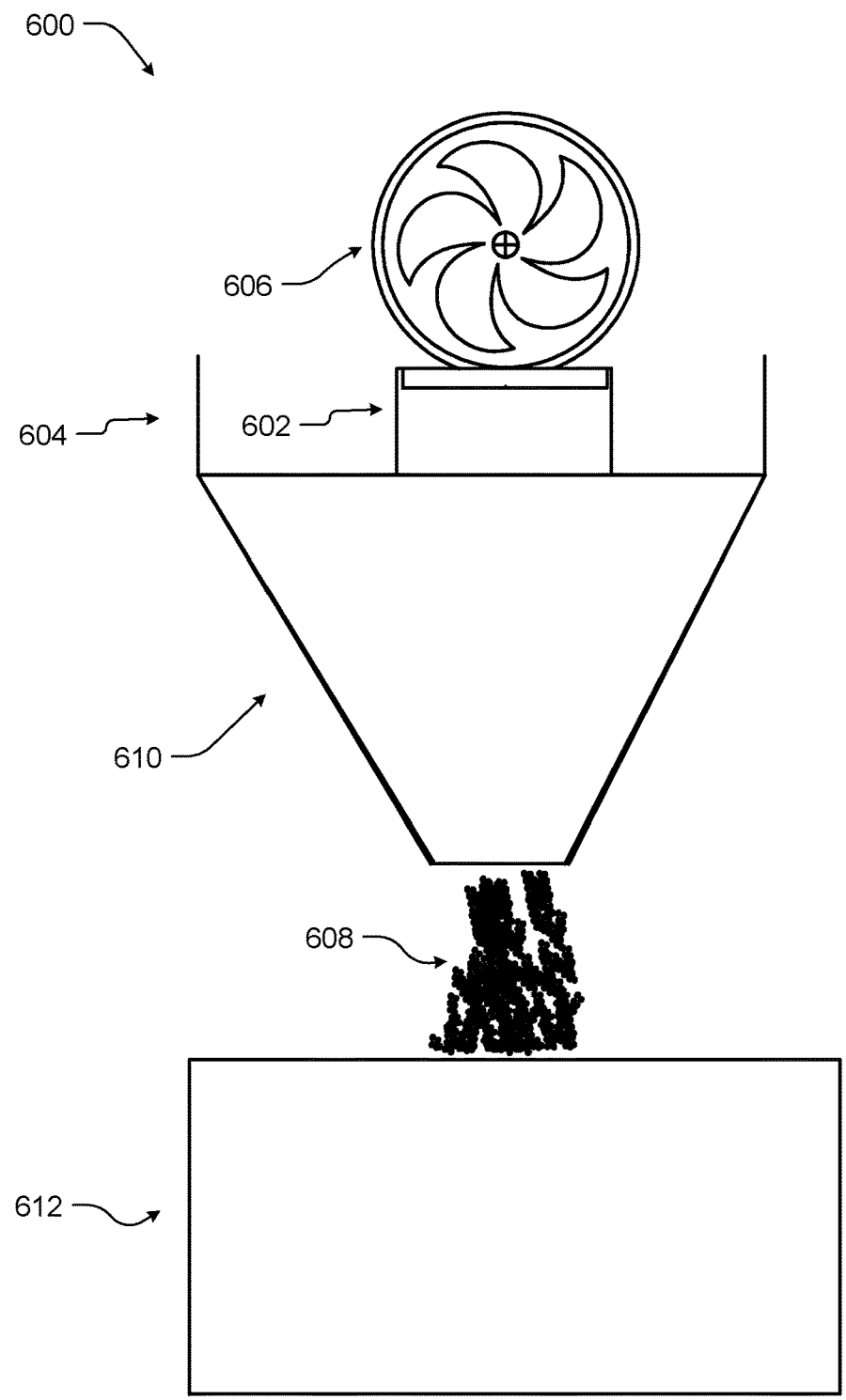
FIG. 6 illustrates an example device for use in the newly hatched insect collection area of FIG. 1 according to some implementations.

FIG. 6 illustrates an example device 600 for use in newly hatched insect collection area 116 of FIG. 1 according to some implementations. In the illustrated examples, the egg bearing medium 602 may be placed in a separation enclosure 604. The separation enclosure 604 may include an air source 606, such as a vent, fan, propeller, or jet to apply directional air flow over the egg bearing medium. The air flow may cause the viable newly hatched insects 608 to be pushed, moved, or herded into a collection chute or funnel 610. In some cases, the air flow may blow the newly hatched insects 608 that escape the medium (e.g., the newly hatched insects with enough viability to burrow out of the medium) down the chute 610 for collection, counting, and separation in a collections bin 612.

Figure 7:
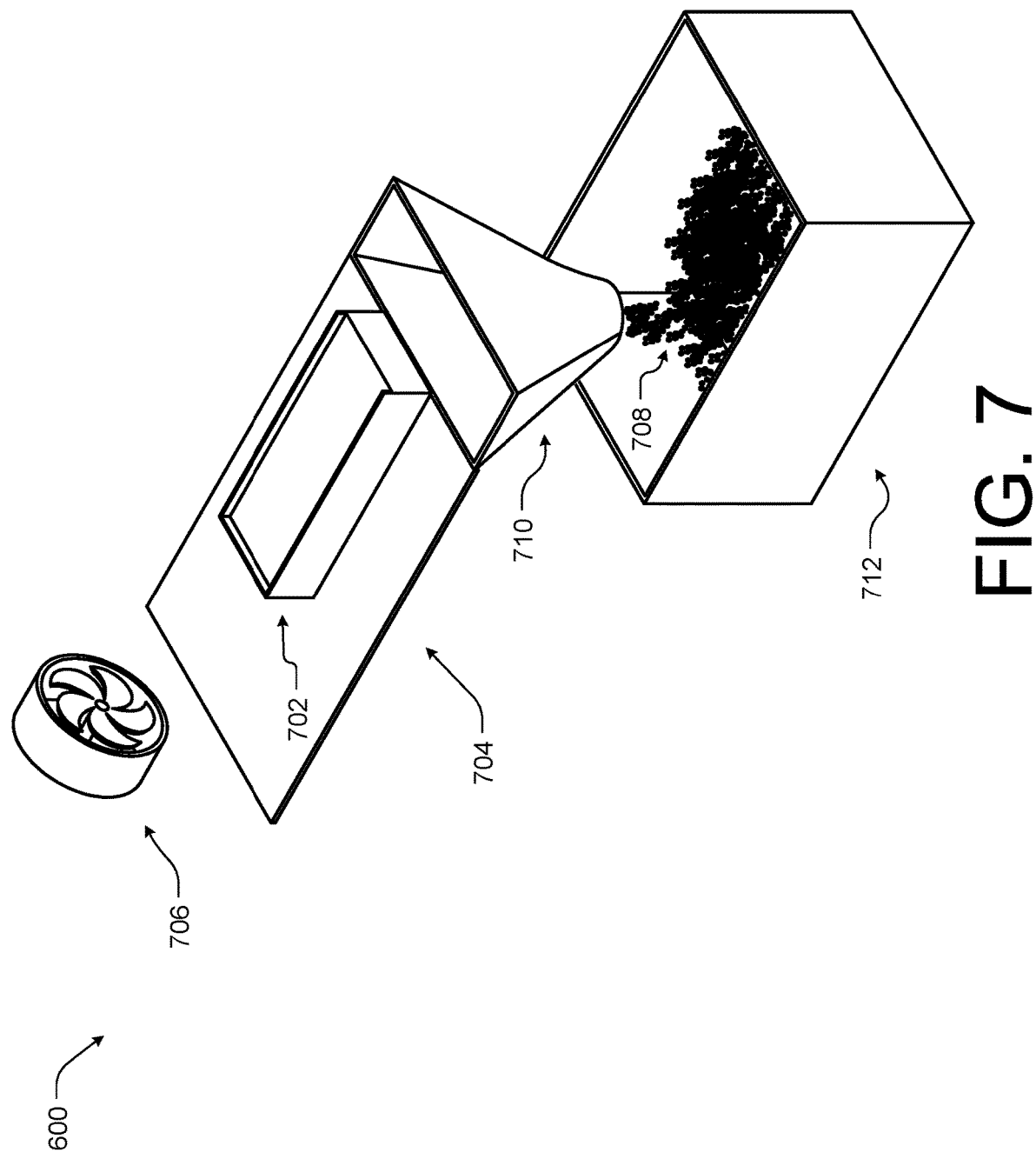
FIG. 7 illustrates another view of the separation enclosure of FIG. 6 according to some implementations.

FIG. 7 illustrates another view of the separation enclosure 600 of FIG. 6 according to some implementations. In the illustrated examples, the egg bearing medium 702 may be placed in a separation enclosure 704. The separation enclosure 704 may include an air source 706, such as a vent, fan, propeller, or jet to apply directional air flow over the egg bearing medium. The air flow may cause the viable newly hatched insects 708 to be pushed, moved, or herded into a collection chute or funnel 710. In some cases, the air flow may blow the newly hatched insects 708 that escape the medium (e.g., the newly hatched insects with enough viability to burrow out of the medium) down the chute 710 for collection, counting, and separation in a collections bin 712.

Figure 8:
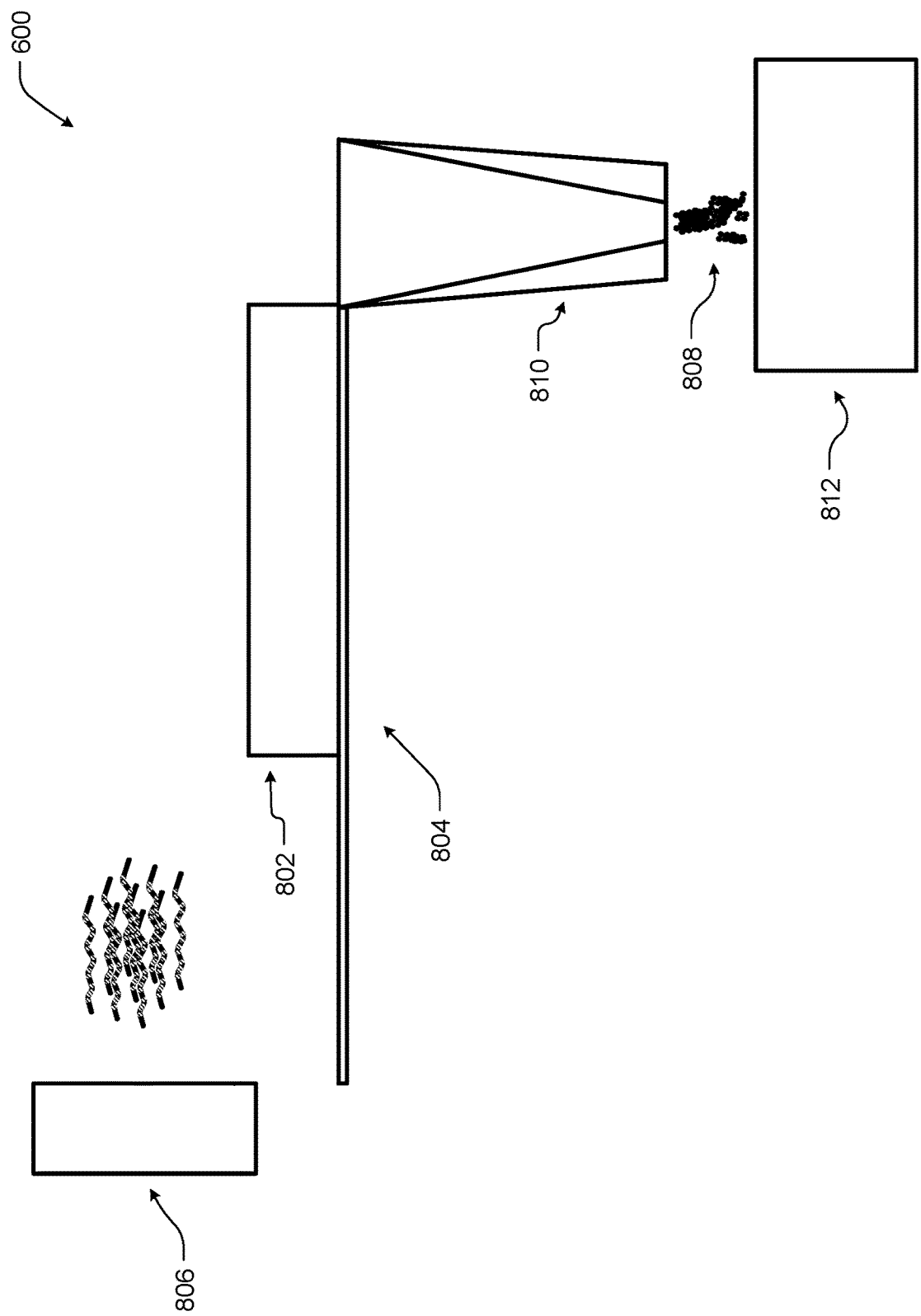
FIG. 8 illustrates yet another view of the separation enclosure of FIG. 6 according to some implementations.

FIG. 8 illustrates yet another view of the separation enclosure 600 of FIG. 6 according to some implementations. In the illustrated examples, the egg bearing medium 802 may be placed in a separation enclosure 804. The separation enclosure 804 may include an air source 806, such as a vent, fan, propeller, or jet to apply directional air flow over the egg bearing medium. The air flow may cause the viable newly hatched insects 808 to be pushed, moved, or herded into a collection chute or funnel 810. In some cases, the air flow may blow the newly hatched insects 808 that escape the medium (e.g., the newly hatched insects with enough viability to burrow out of the medium) down the chute 810 for collection, counting, and separation in a collections bin 812.

Figure 9:
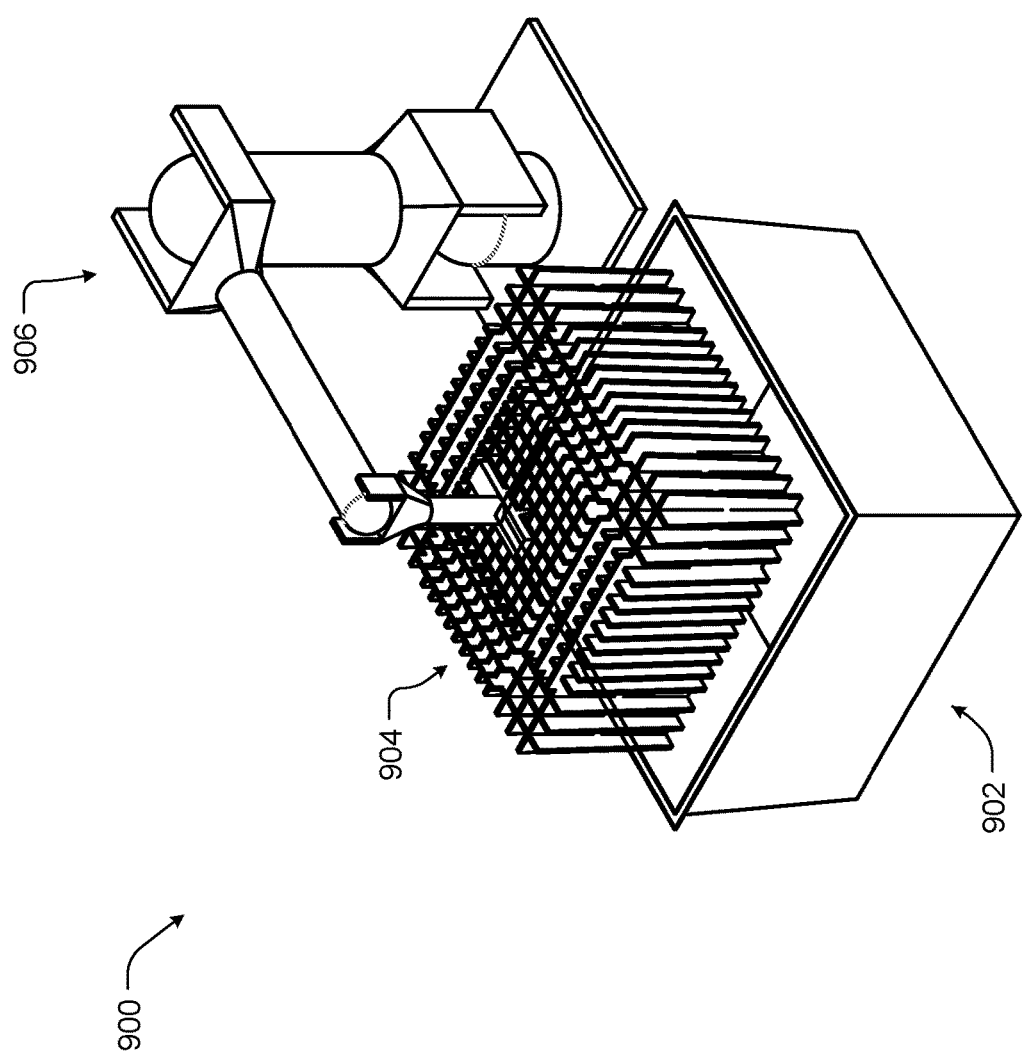
FIG. 9 illustrates an example system for use in the waste separation area of FIG. 1 according to some implementations.

FIG. 9 illustrates an example system 900 for use in a waste separation area 126 of FIG. 1 according to some implementations. In the illustrated example, once the adult insects are ready for harvesting the insects in a habitat 902 are separated from waste product. In some cases, the insects may be raised on a habitat insert 902 that is removed from the habitat 902 and may be shaken over an empty collection bin to dislodge the insects from the insert 904. In this manner, the waste remains in the habitat 902 and the live insects are deposited into the collection bins for further processing.

In the current example, a robotic arm 906 may be configured to attach or secure to the habitat insert 904, remove the insert 904 from the habitat 902, position the insert 904 over a collection bin, and vibrate or actuate the insert to cause the insects to dislodge from the insert 904 and deposit the insects within the collection bin.

Figure 10:
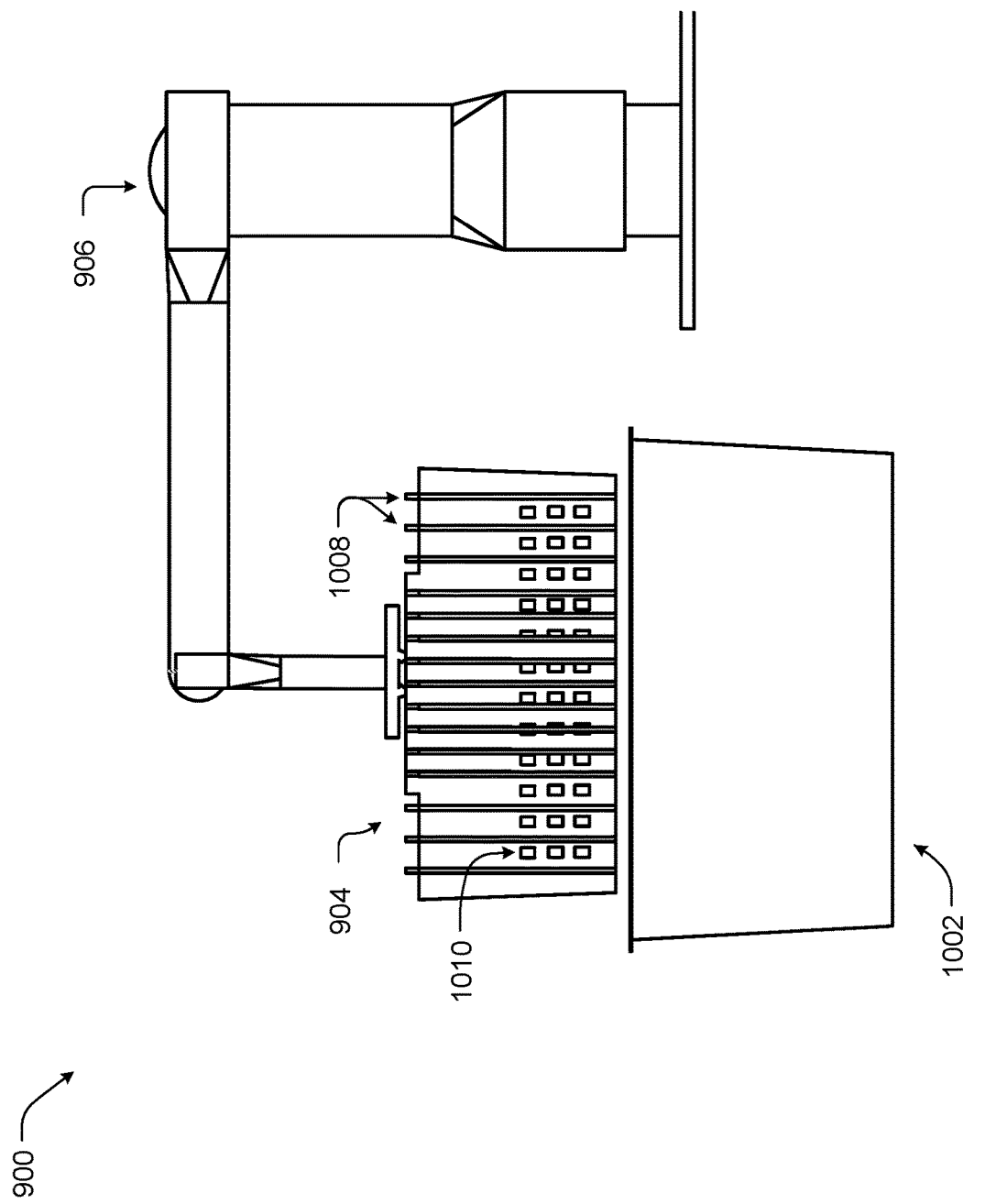
FIG. 10 illustrates a side view of the example system of FIG. 9 for use in the waste separation area of FIG. 1 according to some implementations.

FIG. 10 illustrates a side view of an example system 900 of FIG. 9 for use in a waste separation area 126 of FIG. 1 according to some implementations. As discussed above, once the adult insects are ready for harvesting the insects in a habitat 902 are separated from waste product. In some cases, the insects may be raised on a habitat insert 904 that is removed from the habitat 902 and may be shaken over an empty collection bin to dislodge the insects from the insert 904. In this manner, the waste remains in the habitat 902 and the live insects are deposited into the collection bins for further processing. In general, the habitat inserts 904 may include a grid or matrix of vertical walls 1008 that provide living space for the insects and increase the overall surface area of the habitat 902, thereby, increasing the overall population density of the habitat 902. In other cases, the inserts 904 may include horizontal walls, sloping walls or angular walls depending on the type and developmental level of the insects. In some cases, the inserts may also include perforations 1010 to allow the insects to move between sections of the habitat 902.

In the current example, a robotic arm 906 may be configured to attach or secure to the habitat insert 904, remove the insert 904 from the habitat 902, position the insert 904 over a collection bin, and vibrate or actuate the insert to cause the insects to dislodge from the insert 904 and deposit the insects within the collection bin.

Figure 11:
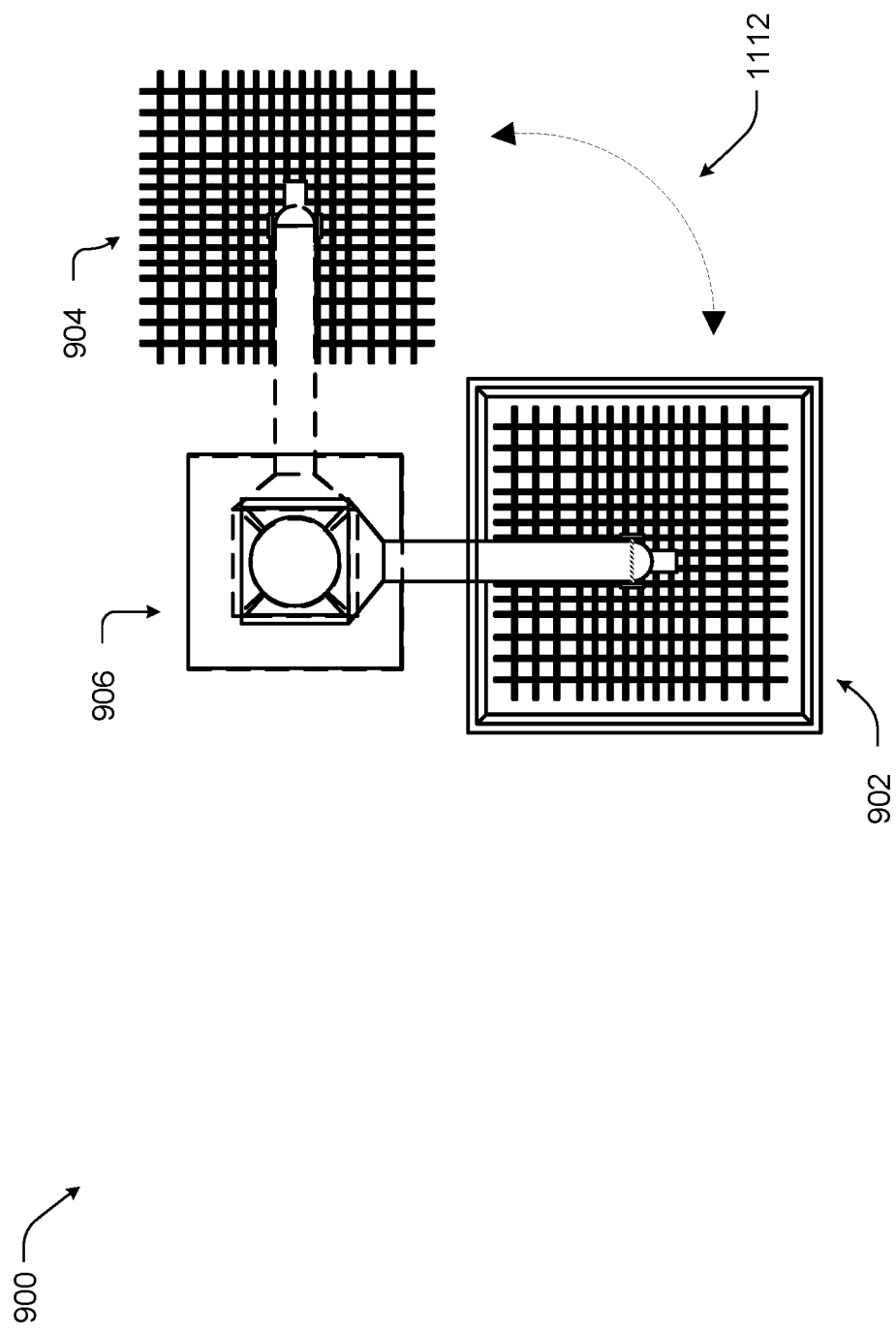
FIG. 11 illustrates a top view of the example system of FIG. 9 for use in the waste separation area of FIG. 1 according to some implementations.

FIG. 11 illustrates a top view of an example system 900 for use in a waste separation area of FIG. 9 according to some implementations. In the current example, a robotic arm 906 may be configured to attach or secure to the habitat insert 904, remove the insert 904 from the habitat 902, position the insert 904 over a collection bin as illustrated by path 1112, and vibrate or actuate the insert to cause the insects to dislodge from the insert 904 and deposit the insects within the collection bin.

Figure 12:
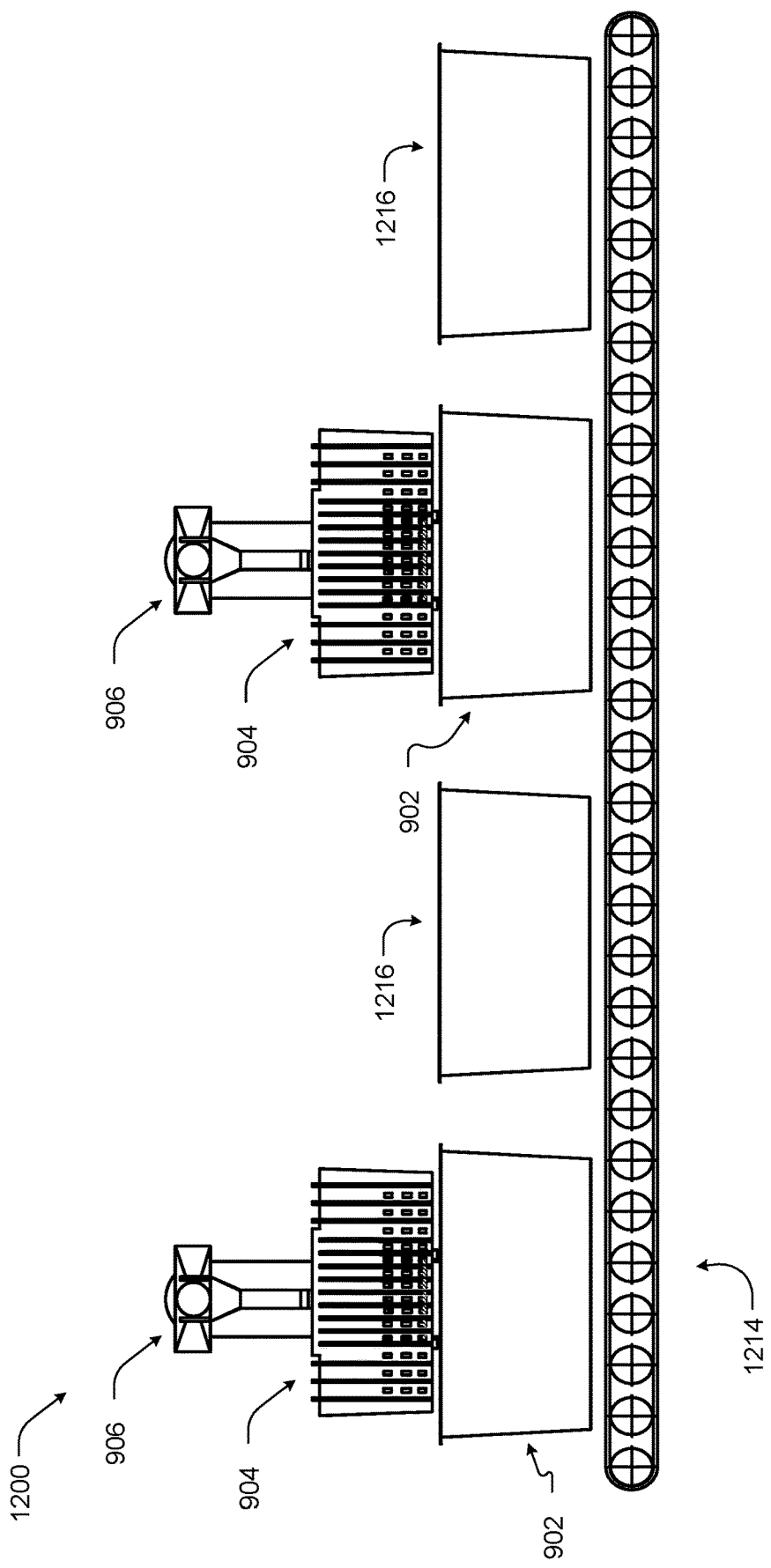
FIG. 12 illustrates the example system of FIG. 9 for use in the waste separation area of FIG. 1 according to some implementations.

FIG. 12 illustrates another example system 1200 for use in a waste separation area 126 of FIG. 1 according to some implementations. In one example, when the habitats 904 are ready to be harvested, the habitats 904 may be moved or placed upon a conveyor 1214 (such as a belt or track) which may move the habitats 904 past a robotic arm 906. The robotic arm 906 may be configured to attach or secure to the habitat insert 904, remove the insert 904 from the habit, position the insert 904 over a collection bin, and vibrate or actuate the insert to cause the insects to dislodge from the insert and deposit the insects within the collection bin. For example, the conveyor 1214 may be loaded with a habitat 904 followed by a collection bin 1216, such that the inserts 904 may be removed, the conveyor belt 1214 may move and the inserts may be dislodged into the collection bin 1216 that has moved under the insert 904.

Figure 13:
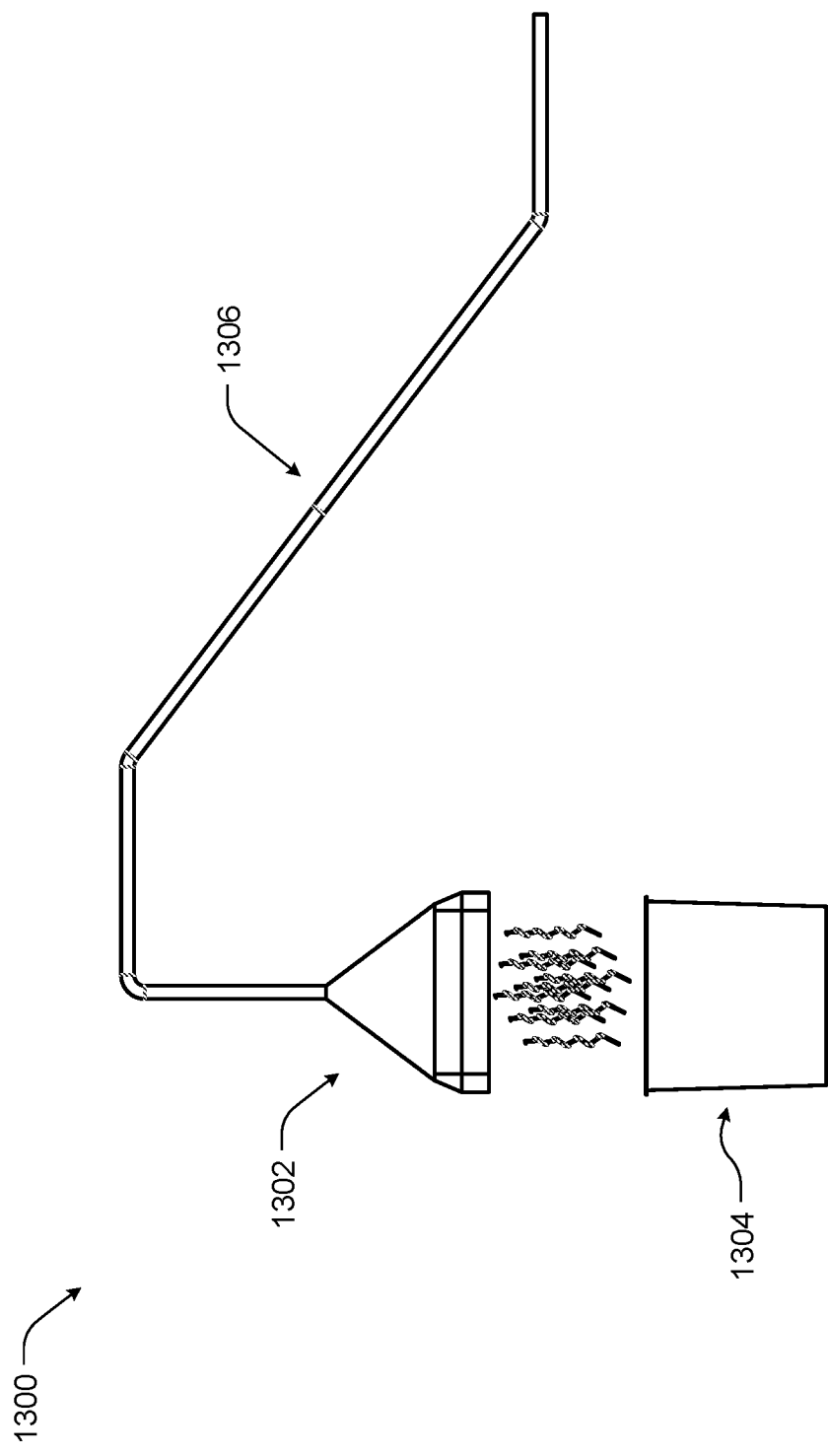
FIG. 13 illustrates the example system for use in the waste separation of FIG. 1 area according to some implementations.

FIG. 13 illustrates another example system 1300 for use in a waste separation area 116 of FIG. 1 according to some implementations. In this example, a vacuum 1302 may be configured to run either the width or length of the habitat 1304. In one instance, the habitat 1304 including the insert may be passed under the vacuum 1302 (or alternatively, the vacuum is moved over a stationary habit). The vacuum 1302 may be configured to suction out the insects located on the walls of the habitat as the habitat 1304 moves under the vacuum 1302. The section level of the vacuum 1302 may be configured based on a depth of the habitat 1304 such that material within the bottom 1%, 5%, 10% or 15% remains in the habitat 1304 while material within the top portion of the habitat 1304 is removed. Thus, the waste deposited at the bottom of the habitat 1304 while the insects grow within the habitat 1304 remains within the habitat 1304 and the insects located on the walls of the inserts are removed. The vacuum system 1300 may include a tube 1306 connected to one or more collection bin for depositing the insects within the collection bins for further processing.

Figure 14:
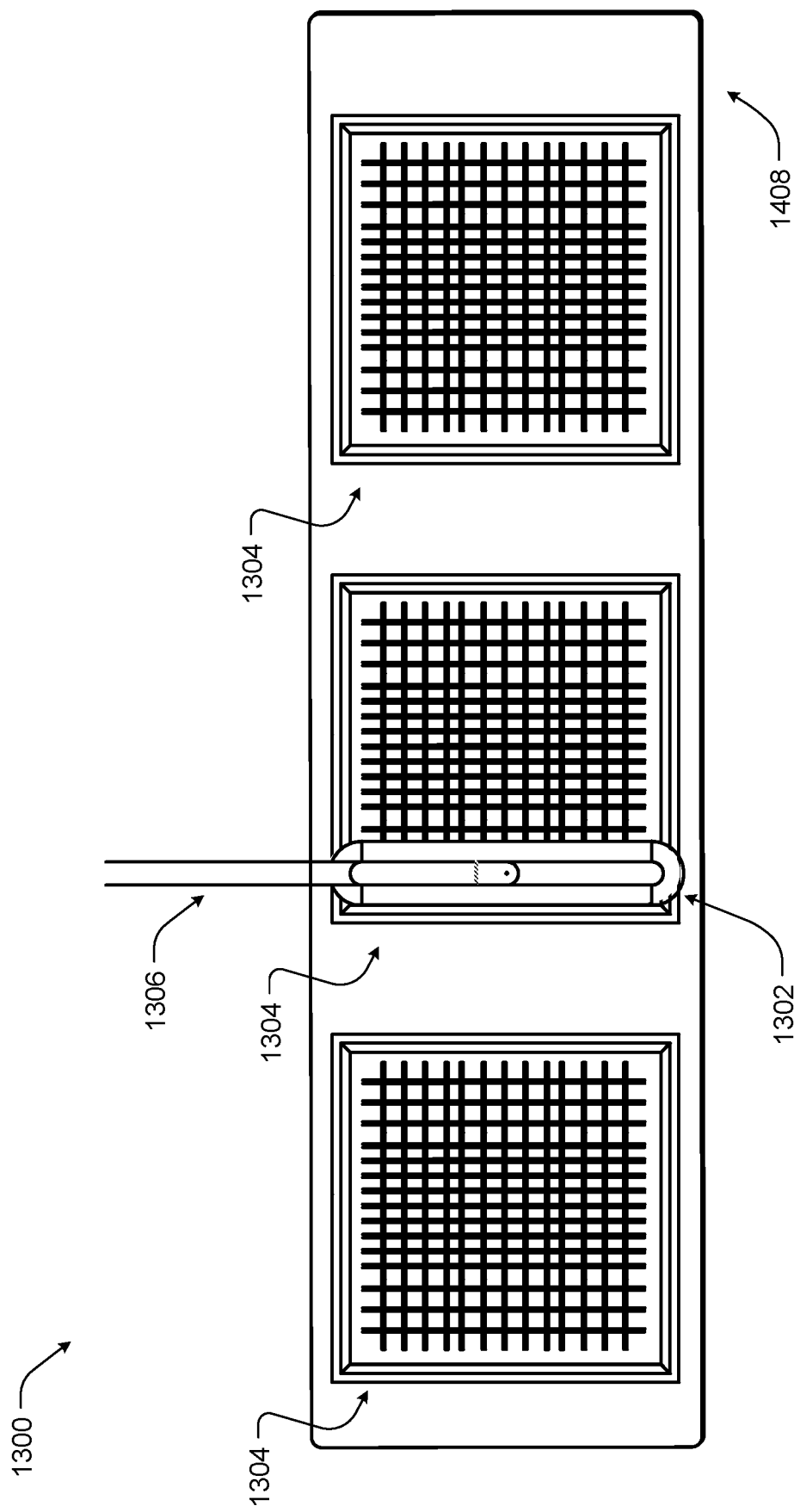
FIG. 14 illustrates the example system of FIG. 13 for use in the waste separation area of FIG. 1 according to some implementations.

FIG. 14 illustrates the example system 1300 of FIG. 13 for use in a waste separation area 126 of FIG. 1 according to some implementations. In this example, a vacuum 1302 may be configured to run either the width or length of the habitat 1304. In one instance, the habitat 1304 including the insert may be passed by a conveyor 1308 under the vacuum 1302. The vacuum 1302 may be configured to suction out the insects located on the walls of the habitat as the habitat 1304 moves under the vacuum 1302.

In some cases, the vacuum 1302 may make several passes with respect to the habitat 1304 to ensure that substantially all of the live insects are removed. For example, the vacuum 1302 and/or the habitat 1304 may include a motion sensor (or an image sensor, thermal sensor, other imaging device, or other sensor) able to detect the movement of the insects. The vacuum 1302 may make additional passes with respect to the habitat 1304 until a level of motion determined based on the data collected by the motion sensor indicates the motion is below a motion threshold.

Figure 15:
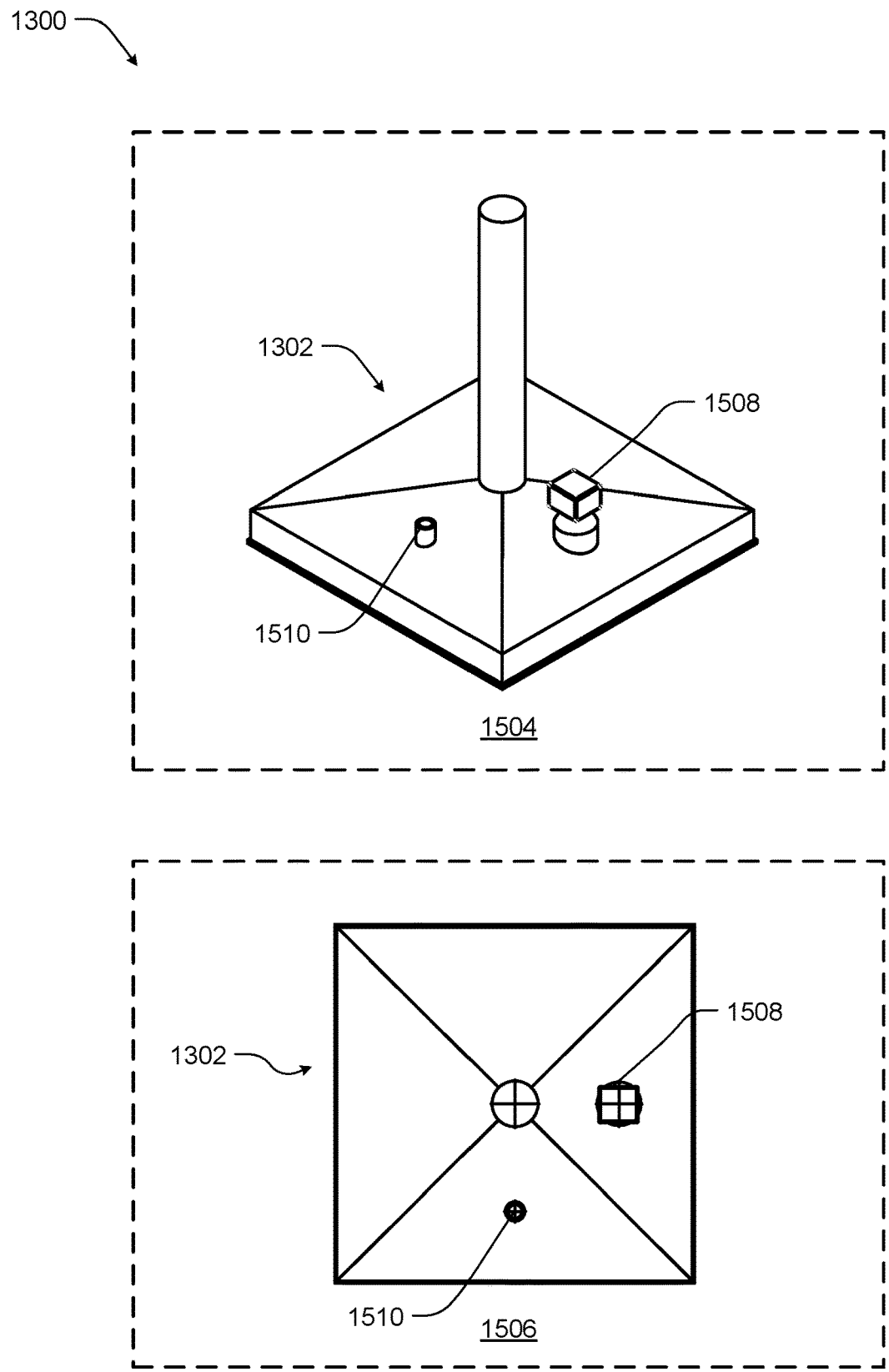
FIG. 15 illustrates additional features of the example system of FIG. 13 for use in the waste separation area of FIG. 1 according to some implementations.

FIG. 15 illustrates additional features of the example system 1300 of FIG. 13 for use in a waste separation area 126 of FIG. 1 according to some implementations. In the illustrated example, a vacuum 1302 is shown with a side view 1504 and a top view 1506. The vacuum 1302 is sized to fit over and seal with a habitat (not shown). The vacuum 1302 may be configured with a gas applicator 1508 to inject a gas (such as carbon dioxide $CO_2$ or freezing air) into the sealed habitats to kill or sedate the insects prior to removing via the vacuum 1302 and a vent 1510 to release or siphon the gas after the application is complete.

Figure 16:
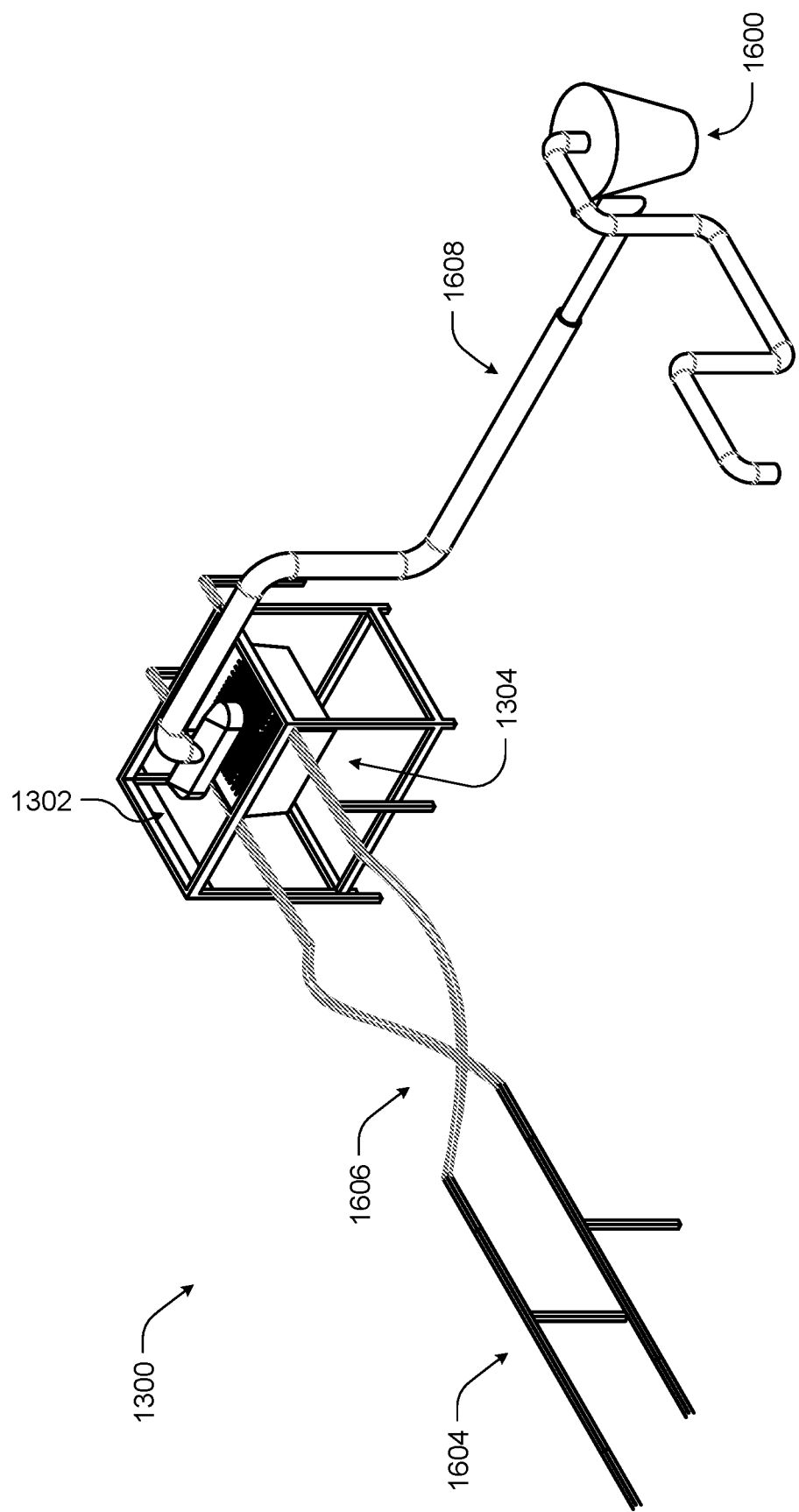
FIG. 16 illustrates the example system of FIG. 13 for use in the waste separation area of FIG. 1 according to some implementations.

FIG. 16 illustrates the example system 1300 of FIG. 13 for use in a waste separation area 126 of FIG. 1 according to some implementations. In this example, the inserts may be configured to attach or secure to the habitat 1304 (such that the inserts may be removed for cleaning or remain within the habitat 1304 when the habitat 1304 is flipped over). For instance, a conveyor 1604 carrying the habitat 1304 may cause the habitat 1304 to flip over or upside-down at a particular location 1606 to cause the remaining waste within the habitat 1304 to be dumped or removed after the live insects are removed, for instance, by the vacuum 1302 in the illustrated example. In some cases, the conveyor 1604 may vibrate or actuate to cause the habitats 1304 to vibrate and further assist with the waste removal. In some instances, the habitats 1304 may be moved to a wash station which may remove any remaining waste prior to having an insert placed back within the habitat 1304. The habitat 1304 may be moved to a position within the system at which the newly hatched insects or eggs may be placed for the cultivation of a new population of insects.

Figure 17:
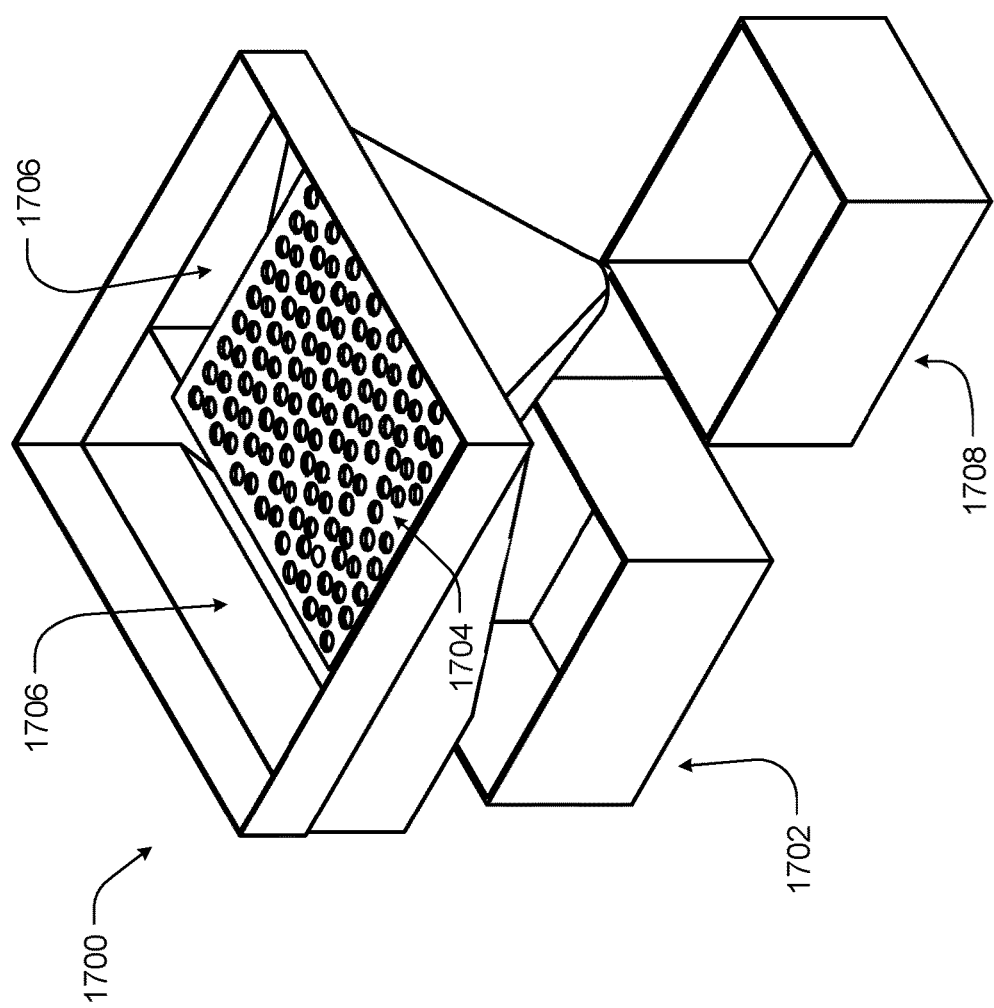
FIG. 17 illustrates another example system for use in the waste separation area of FIG. 1 according to some implementations.

FIG. 17 illustrates another example system 1700 for use in a waste separation area 126 of FIG. 1 according to some implementations. In the current example, rather than removing insects from the habitat the insects may be encourage or herded into the collection bins 1702. For example, the contents of the habitat may be dumped or deposited onto a mesh or screen 1704 that allows some material to pass but retains the live insects. The mesh or screen 1704 may be surrounded by or adjacent to a collection area, tube, or funnel 1706 that the live insects migrate into overtime. The live insects may then be transferred to via the collection area to the collection bin 1702 (e.g., by sliding down the tube having a low friction wall). After a period of time following the placement of the contents on to the mesh or screen, the screen 1704 may open and the remaining material may be deposited with the other waste in a waste receptacle 1708.

FIG. 18 illustrates the example system 1700 of FIG. 17 for use in a waste separation area 126 of FIG. 1 according to some implementations. In the current example, rather than removing insects from the habitat the insects may be encourage or herded into the collection bins 1702. For example, the contents of the habitat may be dumped or deposited onto a mesh or screen 1704 that allows some material to pass but retains the live insects. The mesh or screen 1704 may be surrounded by or adjacent to a collection area, tube, or funnel 1706 that the live insects migrate into overtime. The live insects may then be transferred to via the collection area to the collection bin 1702 (e.g., by sliding down the tube having a low friction wall). After a period of time following the placement of the contents on to the mesh or screen, the screen 1704 may open and the remaining material may be deposited with the other waste in a waste receptacle 1708.

Figure 19:
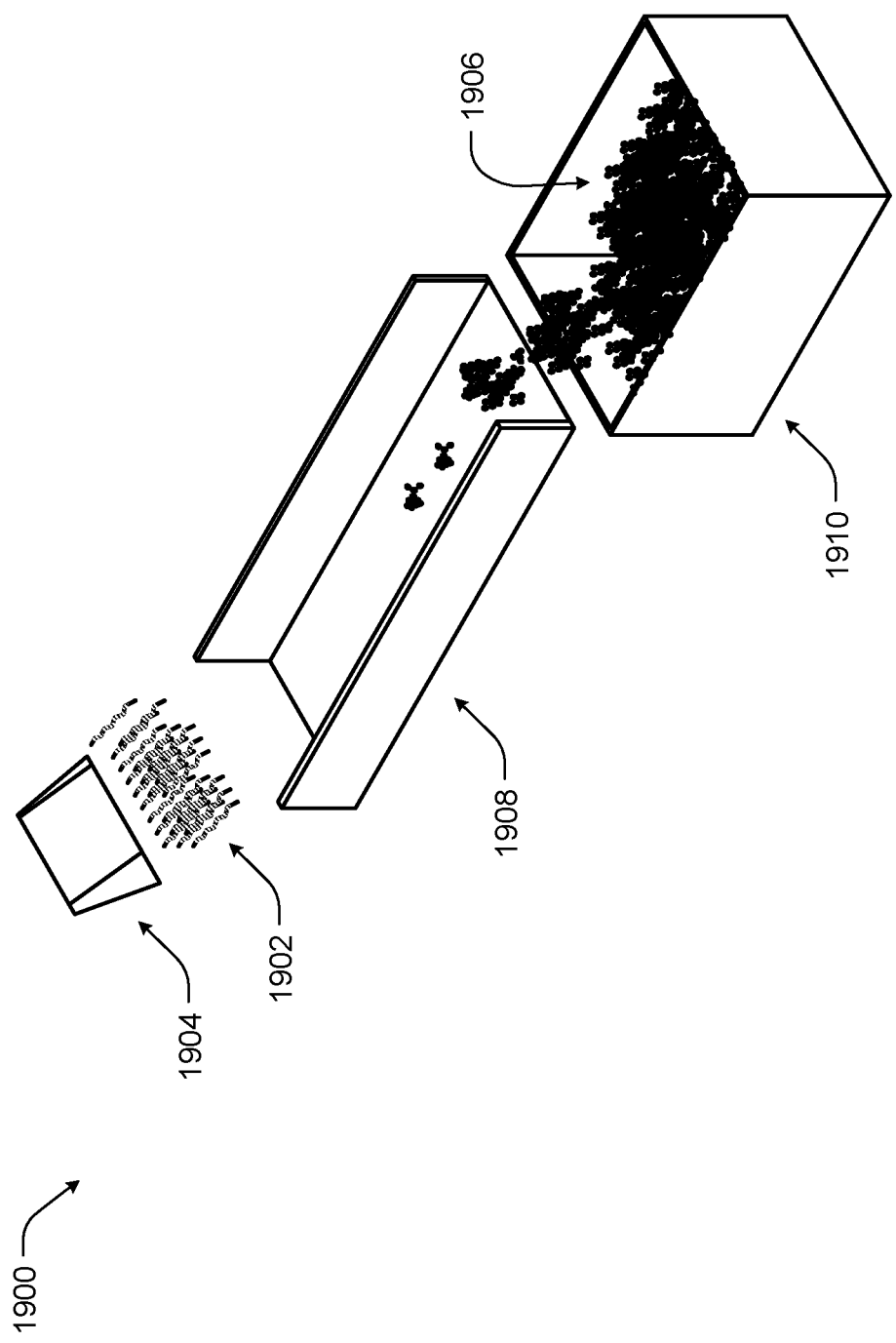
FIG. 19 illustrates another example system for use in the waste separation area of FIG. 1 according to some implementations.

FIG. 19 illustrates another example system 1900 for use in a waste separation area 126 of FIG. 1 according to some implementations. In the illustrated example, an environmental stimulus 1902, such as light, air, temperature, gas, sound, may introduced via an environmental stimulus device 1904 to the insects 1906 to cause the insects 1906 to move in a particular direction away from the environmental stimulus device 1904 along a corridor 1908 towards the collection bin 1910. For example, a strobe light may be utilized to cause the insects 1906 to move in the opposite direction from the source. In some cases, the corridor 1908 the insects 1906 are placed on may vibrate in sections or irritate the insects 1906 to case them to move toward the collection bin 1910. In another example, an attractor, such as pheromones or food, may be introduced via an attractor device at location to cause the insects to move toward the attractor device and the collection bin 1910.

Figure 20:
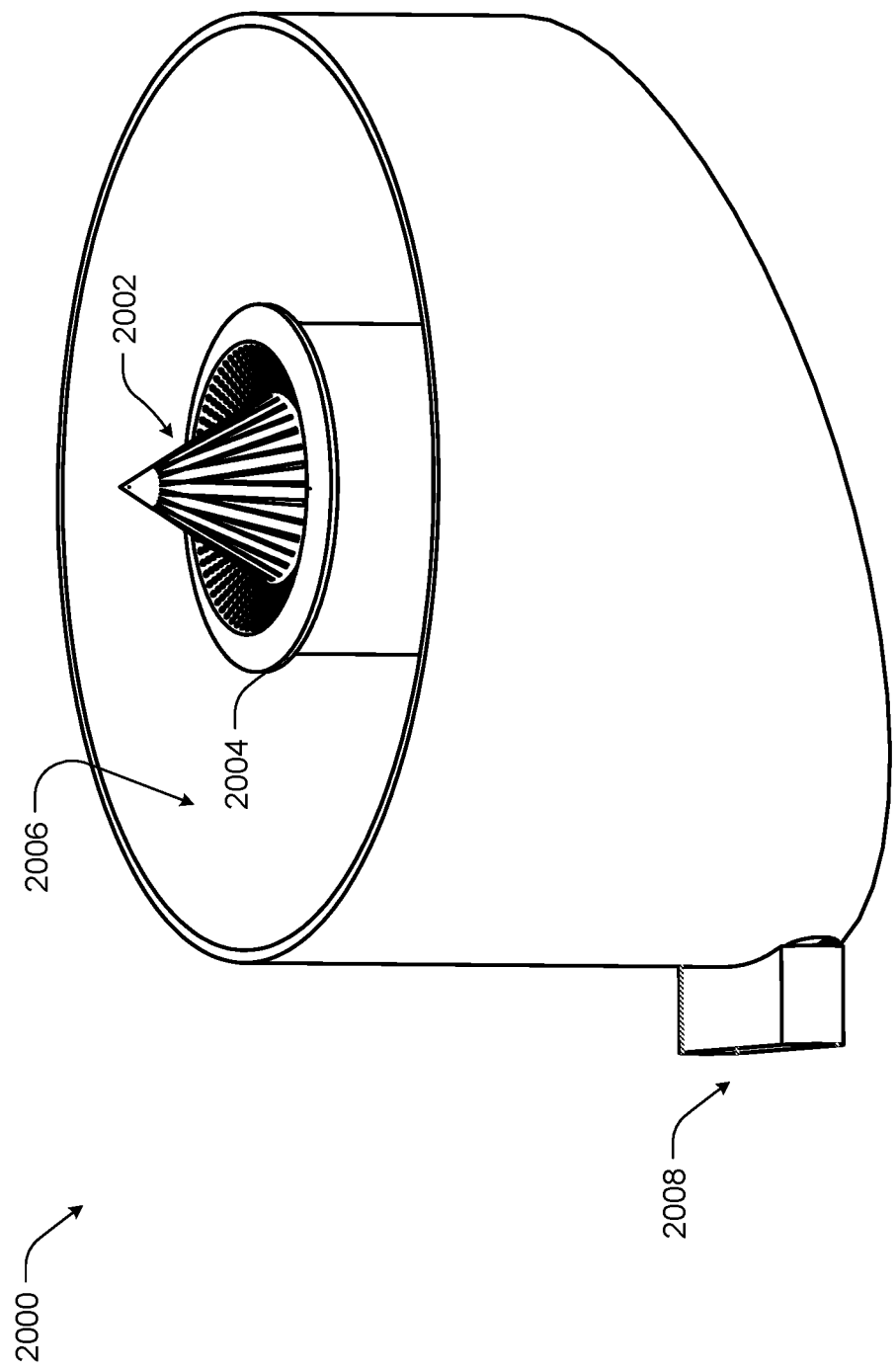
FIG. 20 illustrates another example system for use in the waste separation area of FIG. 1 according to some implementations.

FIG. 20 illustrates another example system 2000 for use in a waste separation area 126 of FIG. 1 according to some implementations. In the current example, the system is designed to harvest live insects. For example, the contents of a habitat may be dumped or placed on a central area, generally indicated by 2002. The central area 2002 may include a mesh or screen that allows waste to pass but readings the live insects on top. The live insect may move around until the insects walk over a low friction surface 2004 which causes the insects to slide into a collection area 2006 or off the edge of the low friction surface 2004. The live insects are then collected in a collection bin at the end of the collection chute 2008. By allowing the live insects to separate themselves from the waste product, the system 2000 ensures that only insects alive at the time of collection are placed within a collection bin for processing thereby maintaining the quality and health conditions necessary for producing products for human consumption and use.

Figure 21:
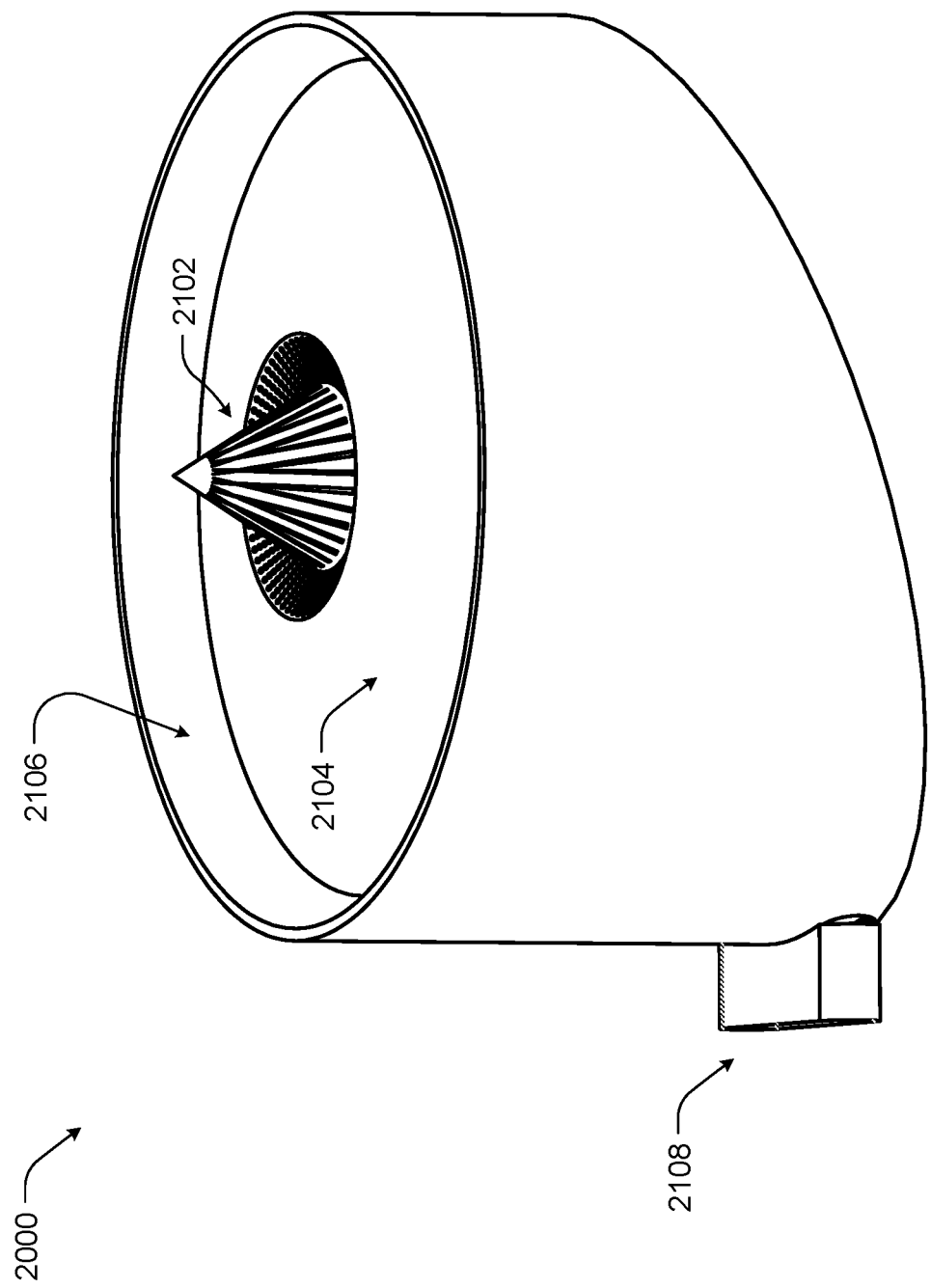
FIG. 21 illustrates the example system of FIG. 20 for use in the waste separation area of FIG. 21 according to some implementations.

FIG. 21 illustrates another example system 2000 of FIG. 20 for use in a waste separation area 126 of FIG. 1 according to some implementations. In the current example, the system is designed to harvest live insects, as discussed above with respect to FIG. 20. For example, the contents of a habitat may be dumped or placed on a central area, generally indicated by 2002. The central area 2002 may include a mesh or screen that allows waste to pass but retains the live insects on top. The live insect may move around until the insects walk over a low friction surface 2004 which causes the insects to slide into a collection area 2006 or off the edge of the low friction surface 2004. In the current example, the low friction surface 2004 is extended to prevent unwanted waste from incidentally accessing the collection bin. In some cases, a portion of the surface 2004 may be low friction while the portion closer to the central area 2002 may have a normal or higher friction. The live insects are then collected in a collection bin at the end of the collection chute 2008. By allowing the live insects to separate themselves from the waste product, the system 2000 ensures that only insects alive at the time of collection are placed within a collection bin for processing thereby maintaining the quality and health conditions necessary for producing products for human consumption and use.

Figure 22:
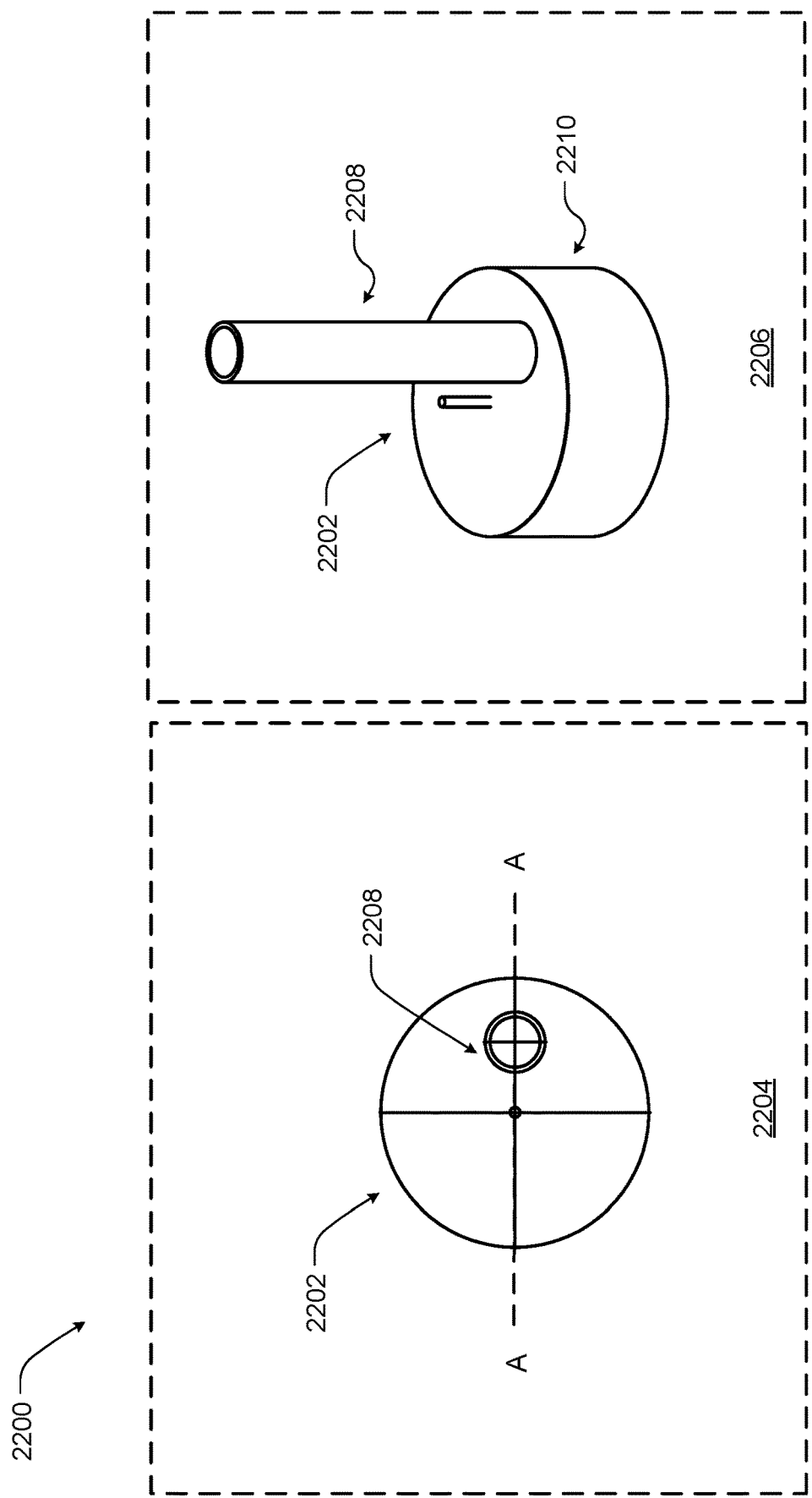
FIG. 22 illustrates another example system for use in the processing area of FIG. 1 according to some implementations.

FIG. 22 illustrates another example system 2200 for use in a processing area 132 of FIG. 1 according to some implementations. In the illustrated example, a tumbler 2202 is shown in a top view 2204 and a side view 2206. The tumbler 2202 generally includes a tube 2208 for receiving the insects that have been sorted from the waste in the habitats. The tumbler 2202 also includes a basin area that includes an inner section that may spin or tumble the insects to separate the limbs, heads, and abdomens of the insects from each other, as described in more detail below with respect to FIG. 21.

Figure 23:
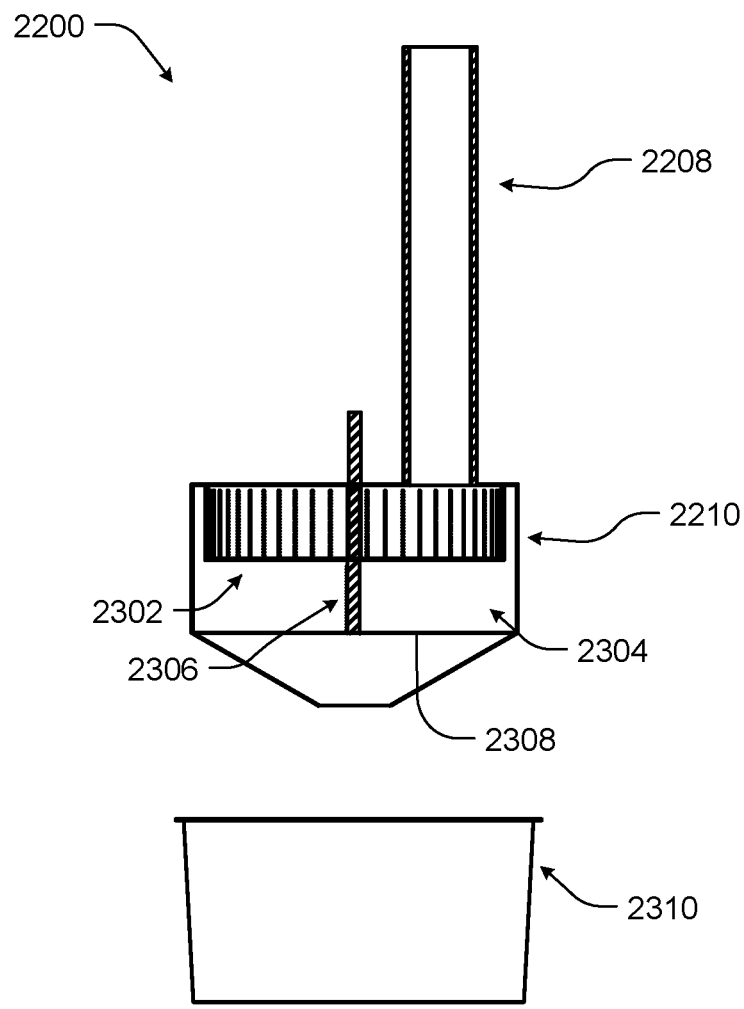
FIG. 23 illustrates a cross-sectional view of the system of FIG. 22 for use in the processing area of FIG. 1 according to some implementations.

FIG. 23 illustrates a cross-sectional view of the system 2200 of FIG. 22 for use in the processing area 132 of FIG. 1 according to some implementations. A majority of the chitin is present in the limbs and head of the insects. Thus, the tumbler 2200 may include an inner section 2302 with corrugated exterior portions (the size of the corrugation to allow the limbs portion to pass but not the bodies). The inner section 2302 may be configured to spin and as the insects spin the limbs and heads to become detached from the abdomens. The limbs may fall through the corrugation on the exterior portion. Thus, the tumbler 2200 may utilize a combination of gravity and centrifugal force to separate the limbs and heads of the insects from the abdomens of the insects. The limbs may then be removed from the tumbler.

After tumbling, the remaining abdomens and heads may be released from the inner section 2302 into a powdering section 2304. The powdering section 2304 may include an powdering device 2306 that powderizes the abdomens as the tumbler 2200 spins. As the abdomens are softer than the heads, the heads remain intake during the powderization. The bottom of the tumbler 2200 may then open to a screen or mesh 2108 to allow the power to be removed from the tumbler leaving behind the heads. The screen 2308 may then release to collect the heads. In this manner, the limbs, heads, and abdomens may be separated into different collection bins 2310 and processed into different types of final end goods.

Figure 24:
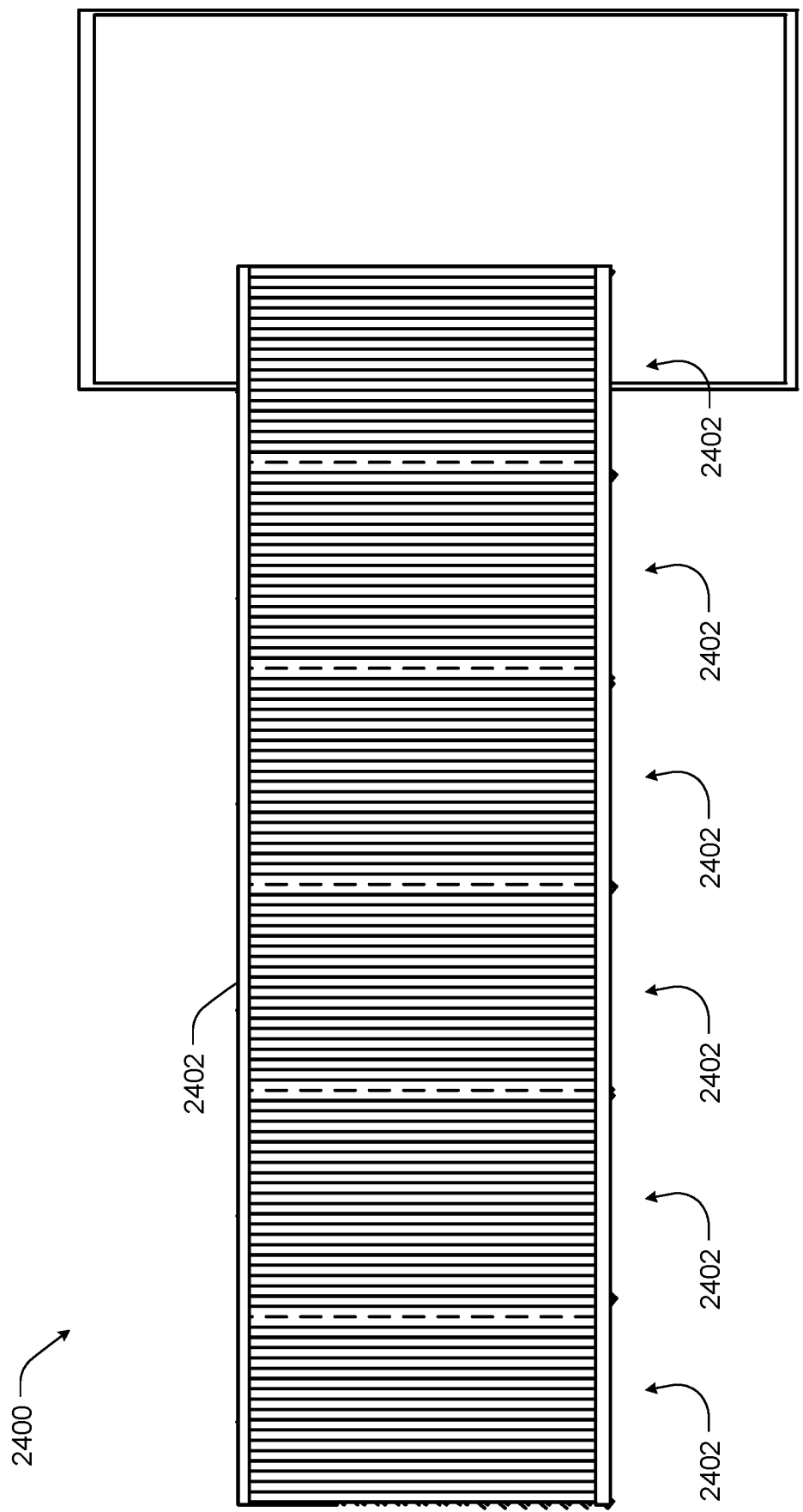
FIG. 24 illustrates another example for use in the processing area of FIG. 1 according to some implementations.

FIG. 24 illustrates another example system for use in the processing area according 134 of FIG. 1 to some implementations. In the current example, a vibration plate 2400 may be used to separate the limbs, heads, and abdomens of the insects. For example, the vibration plate 2400 may utilize a combination of friction and movement to separate the limbs and head from the abdomens. In one case, a conveyor or belt may move over a plurality of vibrating plates/sections, generally indicated by sections 2402, which vibrate at different frequencies to cause the body parts to separate. The conveyor or belt may include a fine mesh that allows the limbs or appendages of the insects to pass through following separation. The heads and abdomens may be passed into a tumbler to powderize the abdomens as discussed above.

Figure 25:
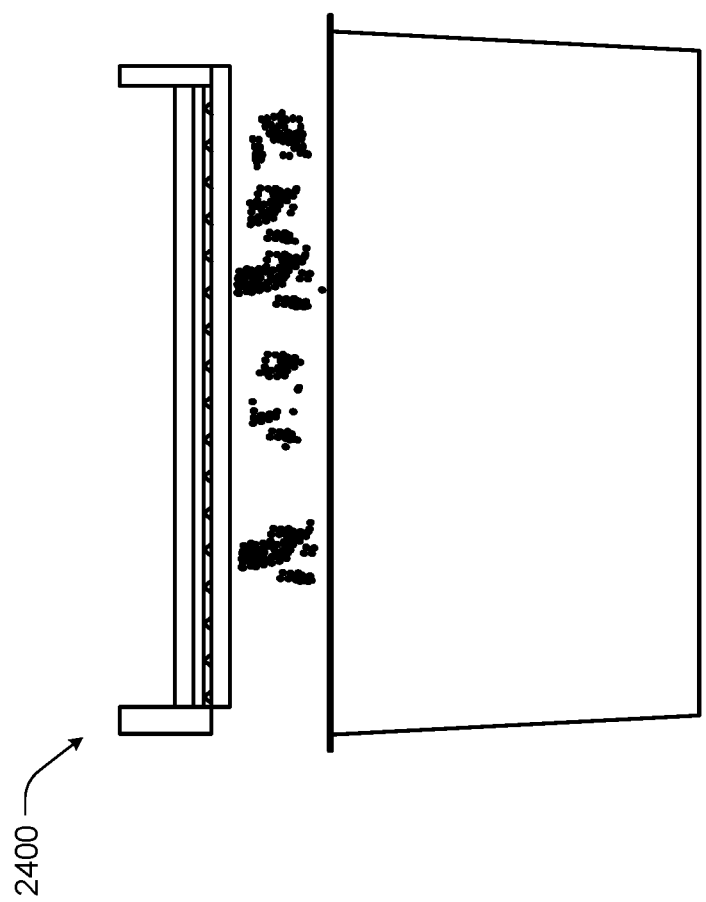
FIG. 25 illustrates the example system of FIG. 24 for use in the processing area of FIG. 1 according to some implementations.

FIG. 25 illustrates the example system of FIG. 24 for use in the processing area 132 of FIG. 1 according to some implementations. In the current example, a vibration plate 2400 may be used to separate the limbs, heads, and abdomens of the insects. For example, the vibration plate 2400 may utilize a combination of friction and movement to separate the limbs and head from the abdomens. In one case, a conveyor or belt may move over a plurality of vibrating plates/sections that vibrate at different frequencies to cause the body parts to separate. The conveyor or belt may include a fine mesh that allows the limbs or appendages of the insects to pass through following separation. The heads and abdomens may be passed into a tumbler to powderize the abdomens as discussed above.

Figure 26:
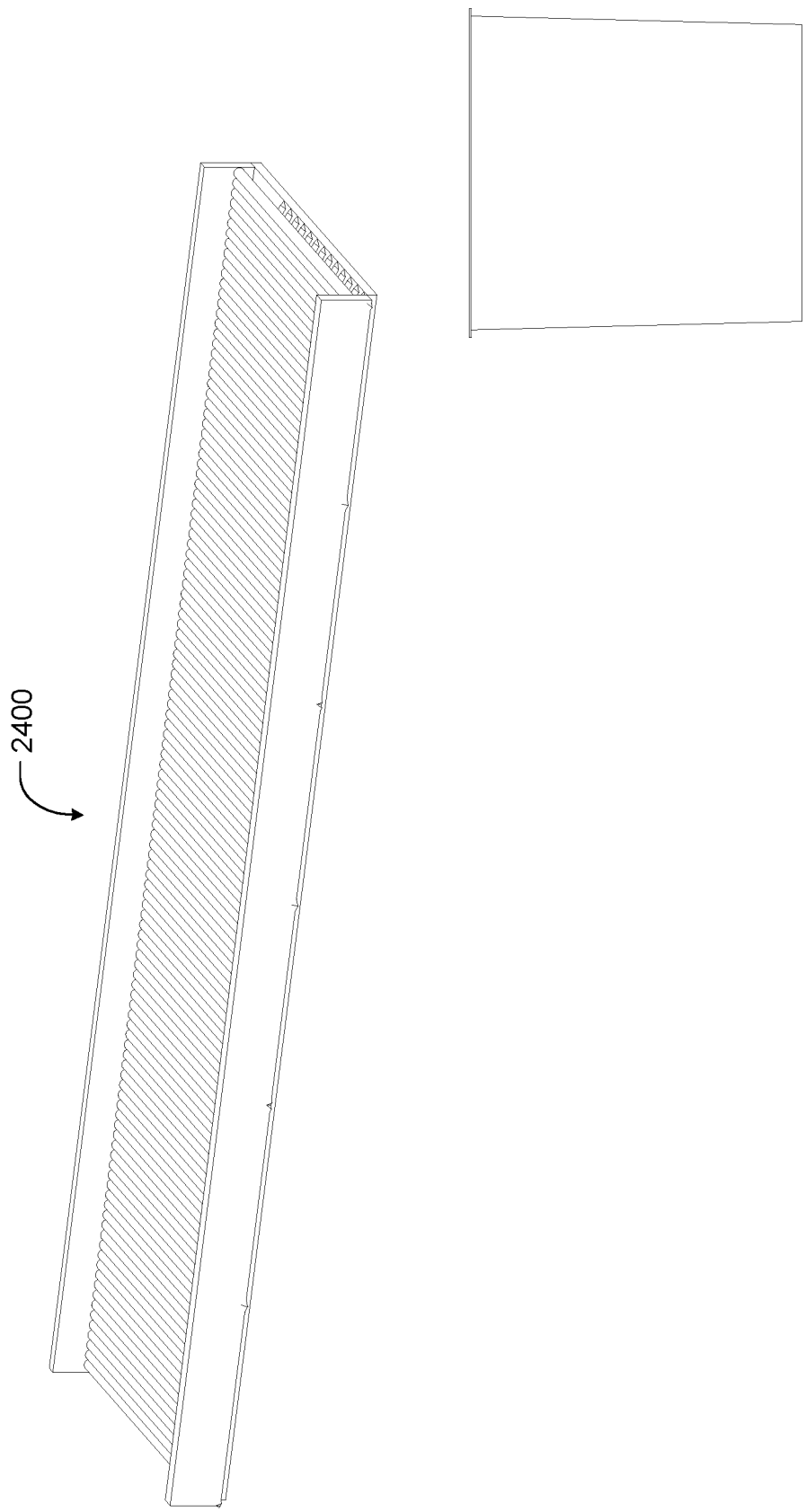
FIG. 26 illustrates the example system of FIG. 24 for use in the processing area of FIG. 1 according to some implementations.

FIG. 26 illustrates the example system 2400 of FIG. 24 for use in a processing area 132 of FIG. 1 according to some implementations. In the current example, a vibration plate 2400 may be used to separate the limbs, heads, and abdomens of the insects. For example, the vibration plate 2400 may utilize a combination of friction and movement to separate the limbs and head from the abdomens. In one case, a conveyor or belt may move over a plurality of vibrating plates/sections that vibrate a different frequencies to cause the body parts to separate. The conveyor or belt may include a fine mesh that allows the limbs or appendages of the insects to pass through following separation. The heads and abdomens may be passed into a tumbler to powderize the abdomens as discussed above.

FIG. 27 illustrates another example system 2700 for use in a processing area 132 of FIG. 1 according to some implementations. In the illustrated example, the limbs, head, and abdomens may be separated via alignment slicing. Alignment slicing is the process of translationally and rotationally adjusting insects such that each insect shares an orientation. As shown in the current example, an insect is moved via a conveyor 2702 towards a cutting or slicing apparatus 2704. As the insect moves toward the cutting or slicing apparatus 2704, the insect impacts walls 2706 which force the insect to orient into a desired orientation prior to the removal of the limbs and head.

Once the specific orientation is achieved, the insects can be separated mechanically via cutting and/or slicing. In one example, the insect move across a conveyor. As the insect moves translationally each insect impacts geometry (e.g., a wall with specific orientation) that forces the insect to orient to a specific direction. Once oriented, the insects are moved into a slicing/cutting device. The slicing/cutting device separates the insect into portions by slicing the limbs or appendages and head from the abdomens.

Figure 28:
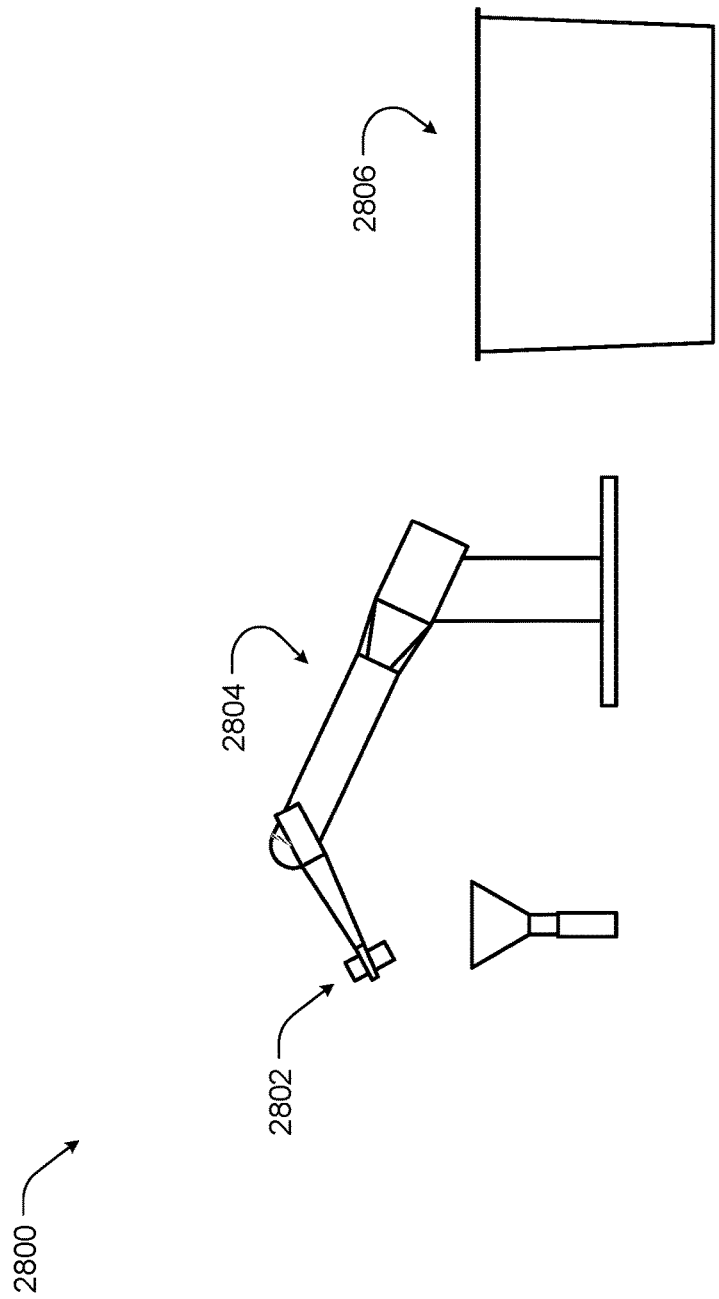
FIG. 28 illustrates an example system for use in the egg or newly hatched insect collection area, the waste separation area, or the processing area of FIG. 1 according to some implementations.

FIG. 28 illustrates an example system 2800 for use in the egg or newly hatched insect collection area 116, the waste separation area 126, or in the processing area 132 of FIG. 1 according to some implementations. In the various examples described herein, the eggs, newly hatched insects, and/or insects may be collected into measuring tubes of vials 2802. For example, the eggs, newly hatched insects, or insects may be allowed to collect in a chute having multiple tubes or vials 2802 that may be removable. In these examples, a robotic arm 2804 may be configured to detect or determine when a tube or vial 2802 is full, secure to the tube or vial 2802 and deposit the contents into a habitat 2806. In this manner, the eggs, newly hatched insects, or insects may be moved from collection areas to habitats 2806 or from habitat 2806 to habitat 2806 in a secure manner without incidental human contact.

Figure 29:
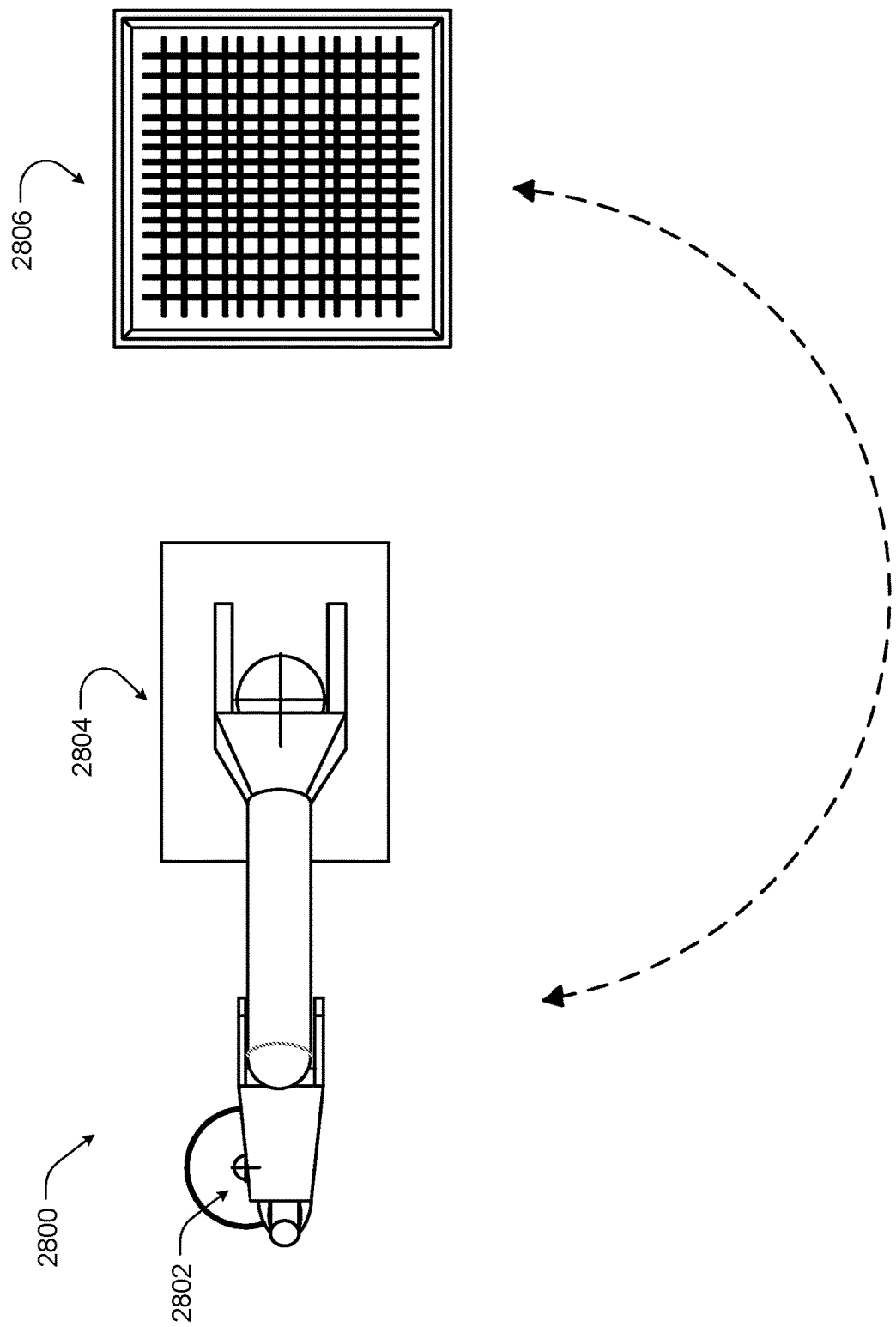
FIG. 29 illustrates a top view of the example system of FIG. 28 for use in the egg, the newly hatched insect collection area, or the waste separation area a processing area according to some implementations.

FIG. 29 illustrates a top view of the example system 2800 of FIG. 28 for use in the egg, the newly hatched insect collection area 116, or the waste separation area 126, or the processing area according 132 of FIG. 1 according to some implementations. In the various examples described herein, the eggs, newly hatched insects, and/or insects may be collected into measuring tubes of vials 2802. For example, the eggs, newly hatched insects, or insects may be allowed to collect in a chute having multiple tubes or vials 2802 that may be removable. In these examples, a robotic arm 2804 may be configured to detect or determine when a tube or vial 2802 is full, secure to the tube or vial 2802 and deposit the contents into a habitat 2806. In this manner, the eggs, newly hatched insects, or insects may be moved from collection areas to habitats 2806 or from habitat 2806 to habitat 2806 in a secure manner without incidental human contact.

Figure 30:
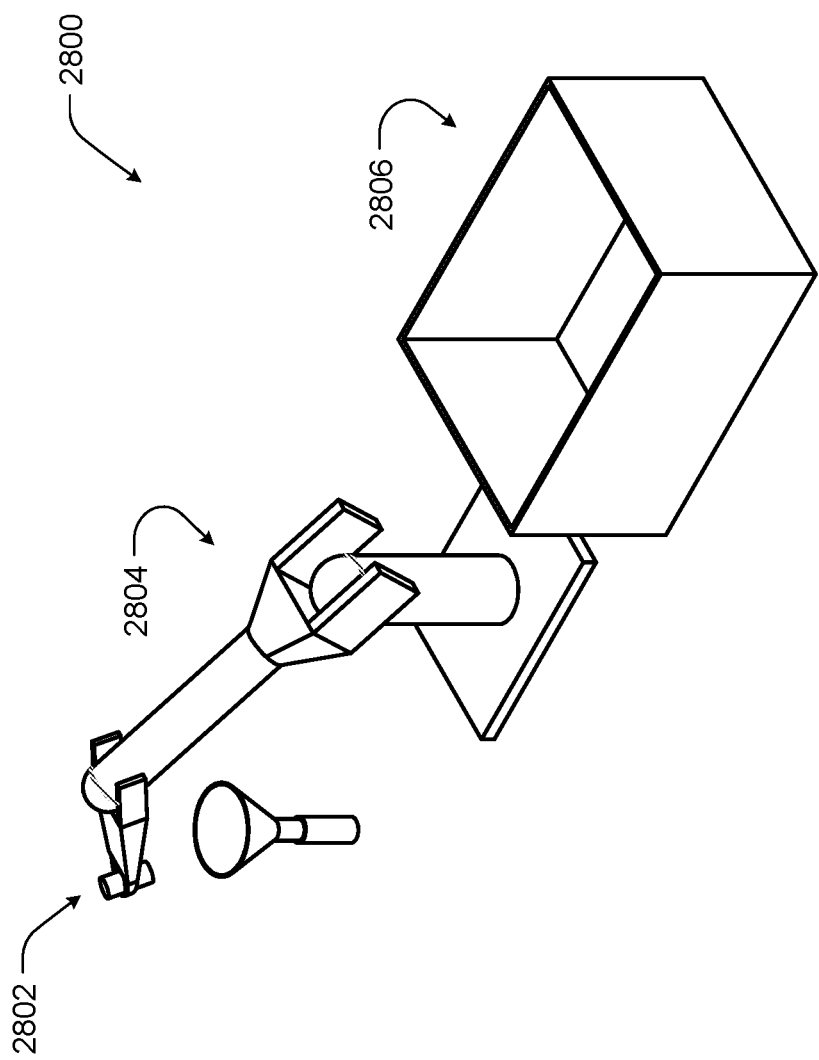
FIG. 30 illustrates a perspective view of the example system of FIG. 28 for use in the egg or newly hatched insect collection area, the waste separation area, or the processing area of FIG. 1 according to some implementations.

FIG. 30 illustrates a perspective view of the example system 2800 of FIG. 28 for use in the egg or newly hatched insect collection area 116, the waste separation area 126, or the processing area 132 of FIG. 1 according to some implementations. In the various examples described herein, the eggs, newly hatched insects, and/or insects may be collected into measuring tubes of vials 2802. For example, the eggs, newly hatched insects, or insects may be allowed to collect in a chute having multiple tubes or vials 2802 that may be removable. In these examples, a robotic arm 2804 may be configured to detect or determine when a tube or vial 3002 is full, secure to the tube or vial 2802 and deposit the contents into a habitat 3006. In this manner, the eggs, newly hatched insects, or insects may be moved from collection areas to habitats 2806 or from habitat 2806 to habitat 2806 in a secure manner without incidental human contact.

Figure 31:
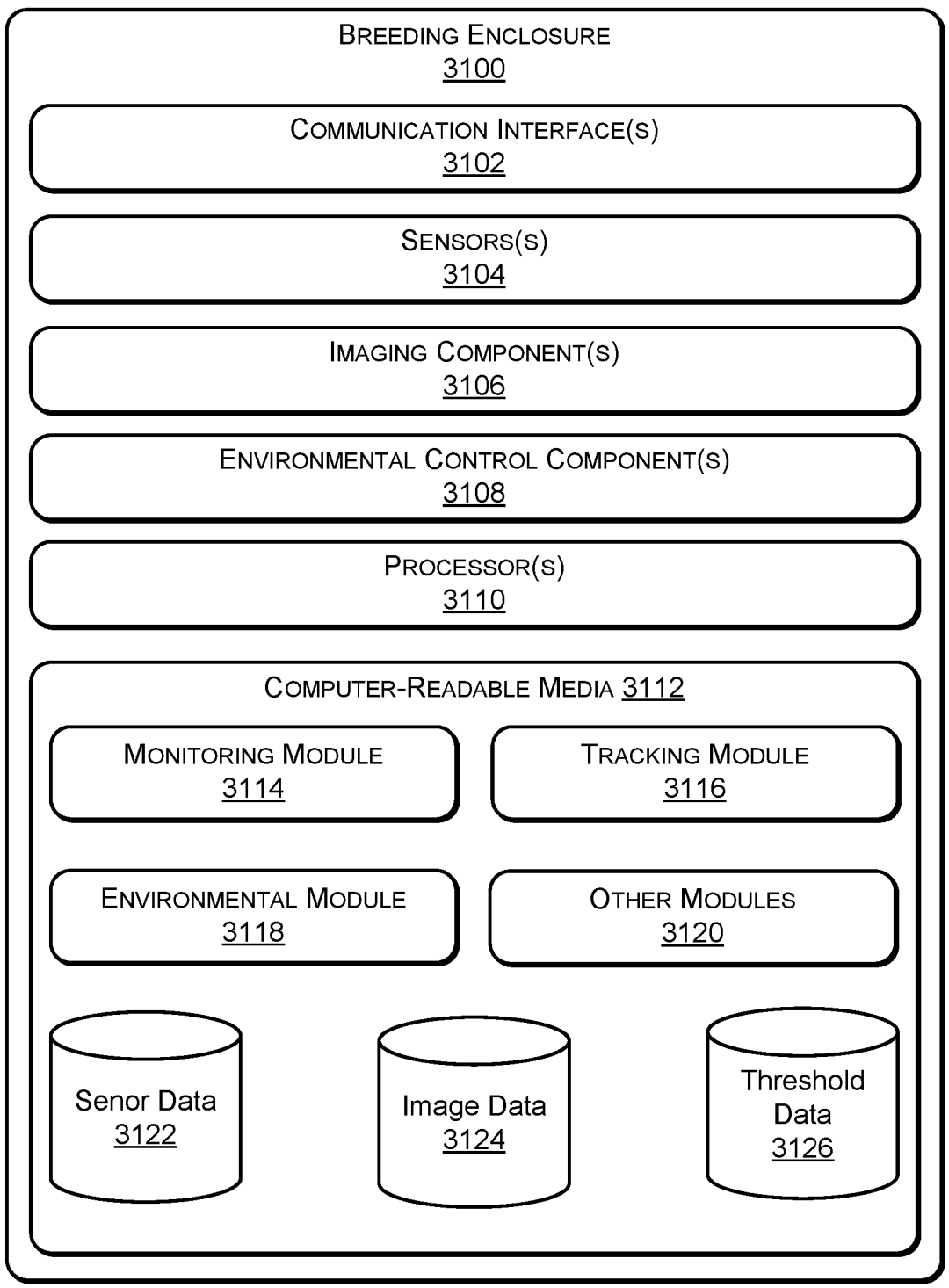
FIG. 31 illustrates example components of the breeding enclosure according to some implementations.

FIG. 31 illustrates example components of a breeding enclosure 3100 according to some implementations. As described above, the breeding enclosure 3100 may be a self-contained unit for monitoring egg density within a given amount of medium and/or tracking egg bearing females during the egg laying process. In this manner, the breeding enclosure 3100 may be able to determine when the medium should be moved or transported to an incubation enclosure.

In the illustrated example, the breeding enclosure 3100 includes one or more communication interfaces 3102. The communication interfaces 3102 are configured to facilitate communication between one or more networks and/or other devices of the cultivation system described herein. For instance, the communication interfaces 3102 may provide a notification to a conveyor or robotic arm that may move the egg bearing medium into an incubation enclosure or the breeding enclosure 3100 into an incubation area (for example, when the incubation enclosure and the breeding enclosures are the same). In some cases, the communication interfaces 3102 may also facilitate communication between one or more wireless access points, a master device, and/or one or more other computing devices as part of an ad-hoc or home network system. The communication interfaces 3102 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 3102 may also enable device to device communication such as between breeding enclosure 3100 and one or more printers and/or one or more other electronic devices in proximity to the breeding enclosure 3100 to provide information to a system operator or manager.

The breeding enclosure 3100 may also include various sensors 3104 that may collect sensor data that is usable to determine an egg density within the breeding enclosure 3100 or within a predetermine amount of medium. For example, the breeding enclosure 3100 may include light, optical, or photo sensors, mechanical sensors (e.g., pressure, force, or motion sensors), electrical sensors (capacitive, resistive, current, or potential based sensors), weight sensors, thermal or heat sensors, among others.

In some cases, a plurality of imaging component 3106 may be used to monitor the insects within the breeding enclosure 3100. For example, the breeding enclosure 3100 may include a three-dimensional camera, an infrared camera, and/or a red-green-blue camera. In one example, the three-dimensional and infrared camera may be configured to capture information related to depths, location, and movement of objects within the field of view. The red-green-blue camera may be configured to detect edges of objects by identifying changes in color within the field of view. In some cases, the breeding enclosure 3100 may also include additional imaging components for tracking the movement of insects within the breeding enclosure 3100. For example, the breeding enclosure 3100 may include one or more motion sensors or thermal sensors.

The breeding enclosure 3100 may also include one or more environmental control components 3108. The environmental control components 3108 may be utilized to control environmental factors, such as airflow, temperature, humidity, salinity, etc. within the breeding enclosure 3100 to encourage or discourage reproductive behavior or the production of eggs.

The breeding enclosure 3100 includes one or more processors 3110, such as at least one or more access components, control logic circuits, central processing units, or processors, as well as one or more computer-readable media 3112 to perform the function of the breeding enclosure 3100. Additionally, each of the processors 3110 may itself comprise one or more processors or processing cores.

Depending on the configuration, the computer-readable media 3112 may be an example of tangible non-transitory computer storage media and may include volatile and non-volatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 3110.

Several modules such as instruction, data stores, and so forth may be stored within the computer-readable media 3112 and configured to execute on the processors 3110. For example, as illustrated, the computer-readable media 3112 stores a monitoring module 3114, a tracking module 3116, an environmental module 3118 as well as other modules 3120. The computer-readable media 3112 may also be configured to store data, such as sensor data 3122 collected by the sensors 3104, image data 3124 captured by the camera components 3106, and threshold data 3126 such as various desired egg densities or range of densities.

The monitoring module 3114 may be configured to analyze the sensor data 3122 and the image data 3124 and to determine an egg density or egg to medium ratio, or an amount of eggs being laid. For example, the monitoring module 3118 may be configured to determine a rate of egg laying, determine that one or more thresholds (such as an egg density threshold) have been achieved, and to cause the communication interfaces 3102 to alert another system such as a robotic arm that the threshold has been meet to further cause the robotic arm to collect and move the egg bearing medium or the habitat into an incubation enclosure.

The tracking module 3116 may be configured to track the movement of egg laying females within the enclosures 3100 and to identify egg laying events using the sensor data 3122 and the image data 3124. And to again cause the communication interfaces 3102 to alert another system such as a robotic arm when the tracking module 3116 determines that a threshold number of eggs has been laid to further cause the robotic arm to collect and move the egg bearing medium or the habitat into an incubation enclosure.

The environmental module 3118 may be configured to analyze the data provided by the monitoring module 3114 and the tracking module 3116 and to determine an environmental adjustment based on the data. For example, if a desired egg density is not being achieved, the environmental module 3118 may adjust the environment control components 3108 to a more suitable environment for laying eggs to encourage increased egg laying.

Figure 32:
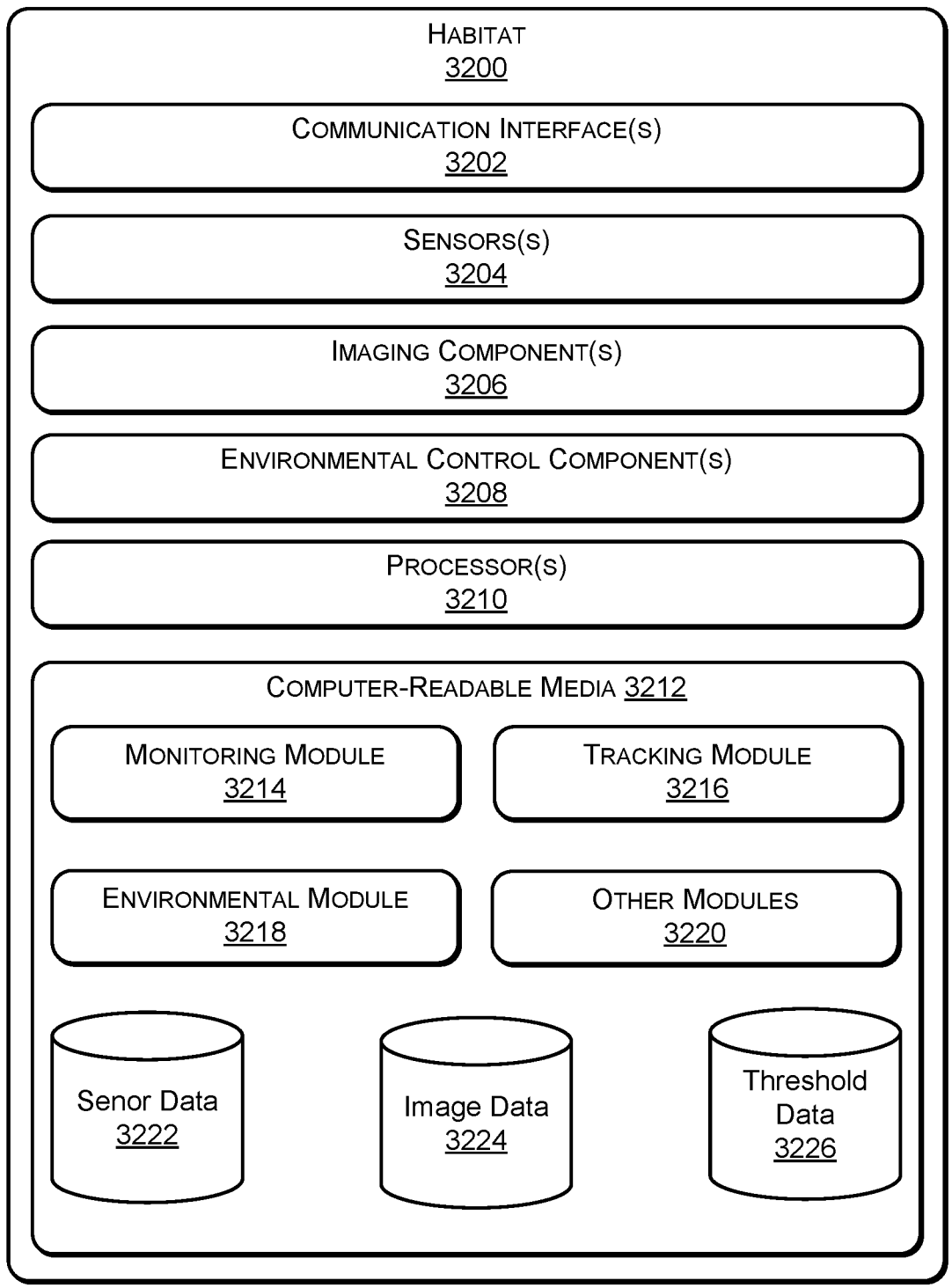
FIG. 32 illustrates example components of a habitat according to some implementations.

FIG. 32 illustrates example components of a habitat 3200 according to some implementations. As described above with respect to FIGS. 1-30 and below with respect to FIGS. 36-44, the habitat 3200 may be a self-contained unit for cultivating insects. In some cases, the habitat 3200 may be configured to monitor the insects within the habitat 3200 to determine, for example, when the insects should be harvested.

In the illustrated example, the habitat 3200 includes one or more communication interfaces 3202. The communication interfaces 3202 are configured to facilitate communication between one or more networks and/or other devices of the cultivation system described herein. For instance, the communication interfaces 3202 may provide a notification when the insects are ready to harvest, food levels are low, water levels are low etc. In some cases, the communication interfaces 3202 may also facilitate communication between one or more wireless access points, a master device, and/or one or more other computing devices as part of an ad-hoc or home network system. The communication interfaces 3202 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 3202 may also enable device to device communication such as between habitat 3200 and one or more printers and/or one or more other electronic devices in proximity to the habitat 3200 to provide information to a system operator or manager.

The habitat 3200 may also include various sensors 3204 that may collect sensor data that is usable to determine a population, health, insect size, food levels, water levels, etc.

within the habitat 3200. For example, the habitat 3200 may include light, optical, or photo sensors, mechanical sensors (e.g., pressure, force, or motion sensors), electrical sensors (capacitive, resistive, current, or potential based sensors), weight sensors, thermal or heat sensors, among others.

In some cases, a plurality of imaging component 3206 may be used to monitor the insects within the habitat 3200. For example, the habitat 3200 may include a three-dimensional camera, an infrared camera, and/or a red-green-blue camera. In one example, the three-dimensional and infrared camera may be configured to capture information related to depths, location, and movement of objects within the field of view. The red-green-blue camera may be configured to detect edges of objects by identifying changes in color within the field of view. In some cases, the habitat 3200 may also include additional imaging components for tracking the movement of insects within the habitat 3200. For example, the habitat 3200 may include one or more motion sensors or thermal sensors.

The habitat 3200 may also include one or more environmental control components 3208. The environmental control components 3208 may be utilized to control environmental factors, such as wind, temperatures, humidity, salinity, etc. within the habitat 3200 to encourage proper growth based on life stages and desired crop output.

The habitat 3200 includes one or more processors 3210, such as at least one or more access components, control logic circuits, central processing units, or processors, as well as one or more computer-readable media 3212 to perform the function of the habitat 3200. Additionally, each of the processors 3210 may itself comprise one or more processors or processing cores.

Depending on the configuration, the computer-readable media 3212 may be an example of tangible non-transitory computer storage media and may include volatile and non-volatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 3210.

Several modules such as instruction, data stores, and so forth may be stored within the computer-readable media 3212 and configured to execute on the processors 3210. For example, as illustrated, the computer-readable media 3212 stores a monitoring module 3214, a tracking module 3116, an environmental module 3118 as well as other modules 3220. The computer-readable media 3212 may also be configured to store data, such as sensor data 3122 collected by the sensors 3204, image data 3224 captured by the camera components 3206, and threshold data 3226 such as various desired egg densities or range of densities.

The monitoring module 3214 may be configured to analyze the sensor data 3222 and the image data 3224 and to determine insect size, health, age, movement, activity level, etc. For example, the monitoring module 3218 may be configured to determine when the insects have reached an appropriate size for harvesting and to cause the communication interfaces 3202 to alert another system such as a robotic arm that the threshold has been meet to further cause the robotic arm to collect and move the insects to a waste removal and/or processing area.

The tracking module 3216 may be configured to track the movement of insects within the habitat 3200 based on the sensor data 3222 and the image data 3224. And to again cause the communication interfaces 3202 to alert another system such as a robotic arm when the tracking module 3216 determines that a threshold insect size has been reached.

The environmental module 3218 may be configured to analyze the data provided by the monitoring module 3214 and the tracking module 3216 and to determine an environmental adjustment based on the data. For example, the environmental module 3218 may adjust the environment control components 3208 to a more suitable environment for raising the insects or to encourage certain behavior such as increased shedding of the chitin or exoskeleton.

Figure 33:
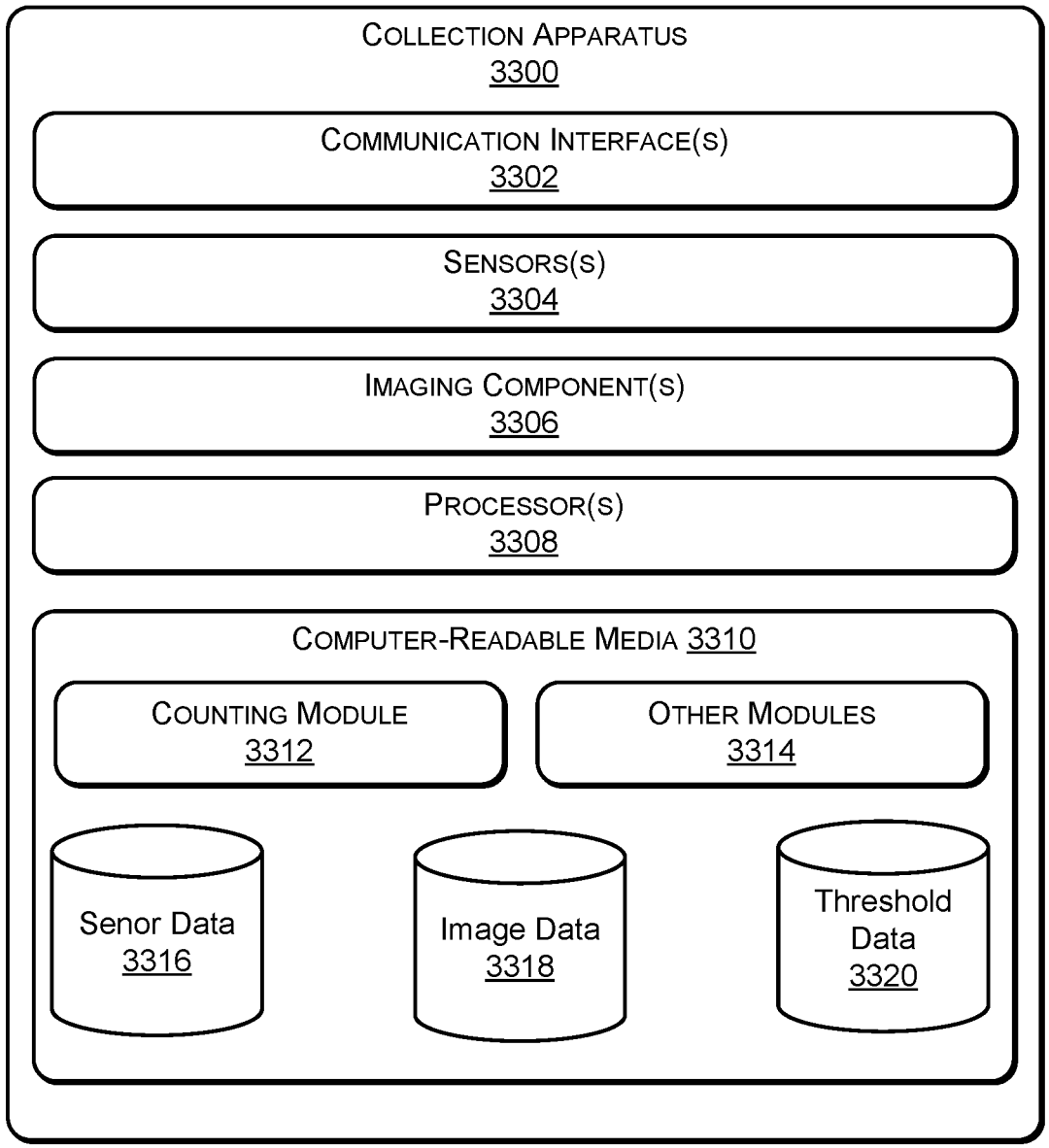
FIG. 33 illustrates example components of a collection apparatus according to some implementations.

FIG. 33 illustrates example components of a collection apparatus 3300 according to some implementations. As described above in FIGS. 2-30, the collection apparatus 3300 may be a collection bin or collection tube that may be used to group eggs or newly hatched insects for placement in a habitat or to count or weigh insects prior to final processing. For example, the collection apparatus 3300 may be one or more of devices 200, 300, 400, and/or 600 as well as systems 900, 1200, 1300, 1700, 1900, 200, 2200, 2400, 2700, and/or 2800.

In the illustrated example, the collection apparatus 3300 includes one or more communication interfaces 3302. The communication interfaces 3302 are configured to facilitate communication between one or more networks and/or other devices of the cultivation system described herein. For instance, the communication interfaces 3302 may provide a notification when a predetermined number of the insects are collected within the collection apparatus 3300. In some cases, the communication interfaces 3302 may also facilitate communication between one or more wireless access points, a master device, and/or one or more other computing devices as part of an ad-hoc or home network system. The communication interfaces 3302 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 3302 may also enable device to device communication such as between collection apparatus 3300 and one or more printers and/or one or more other electronic devices in proximity to the collection apparatus 3300 to provide information to a system operator or manager.

The collection apparatus 3300 may also include various sensors 3304 that may collect sensor data that is usable to determine a number of insects or weight of insects within the collection apparatus 3300. For example, the collection apparatus 3300 may include light, optical, or photo sensors, mechanical sensors (e.g., pressure, force, or motion sensors), electrical sensors (capacitive, resistive, current, or potential based sensors), weight sensors, thermal or heat sensors, among others.

In some cases, a plurality of imaging component 3306 may be used to count the insects collected within the collection apparatus 3300. For example, the collection apparatus 3300 may include a three-dimensional camera, an infrared camera, and/or a red-green-blue camera. In one example, the three-dimensional and infrared camera may be configured to capture information related to depths, location, and movement of objects within the field of view. The red-green-blue camera may be configured to detect edges of objects by identifying changes in color within the field of view. In some cases, the collection apparatus 3300 may also include additional imaging components for counting insects. For example, the collection apparatus 3300 may include one or more motion sensors or thermal sensors.

The collection apparatus 3300 includes one or more processors 3308, such as at least one or more access components, control logic circuits, central processing units, or processors, as well as one or more computer-readable media 3310 to perform the function of the collection apparatus 3300. Additionally, each of the processors 3308 may itself comprise one or more processors or processing cores.

Depending on the configuration, the computer-readable media 3310 may be an example of tangible non-transitory computer storage media and may include volatile and non-volatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 3308.

Several modules such as instruction, data stores, and so forth may be stored within the computer-readable media 3310 and configured to execute on the processors 3308. For example, as illustrated, the computer-readable media 3310 stores a counting module 3312 to determine a number of insects collected within the collection apparatus 3300, as well as other modules 3314. The computer-readable media 3310 may also be configured to store data, such as sensor data 3316 collected by the sensors 3304, image data 3318 captured by the camera components 3306, and threshold data 3320 that may be available to the counting module 3312.

Figure 34:
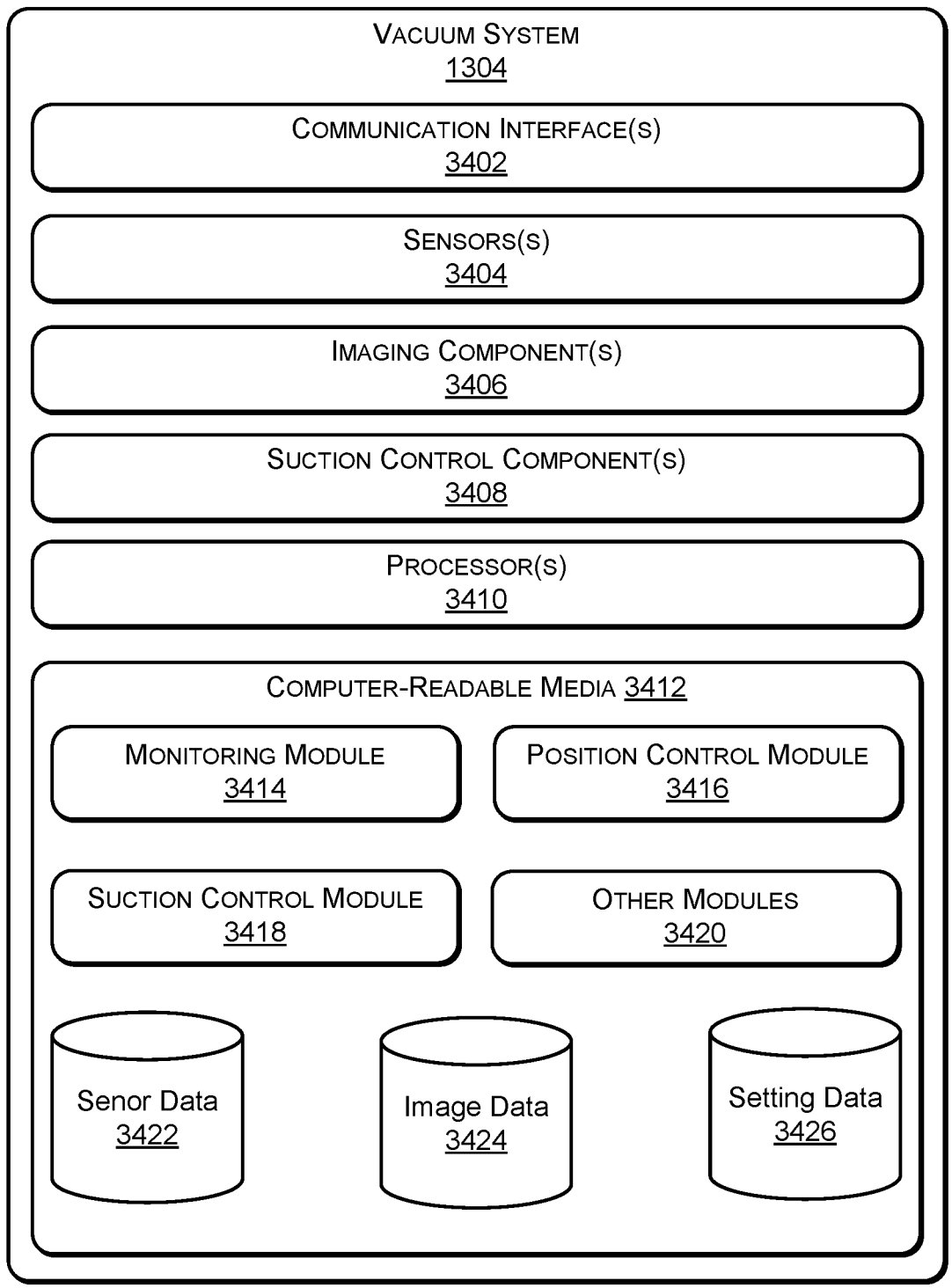
FIG. 34 illustrates example components of the vacuum system of FIG. 13 according to some implementations.

FIG. 34 illustrates example components of a vacuum system 1304 of FIG. 13 according to some implementations. For example, in various systems described herein a vacuum system 1304 may be utilized to remove the insects from the habitats prior to final processing.

In the illustrated example, the vacuum system 1304 includes one or more communication interfaces 3402. The communication interfaces 3402 are configured to facilitate communication between one or more networks and/or other devices of the waste separation systems described herein. For instance, the communication interfaces 3402 may communicate with a habitat, such as habitat 3200 of FIG. 32 to remove the insects from the habitat. In some cases, the communication interfaces 3402 may also facilitate communication between one or more wireless access points, a master device, and/or one or more other computing devices as part of an ad-hoc or home network system. The communication interfaces 3402 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 3402 may also enable device to device communication such as between and one or more printers and/or one or more other electronic devices in proximity to the vacuum system 1304 to provide information to a system operator or manager.

The vacuum system 1304 may also include various sensors 3404 that may collect sensor data that is usable to determine for example a number of insects remaining in a habitat or a number of insects collected by the vacuum system 3400. For example, the vacuum system 1304 may include light, optical, or photo sensors, mechanical sensors (e.g., pressure, force, or motion sensors), electrical sensors (capacitive, resistive, current, or potential based sensors), weight sensors, thermal or heat sensors, among others.

In some cases, a plurality of imaging component 3406 may be used to monitor the insects within a habitat. For example, the vacuum system 1304 may include a three-dimensional camera, an infrared camera, and/or a red-green-blue camera. In one example, the three-dimensional and infrared camera may be configured to capture information related to depths, location, and movement of objects within the field of view. The red-green-blue camera may be configured to detect edges of objects by identifying changes in color within the field of view. In some cases, the vacuum system 1304 may also include additional imaging components for tracking the movement of insects within the habitat. For example, the vacuum system 1304 may include one or more motion sensors or thermal sensors.

The vacuum system 1304 may also include one or more suction control components 3408. The suction control components 3408 may be utilized to control an amount of suction used to remove the insects form the habitats. For example, the suction may be based on a level of waste detected in the habitat, a size of the habitat, size or type of insert within the habitat, etc.

The vacuum system 1304 includes one or more processors 3410, such as at least one or more access components, control logic circuits, central processing units, or processors, as well as one or more computer-readable media 3412 to perform the function of the vacuum system 1304. Additionally, each of the processors 3410 may itself comprise one or more processors or processing cores.

Depending on the configuration, the computer-readable media 3412 may be an example of tangible non-transitory computer storage media and may include volatile and non-volatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 3410.

Several modules such as instruction, data stores, and so forth may be stored within the computer-readable media 3412 and configured to execute on the processors 3410. For example, as illustrated, the computer-readable media 3412 stores a monitoring module 3414, a position control module 3416, a suction control module 3418 as well as other modules 3420. The computer-readable media 3412 may also be configured to store data, such as sensor data 3122 collected by the sensors 3104, image data 3124 captured by the camera components 3106, and threshold data 3126 such as various desired egg densities or range of densities.

The monitoring module 3414 may be configured to analyze the sensor data 3422 and the image data 3424 and to determine a number or percentage of insects remaining within the habitat. For example, the monitoring module 3418 may be configured to determine if the vacuum system 3400 should make another pass over the habitat to remove additional insects.

The position control module 3416 may be configured to align the vacuum with the habitat based on a size of the habitat and/or a type or size of insert within the habitat. In some case, the position control module 3416 may cause the vacuum system 3400 to mate or seal with the habitat prior to removing the insects.

The suction control module 3418 may be configured to analyze the sensor data and image data to determine a level of suction or a depth of suction (how far into the habitat the vacuum system 1304 should remove content at). For example, the suction control module 3418 may control the level of suction to substantially minimize waste collected and substantially maximum the number of insects collected.

Figure 35:
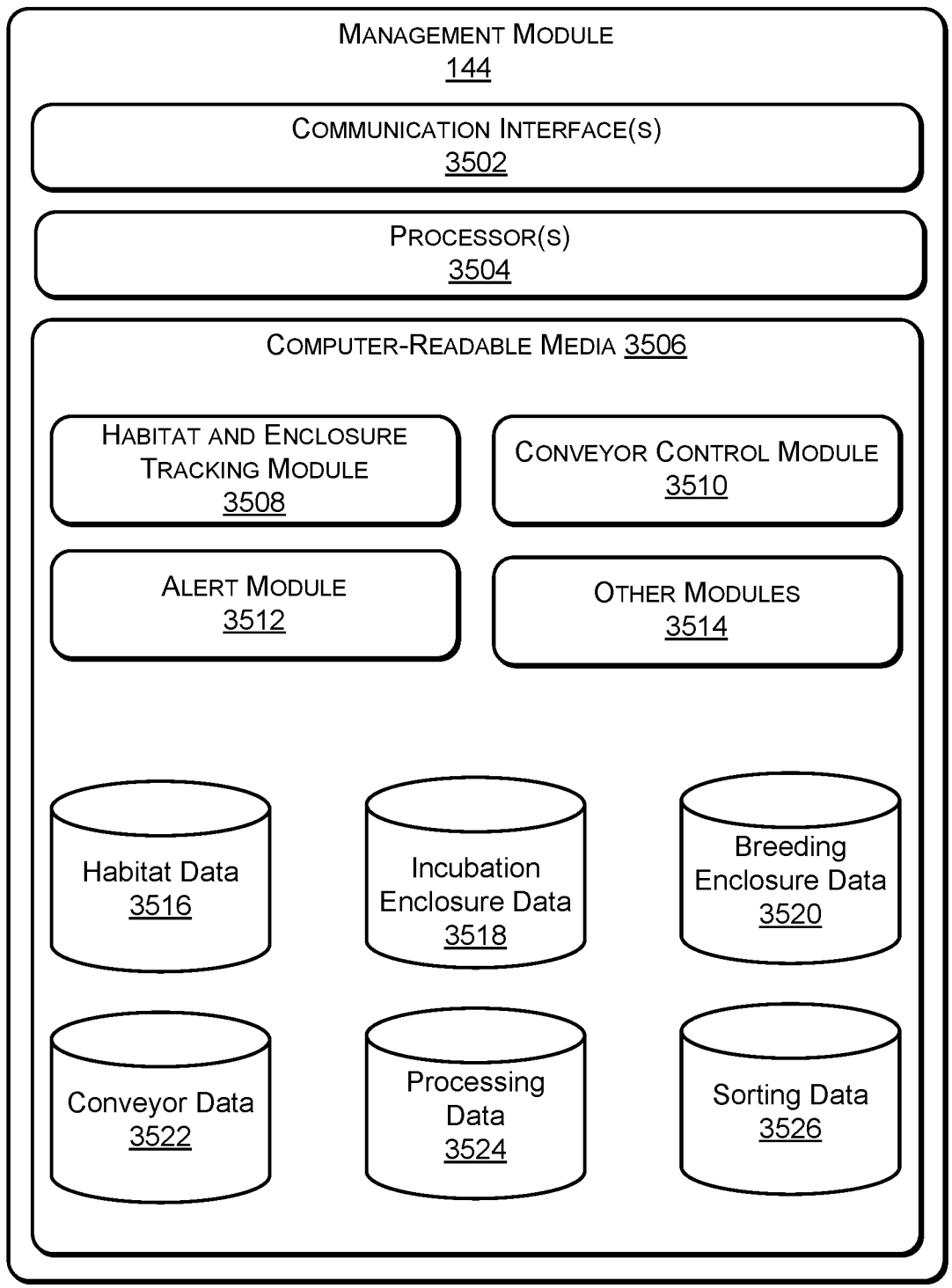
FIG. 35 illustrates example components of the management module of FIG. 1 according to some implementations.

FIG. 35 illustrates example components of a management module 144 of FIG. 1 according to some implementations. For example, the management module 3500 may be configured to control the operations of the insect cultivating and harvesting facility. In some cases, the management module 144 may be one or more servers which may include various types of computing devices and may be owned by a single entity and collocated at a common data center, for example, in proximity to or at the facility or may be located at separate data centers. Alternatively, the servers may be owned and operated by independent entities at separate locations. The servers may be further arranged in any number of ways, such as server farms, stacks, and the like that are commonly used in data centers.

In another example, the management module 144 may be configured to operate as cloud-based services refer to a network accessible platform implemented as a computing infrastructure of processors, storage, software, data access, and so forth that is maintained and accessible via a network such as the Internet. The cloud-based services do not require end-user knowledge of the physical location and configuration of the system that delivers the services. Common expressions associated with cloud services include "on-demand computing," "software as a service (SaaS)," "platform computing," "network accessible platform" and so forth.

In the illustrated example, the management module 144 includes one or more communication interfaces 3502. The communication interfaces 3502 are configured to facilitate communication between one or more networks and/or other devices of the for the cultivation, harvesting, and processing of insects. For instance, the communication interfaces 3502 may communicate with a habitat, such as habitat 3200 of FIG. 32 to monitor the growth of the insects within the habitat. In some cases, the communication interfaces 3502 may also facilitate communication between one or more wireless access points, a master device, and/or one or more other computing devices as part of an ad-hoc or home network system. The communication interfaces 3502 may support both wired and wireless connection to various networks, such as cellular networks, radio, WiFi networks, short-range or near-field networks (e.g., Bluetooth®), infrared signals, local area networks, wide area networks, the Internet, and so forth.

The management module 144 includes one or more processors 3504, such as at least one or more access components, control logic circuits, central processing units, or processors, as well as one or more computer-readable media 3506 to perform the function of the management module 144. Additionally, each of the processors 3504 may itself comprise one or more processors or processing cores.

Depending on the configuration, the computer-readable media 3506 may be an example of tangible non-transitory computer storage media and may include volatile and nonvolatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 3504.

Several modules such as instruction, data stores, and so forth may be stored within the computer-readable media 3506 and configured to execute on the processors 3504. For example, as illustrated, the computer-readable media 3506 stores a habitat and enclosure tracking module 3508, a conveyor control module 3510, an alert module 3512 as well as other modules 3514. The computer-readable media 3506 may also be configured to store data, such as habitat data 3516 associated with the habitats, incubation enclosure data 3518 associated with the incubation enclosures, breeding enclosure data 3520 associated with the breeding enclosures, conveyor data 3522 associated with the conveyors, processing data 3524 associated with the insect processing, and sorting data 3526 associated with the sorting, collecting, and counting of the eggs, newly hatched insects, insects and insect parts (such as the limbs, heads, and abdomens).

The habitat and enclosure tracking module 3508 may receive data and/or communication from the various conveyors, habitats, enclosures, or systems mounted within the facility to track the movement of the habitats and enclosures within the facility.

The a conveyor control module 3510 may, based on the data received, issue command to various conveyors to move a habitat or enclosure from one area to another, for example, from a cultivating area to a waste removal area.

The alert module 3512 may be configured to provide an alert to a facility administrator if the management module 144 determines there is an issue with one or more of the habitats or enclosures based on the data received.

Figure 36:
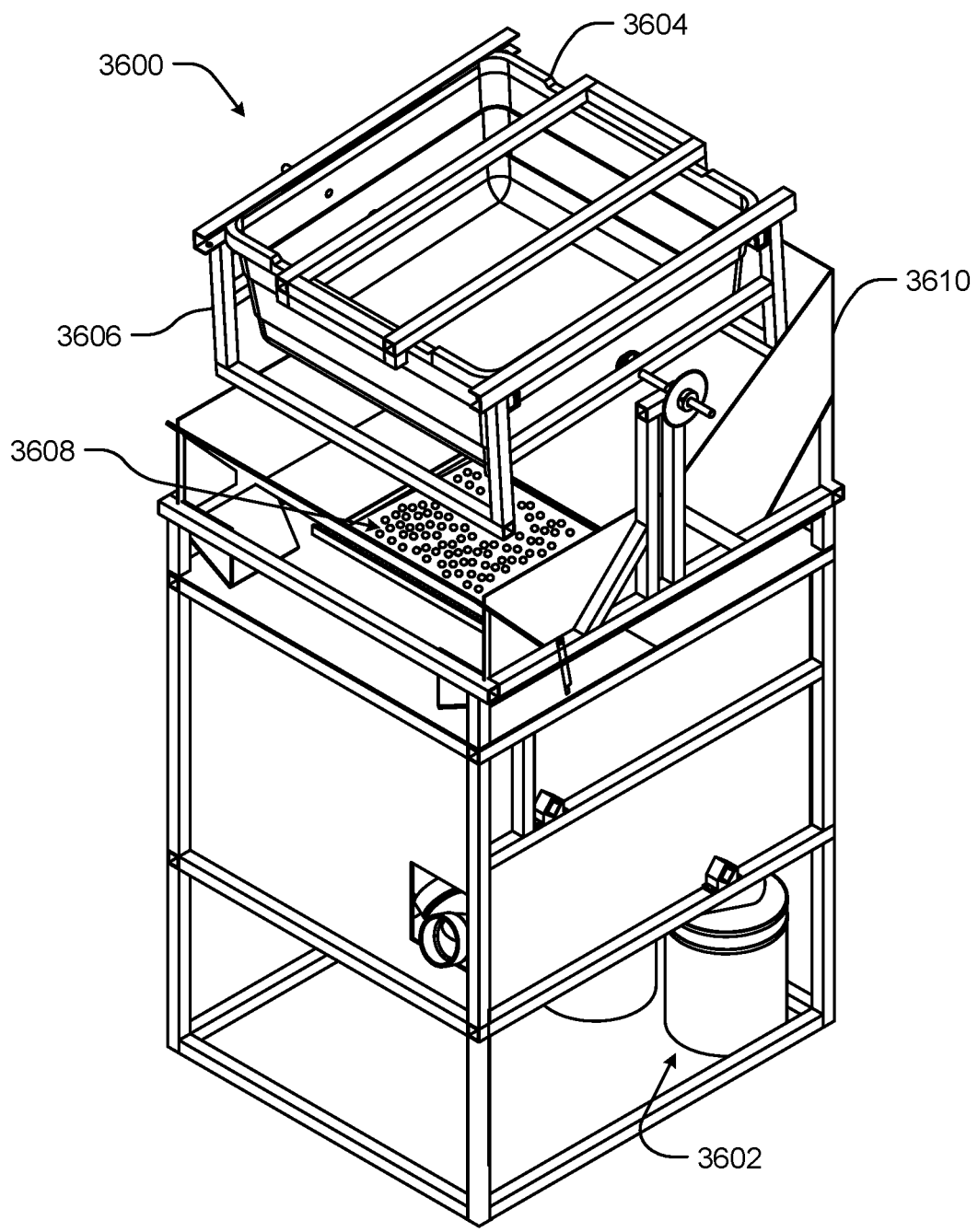
FIG. 36 illustrates an example harvester for use in the waste separation area of FIG. 1 according to some implementations.

FIG. 36 illustrates an example harvester 3600 for use in the waste separation area of FIG. 1 according to some implementations. In the current example, rather than removing insects from the habitat the insects may be separated into the collection bins 3602 by the harvesting system 3600. For example, a habitat, such as habitat 3604, may be placed or otherwise moved into a habitat flipping device 3606 from a rack or habitat transportation system. In general, the habitat flipping device 3606 may be configured to lock or otherwise engage with the habitat 3604, such that when the habitat flipping device 3606 is rotated about an axis by 180°, the habitat 3604 remains within the habitat flipping device 3606 and the contents (e.g., the waste and the live insects) are deposited into the harvesting system 3600.

In one example, the waste and the insects may be deposited onto a screen or mesh 3608 as the habitat 3602 is rotated by 180° within the habitat flipping device 3606. In the illustrated example, the harvesting system 3600 may include a shield 3610 to catch any waste or insects that would otherwise miss the screen 3608 as the habitat 3604 is rotated (e.g., insects dislodged prior to reaching the 180° or upside down position).

In this example, some of the waste will pass through the screen 3608 into a waste container or waste collection bin, such as bin 3602. The holes of the screen 3608 may be sized such that the live insects are maintained on top of the screen 3608 (e.g., the live insects are too large to pass through the screen 3608). In the current example, one or more shoots or ramps (not shown) may be positioned adjacent to the screen 3608. In some cases, the insects may be allowed to migrate towards the edges of the screen 3608 and to drop down the shoots into the collection bin 3602. In other cases, the screen 3608 may be configured to vibrate such that the live insects are encouraged or forced towards the edge of the screen 3608 and down the shoots and into the collection bin 3602.

Once the live insects have been migrated to the shoots adjacent to the screen 3608 or sufficient time (e.g., a predetermined period of time) has passed, the screen 3608 may be tilted to remove the remaining waste. For instance, dead insects may be maintained on the screen as if the holes were sized such that the dead insets passed then the live insects may also pass into the waste containers. Thus, the screen 3608 may be tilted to allow the remaining waste to be moved by gravity to a lower shoot below the live insect shoots, which may deposited the remaining waste into a waste container.

In one specific example, the waste may be configured to pass through the screen 3608, the live insects may be configured to fall or be force down a live insects collection shoot, leaving the dead insects on the screen 3608. In this example, the screen 3608 may tilt to deposit the dead insects into a third collection bin different from the original waste bin feed by the waste passing through the screen 3608. The third bin may be used to collect the dead insets as in some cases, such as with crickets, the exoskeleton or chitin may be collected for uses other than human consumption. Thus, it may be beneficial to collect the live insects, dead insects and waste in separate containers or bins.

Figure 37:
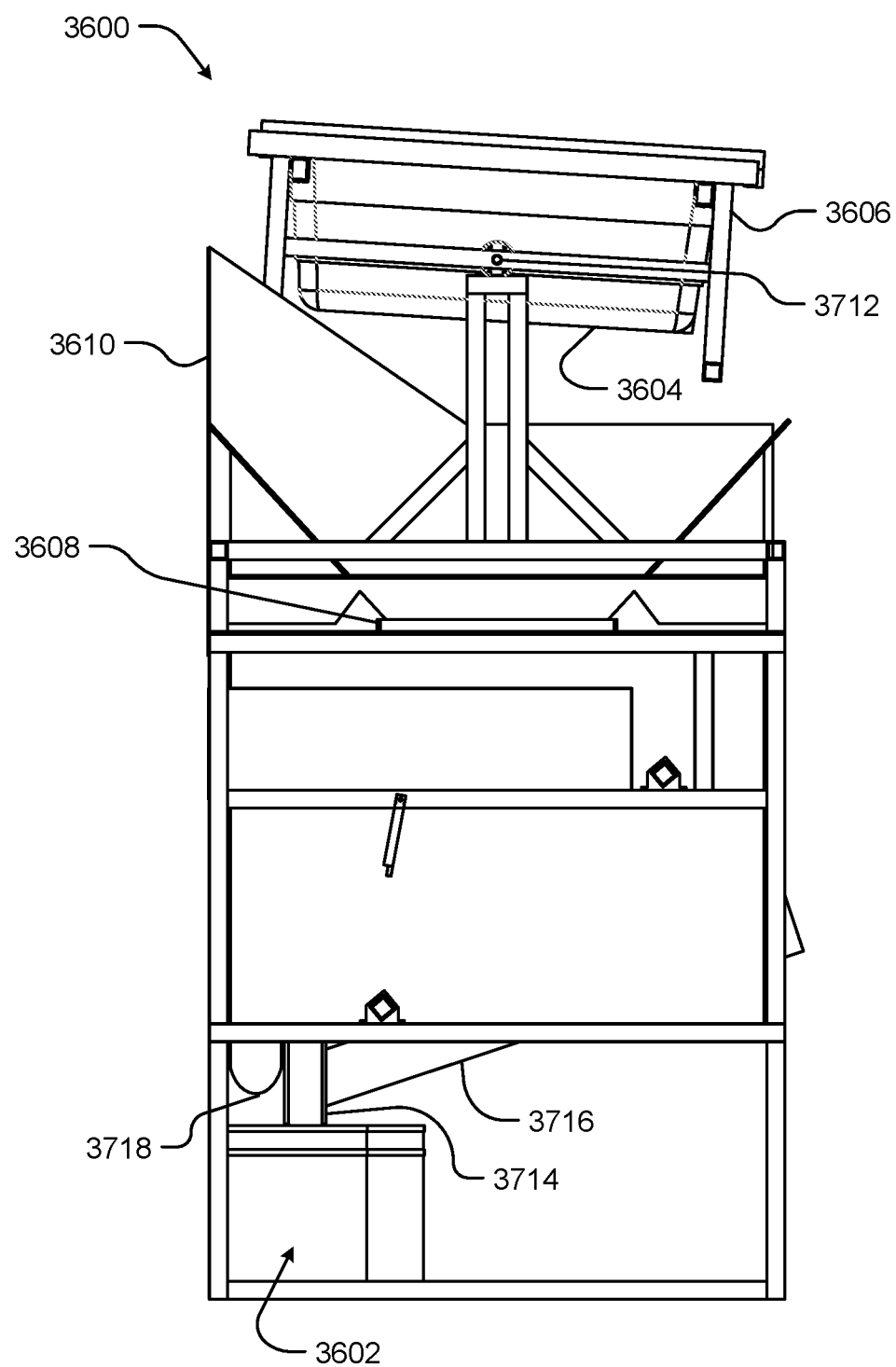
FIG. 37 illustrates the example of the harvester system of FIG. 36 for use in the waste separation area of FIG. 1 according to some implementations.

FIG. 37 illustrates the example system 3600 for use in the waste separation area 126 according to some implementations. In the current example, rather than removing insects from the habitat the insects may be separated into the collection bins 3602 by the harvesting system 3600. For example, a habitat, such as habitat 3604, may be positioned or otherwise moved into a habitat flipping device 3606 from a rack or habitat transportation system. In general, the habitat flipping device 3606 may be configured to lock or otherwise engage with the habitat 3604, such that when the habitat flipping device 3606 is rotated about an axis, generally indicated by 3712, by 180°, the habitat 3604 remains within the habitat flipping device 3606 and the contents (e.g., the waste and the live insects) are deposited into the harvesting system 3600.

In one example, the waste and the insects may be deposited onto a screen or mesh 3608 as the habitat 3604 is rotated by 180° within the habitat flipping device 3606. In the illustrated example, the harvesting system 3600 may include a shield 3610 to catch any waste or insects that would otherwise miss the screen 3608 as the habitat 3604 is rotated about the axis 3712 (e.g., insects dislodged prior to reaching the 180° or upside down position).

In this example, some of the waste will pass through the screen 3608 into a shoot 3714 that deposits the waste in a waste container or waste collection bin, such as bin 3602. The holes of the screen (not shown) may be sized such that the live insects are maintained on top of the screen (e.g., the live insects are too large to pass through the screen). In the current example, one or more shoots or ramps 3716 may be positioned adjacent to the screen. In some cases, the insects may be allowed to migrate towards the edges of the screen and to drop down the shoots into the collection bin 3602. In other cases, the screen may be configured to vibrate, change temperature, emit sounds, or otherwise encourage, scare, or force the live insects towards the edge of the screen 3708 and down the shoots and into the collection bin 3602.

Once the live insects have been migrated to the shoots adjacent to the screen or sufficient time (e.g., a predetermined period of time) has passed, the screen may be tilted to remove the remaining waste. For instance, dead insects may be maintained on the screen as if the holes were sized such that the dead insets passed then the live insects may also pass into a third shoot 3718 and deposited in a third container or bin 3602. Thus, the screen may be tilted to allow the remaining waste to be moved by gravity to the third shoot 3718 lower or below the live insect shoots 3716, which may deposited the remaining waste into a container.

Figure 38:
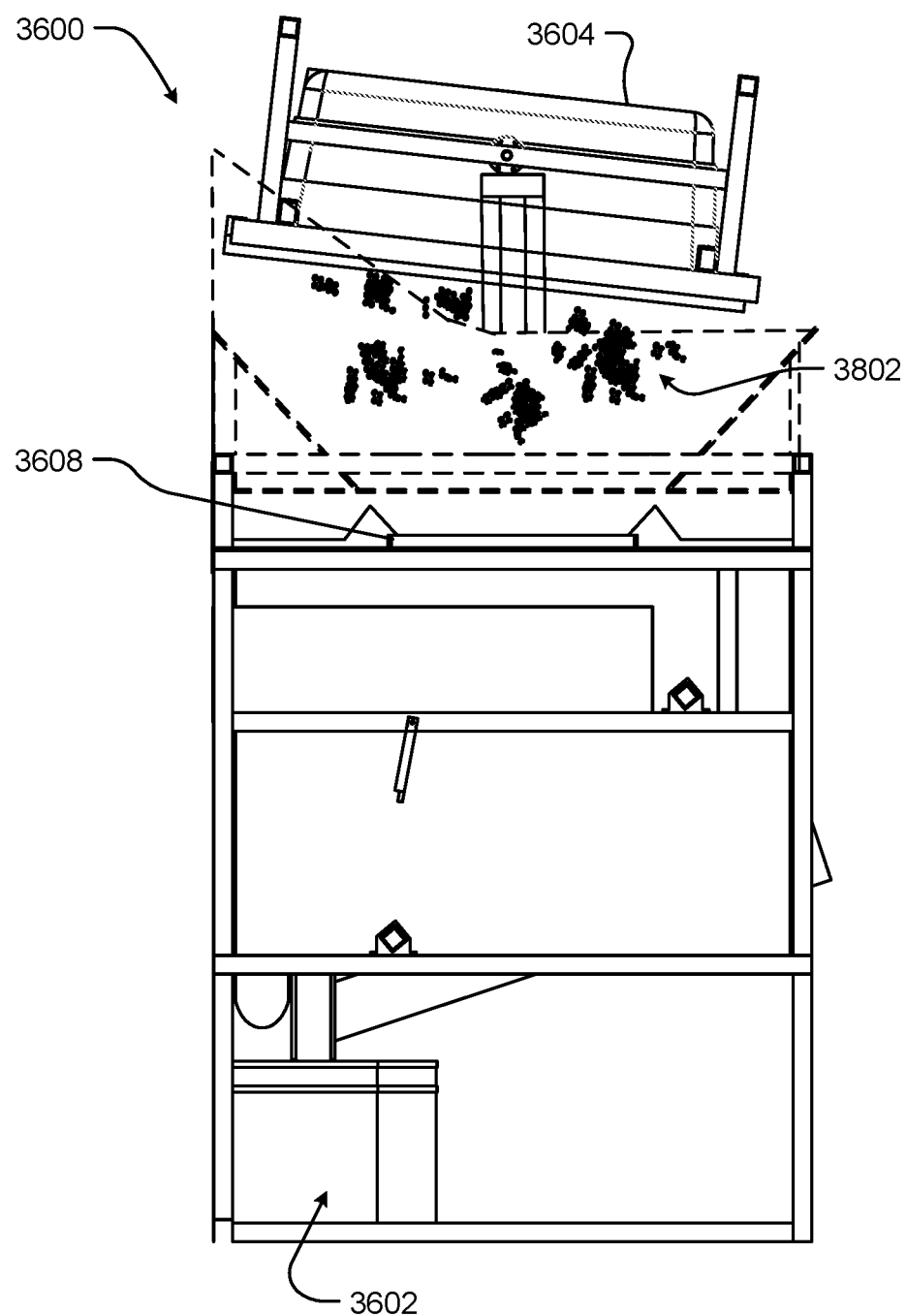
FIG. 38 illustrates the example of the harvester system of FIG. 36 in the process of depositing the contents of the habitat onto the screen according to some implementations.

FIG. 38 illustrates the example of the system 3600 of FIG. 36 in the process of depositing the contents 3802 of the habitat 3604 onto the screen 3608 according to some implementations. In the illustrated example, the contents 3802 may include waste, live insets, and dead insects as discussed above. As the contents 3802 are deposited onto the screen some of the contents such as the waste falls through the holes of the screen 3608 and into a waste collection bin 3602(2). The dead insets and live insects may be maintained on top of the screen 3608. The live insects may then migrate either voluntarily over time or by applying a stimulus, such as vibration, sound, food or water, noise, etc. to either the screen or at the desired migration area (e.g., the shoots). Once the live insects have moved over to the shoots (e.g., off the screen 3608) and are collected in a live insect collection bin 3602, the screen 3608 may change positions or tilt to cause the remaining dead insets as well as any remaining waste to fall into an additional shoot for collection in a dead insect collection bin. By separating the waste, live insects, and the dead insects, the waste may be discarded, the live insects may be processed for use in foot products, and the dead insects may be processed for mineral or material value (e.g., chitin collection).

Figure 39:
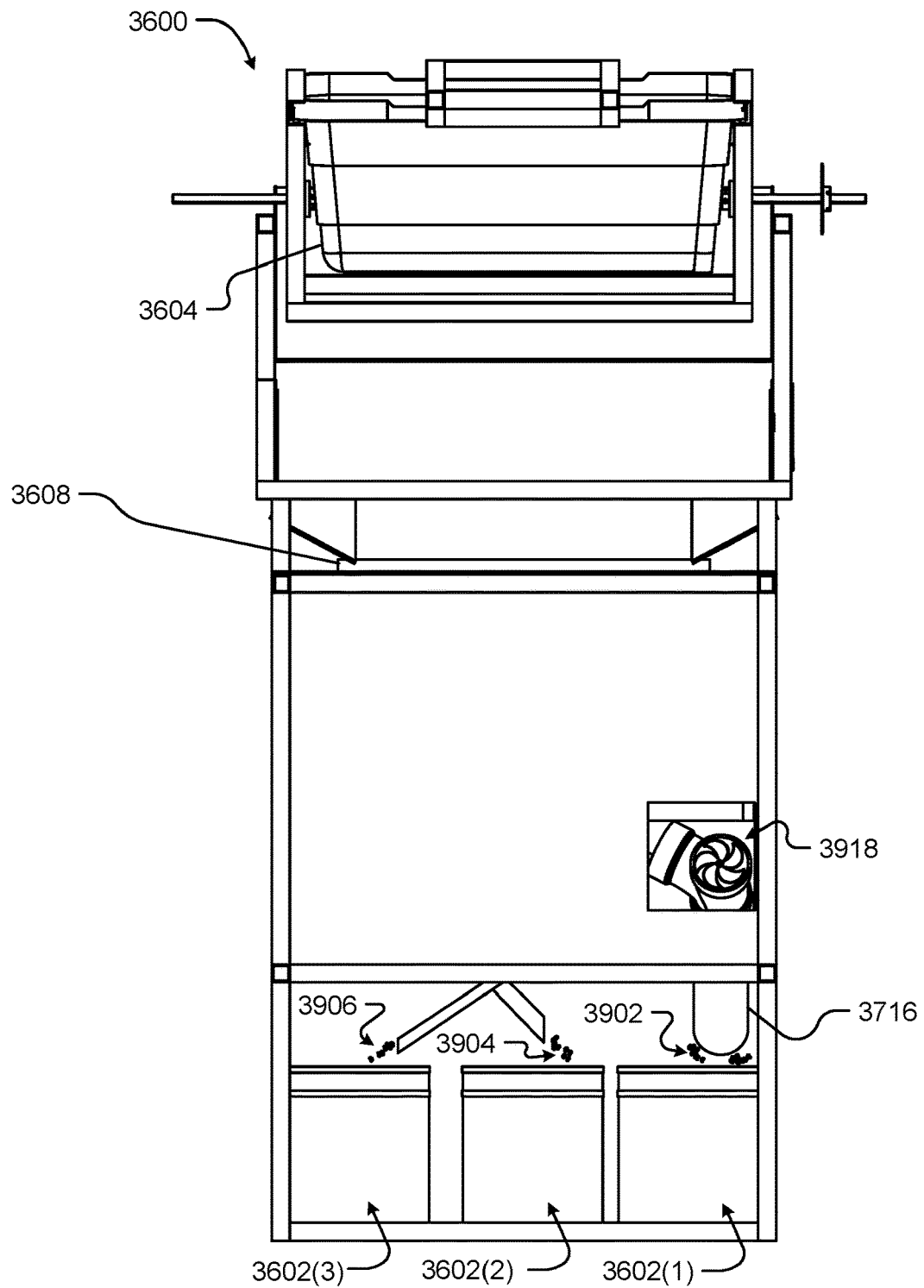
FIG. 39 illustrates the example of the harvester system of FIG. 36 in the process of separating the contents of the habitat into live insect collection bins, dead insect collection bins, and waste collection bins according to some implementations.

FIG. 39 illustrates the example of the system 3600 of FIG. 36 in the process of separating the contents, such as live insects 3902, dead insects 3904, and waste 3906, of a habitat 3604 into live insect collection bins 3602(1), dead insect collection bins 3602(2), and waste collection bins 3602(3) according to some implementations. In the current example, the live insects 3902, dead insects 3904, and waste 3906 are separated, such that the waste 3906 may be discarded, the live insects 3902 may be processed for use in foot products, and the dead insects 3904 may be processed for mineral or material value (e.g., chitin collection) which may be used in other process such as the formation of chitosan.

In some cases, the live insects 3902 may have a tendency to become stuck or to attempt to climb out of the shoot 3716 that delivers the live insects 3902 to the live insect collection bin 3602(1). In this example, a fan 3918 or vibration device to encourage the live insects 3902 to exit the shoot 3716 and ultimately be deposited into the live insect collection bin 3602(1).

Figure 40:
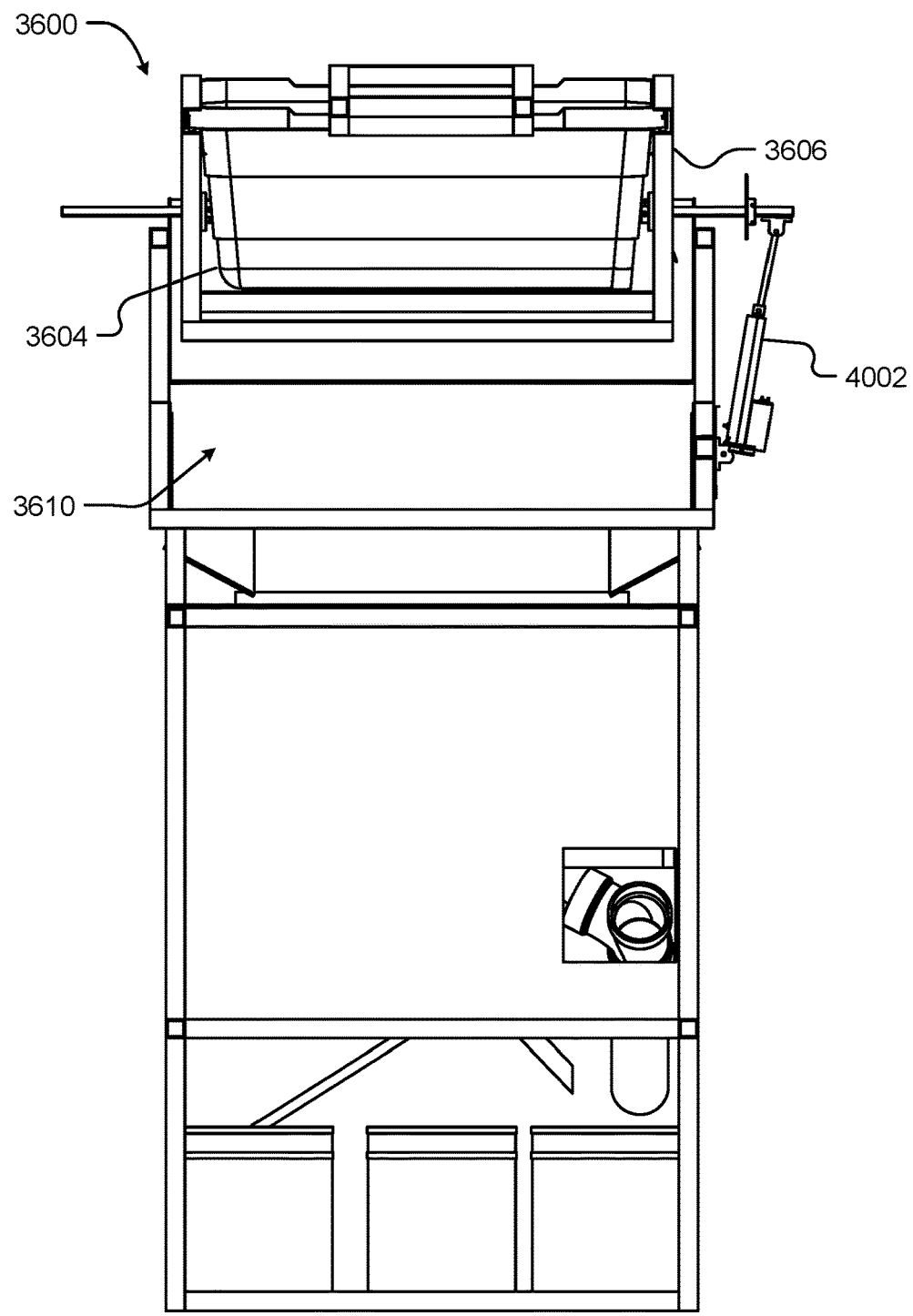
FIG. 40 illustrates the example of the harvester system of FIG. 36 for use in the waste separation area of FIG. 1 according to some implementations.

FIG. 40 illustrates the example system 3600 of FIG. 36 for use in the waste separation area 126 of FIG. 1 according to some implementations. As discussed above, rather than removing insects from the habitat 3604 the insects may be separated into the collection bins by the harvesting system 3600. For example, the habitat 3604, may be placed or otherwise moved into a habitat flipping device 3606 from a rack or habitat transportation system. In the current example, the habitat flipping device 3606 may be coupled to a rotation device 4002. The rotation device 4002 may rotate the habitat flipping device 3606 in response to receiving a signal such as an indication that the habitat 3604 has locked or been secured within the habitat flipping device 3606. The rotation device 4002 may be configured to rotate the habitat 3604 by 180°, such that the contents of the habitat 3604 may be deposited within the harvesting system 3600. Once a predetermined period of time has elapsed, the rotation device 4002 may rotate the habitat 3604 and/or the habitat flipping device 3606 in the reverse direction back to an upright position. In another case the rotation device 4002 may continue to rotate the habitat 3604 and/or the habitat flipping device 3606 in the same direction to bring the habitat 3604 back to an upright position.

In the current example, the rotation device 4002 is positioned on the adjacent to the insect shield 3610, but in other cases the rotation device 4002 may be positioned opposite the insect shield 4008. Further it should be understood, that the illustrated rotation device 4002 is one example, and that the rotation device 4002 may take various forms including belts, screws, locking systems, etc.

Figure 41:
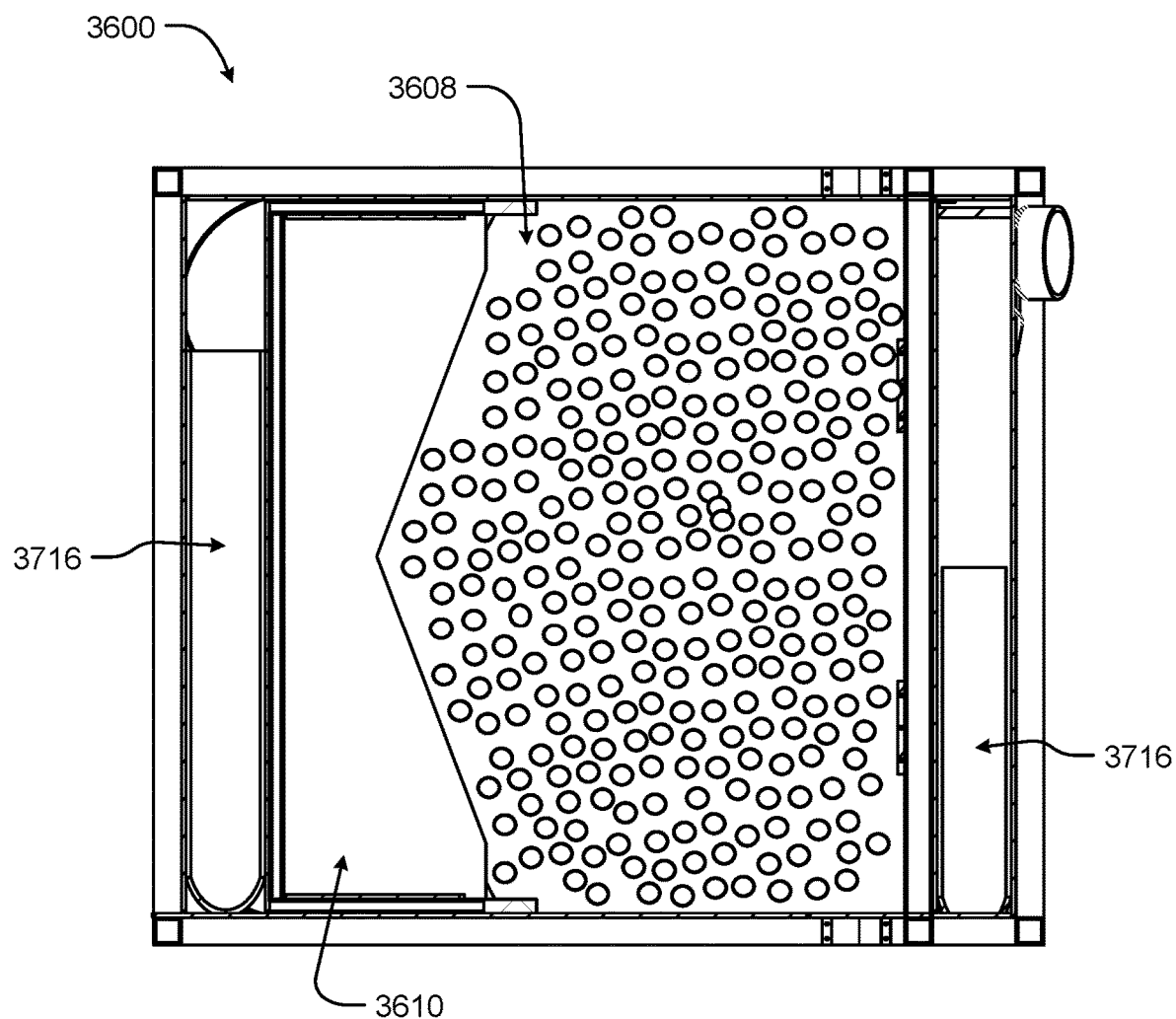
FIG. 41 illustrates a top view of the example of the harvester system of FIG. 36 for use in a waste separation area according to some implementations.

FIG. 41 illustrates a top view of the example system 3600 of FIG. 36 for use in the waste separation area 126 of FIG. 1 according to some implementations. In the current example, the habitat flipping device has been removed, such that a screen 3608, live insect shoots 3716, and an insect shield 3610 are visible. The insect shield 3710 may be an angle or incline to cause the contents of the habitat (not shown) that would otherwise be deposited outside of the harvesting system 3600 or onto the shoot 3716 to fall onto the screen 3608. The screen 3608 includes a plurality of holes or gaps that allow waste to pass but to retain any live insects and, in some case, the dead insects on top. The shoots 3716 are positioned adjacent to the screen 3608 such that the live insects may migrate or move into them over a period of time.

In some cases, the screen 3608 may be configured to vibrate or shake to cause the live insects to flee or attempt to move to more stable ground (e.g., the shoots 3716). In other examples, the harvesting system 3600 may be equipped with one or more speaker, feed dispensing units, water dispensing units, scent releasing units, among other device to encourage the live insects into the shoots 3716. In the current example, the shoots 3716 are arranged adjacent to two sides of the screen 3608, however, in other examples the shoots may be arranged adjacent to any number of sides. For instance, shoots may be arranged adjacent to each of the sides of the screen 3608.

Figure 42:
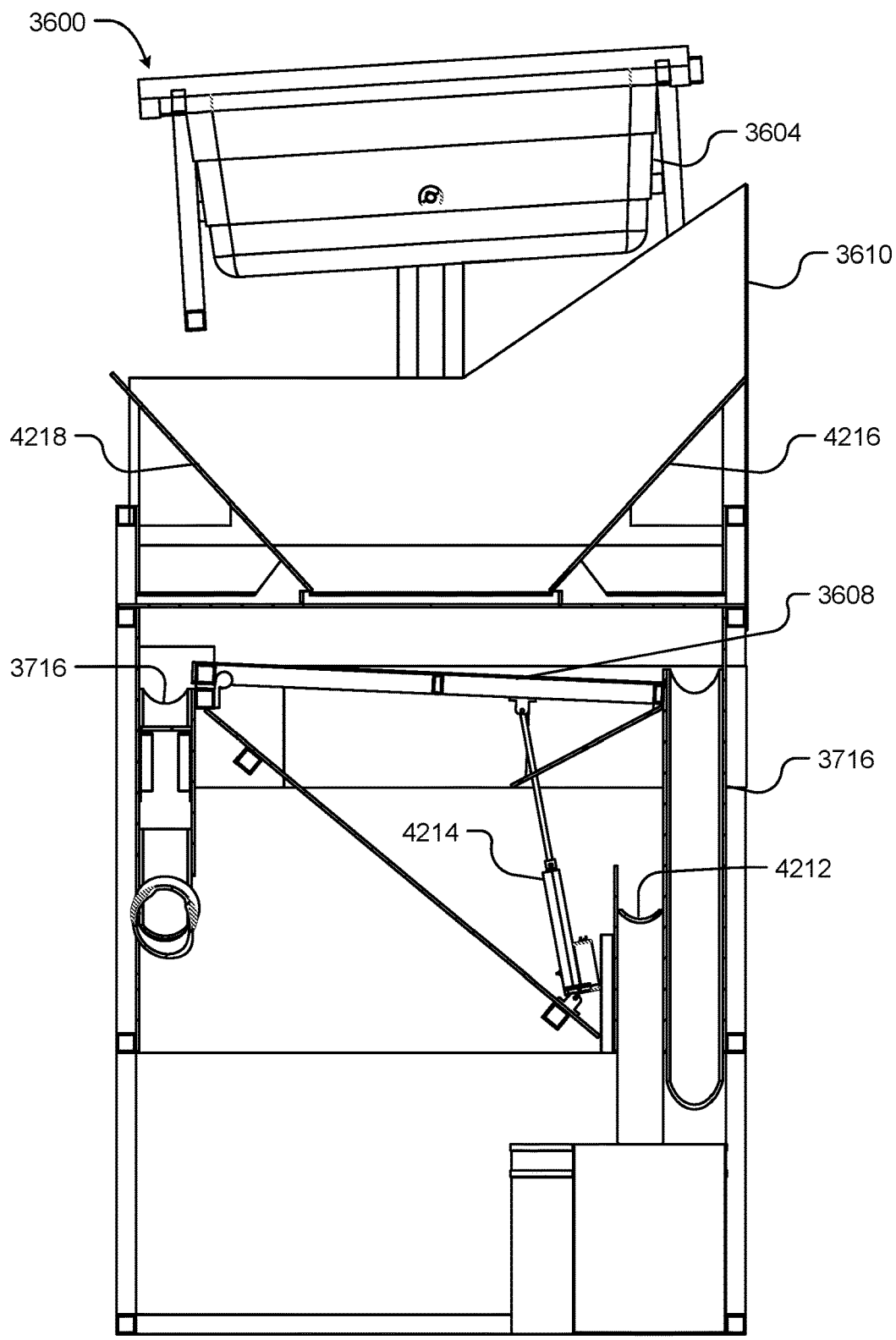
FIG. 42 illustrates a side view of the example of the harvester system of FIG. 36 for use in a waste separation area according to some implementations.

FIG. 42 illustrates a side view of the example system 3600 of FIG. 36 for use in the waste separation area 126 of FIG. 1 according to some implementations. In the illustrated example, the harvesting system 3600 is shown with the side wall removed, such that the internal components are visible. For instance, the screen 4202 is shown below the shield 3610, such that the shield 3610 funnels the contents of the habitat 3604 onto the screen 3608. The live insect collection shoots 3716 are shown adjacent to the screen 3608. In the illustrated example, the live insect collection shoots 3716 are position under overhangs 4216 and 4218 of the shield 3610 to prevent any waste or dead insets from inadvertently being deposited onto the shoots 3716.

The dead insect collection shoot 4212 is positioned at a level below the screen 3608 and the live insect collection shoots 3716. Further, a height controlling unit 4214 may be coupled to or attached to the screen 3608 and the screen 3608 may be configured to tilt or angle in response to the height controlling unit 4214 depressing or lowering on side of the screen 3608, such that the edge of the screen 3608 lowered by the height controlling unit 4214 may mate or align with the edge of the dead insect collection shoot 4212, as illustrated below with respect to FIG. 43. In this manner, the live insects may be separated from the dead insects and both may be separated from the waste within the habitat.

Figure 43:
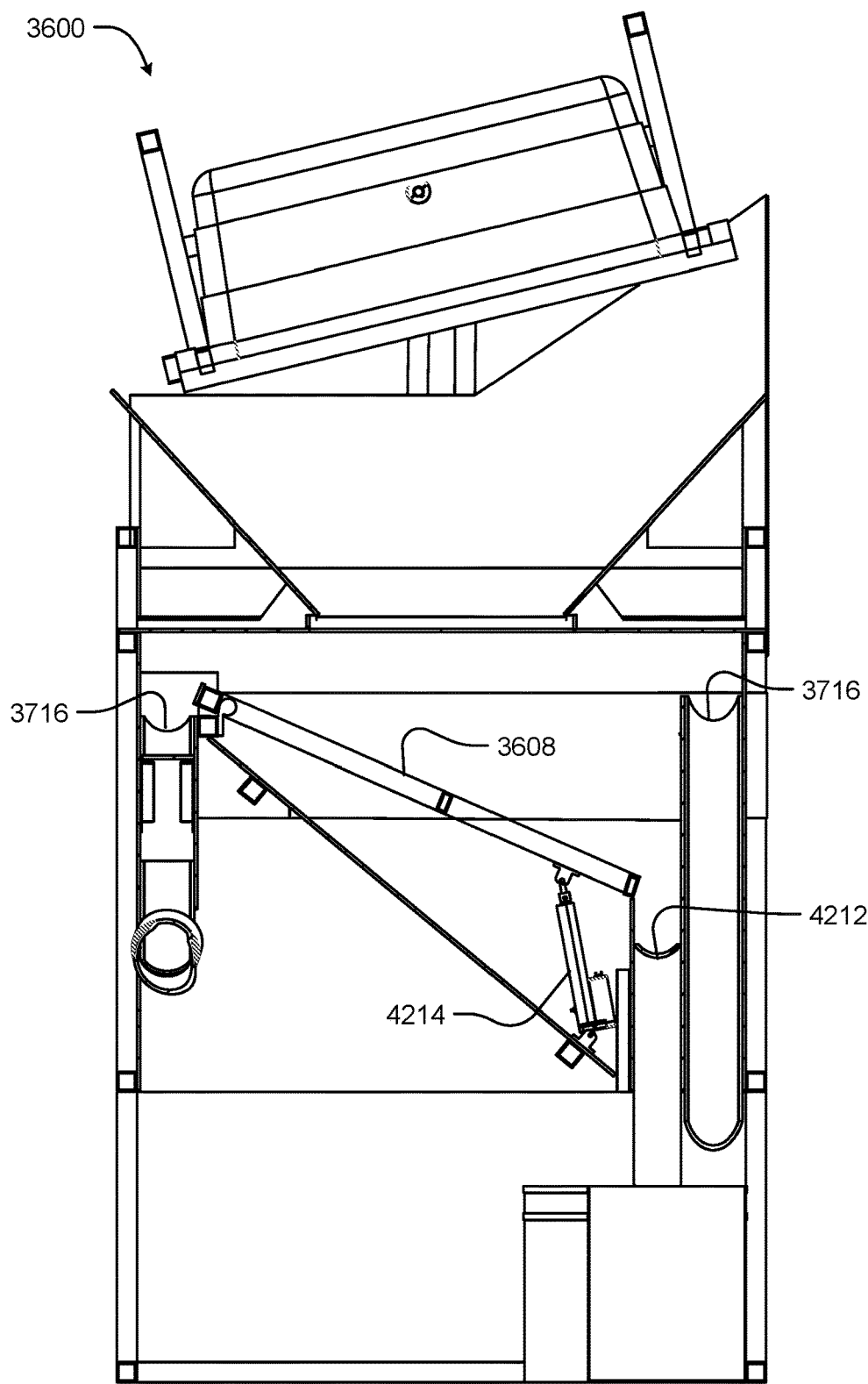
FIG. 43 illustrates a side view of the example of the harvester system of FIG. 37 for use in the waste separation area of FIG. 1 according to some implementations.

FIG. 43 illustrates a side view of the example system 3600 of FIG. 36 for use in the waste separation area 126 of FIG. 1 according to some implementations. In the current example, the live insects have been collected within a bin by the shoots 3716 as discussed above with respect to FIG. 42. The remaining dead insects retained on the screen 3608 may then be collected as the height controlling unit 4214 may depress, as shown, one end of the screen 3608 to align with the dead insect collection shoot 4212. In this manner, gravity may move the dead insects as well as any other content on top of the screen 3608 into the dead insect collection shoot 4212 and the contents may be further processed to obtain minerals or materials from the dead insects, such as chitin or chitosan.

Figure 44:
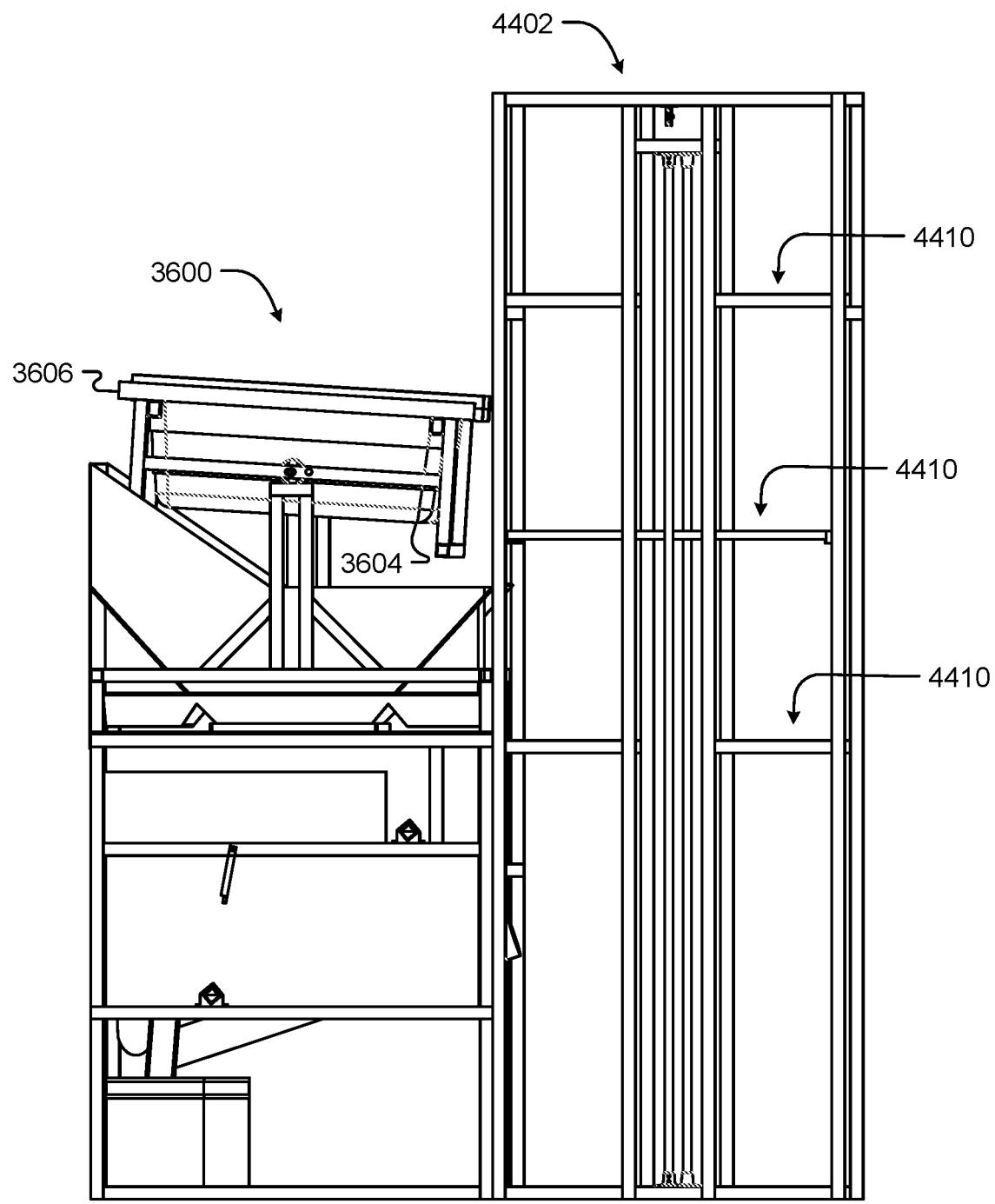
FIG. 44 illustrates a side view of the example of the harvester system of FIG. 36 being loaded by an example elevator according to some implementations.

FIG. 44 illustrates a side view of the example of the harvester system 3600 of FIG. 36 being loaded by an example elevator 4402 according to some implementations. In some cases, a habitat flipping device 3606 of the harvesting system 3600 may be positioned at a height well above ground level. In these cases, the harvester system 3600 may be positioned next to or adjacent to an elevator 4402 that may raise the habitats 3604 up and place them within the habitat flipping device 3606. For example, the elevator 4402 may include one or more lift platforms 4410 to raise each habitat 3604 to the height of the habitat flipping device 3606 and to push the habitat 3604 into the habitat flipping device 3606. In some cases, the elevator 4402 or lift platform 4410 may be configured to remove the habitat 3604 from the habitat flipping device 3606 after the contents are deposited into the harvesting system 3600.

Figure 45:
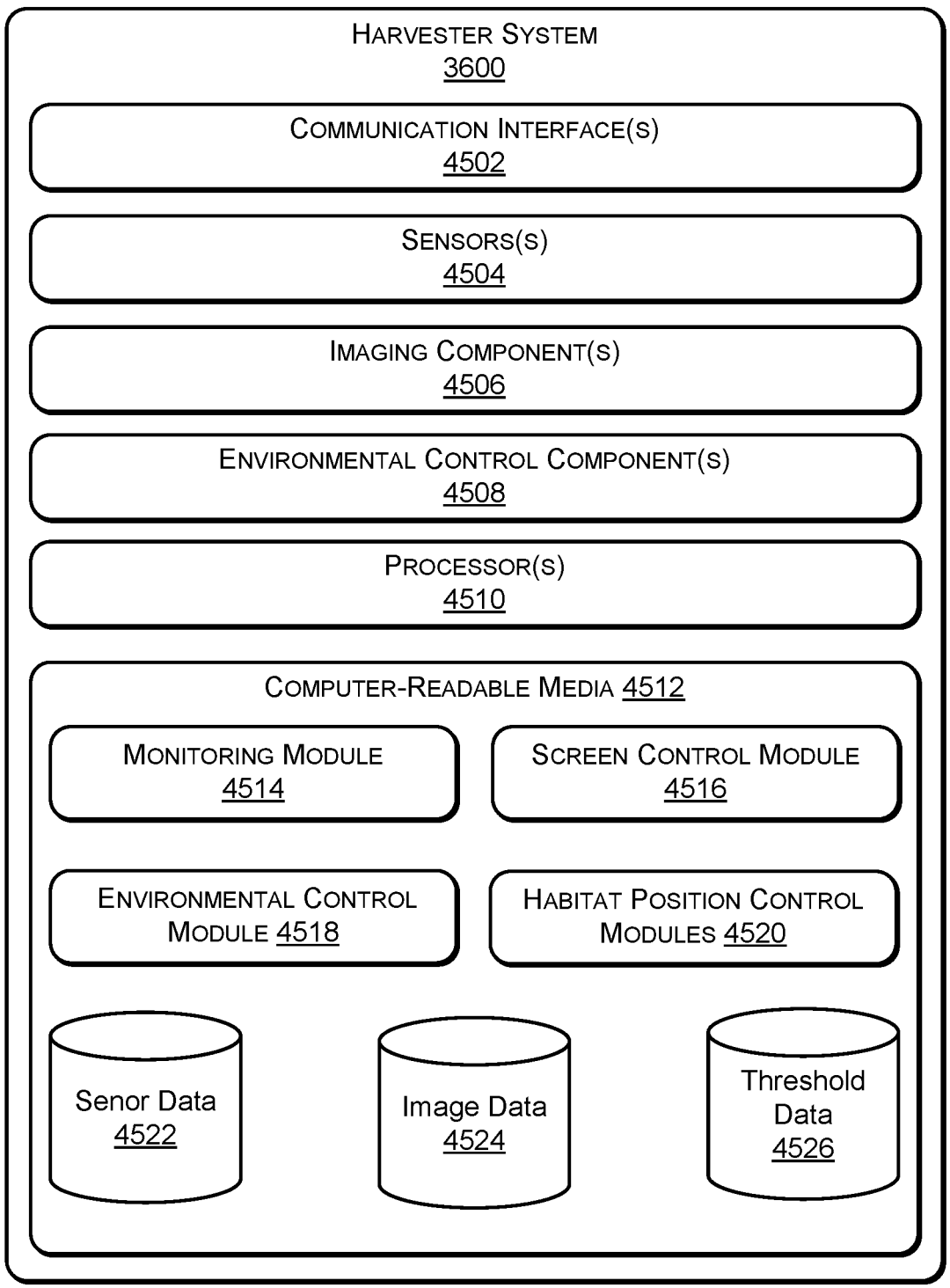
FIG. 45 illustrates example components of the harvesting system of FIG. 36 according to some implementations.

FIG. 45 illustrates example components of the harvesting system 3600 of FIG. 36 according to some implementations. As described above, the harvesting system 3600 may be a self-contained unit for harvesting insects. In some cases, the harvesting system 3600 may be configured to monitor the progress of insects on the screen to ensure that the live insects are migrated over a shoot prior to lowering the screen to collect the remaining dead insects.

In the illustrated example, the harvesting system 3600 includes one or more communication interfaces 4502. The communication interfaces 4502 may be configured to facilitate communication between one or more networks and/or other devices of the cultivation system described herein. For instance, the communication interfaces 4502 may provide a notification to an elevator or habitat transportation system indicating that the harvester system 4500 has completed processing a particular habitat and the habitat flipping device is ready for the delivery of an additional habitat. In some cases, the communication interfaces 4502 may also facilitate communication between one or more wireless access points, a master device, and/or one or more other computing devices as part of an ad-hoc or home network system. The communication interfaces 45 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 4502 may also enable device to device communication such as between harvesting system 3600 and one or more printers and/or one or more other electronic devices in proximity to the harvesting system 3600 to provide information to a system operator or manager.

The harvesting system 3600 may also include various sensors 4504 that may collect sensor data that is usable to determine an amount or percentage of live insects still remaining on the screen. For example, the harvesting system 4500 may include an optical sensor or motion sensor capable to determining whether or not live insects are still active upon the screen. In some instances, the harvesting system 4500 may include also light, optical, or photo sensors, mechanical sensors (e.g., pressure, force, or motion sensors), electrical sensors (capacitive, resistive, current, or potential based sensors), weight sensors, thermal or heat sensors, among others. For example, the thermal sensors may be able to determine if any and an amount of living matter (e.g., live insects) remains on the screen.

In some cases, a plurality of imaging component 4506 may be used to monitor the insects within the harvesting system 4500. For example, the harvesting system 4500 may include a three-dimensional camera, an infrared camera, and/or a red-green-blue camera. In one example, the three-dimensional and infrared camera may be configured to capture information related to depths, location, and movement of objects within the field of view. The red-green-blue camera may be configured to detect edges of objects by identifying changes in color within the field of view. In some cases, the harvesting system 4500 may also include additional imaging components for tracking and determining movement of insects within the harvesting system 4500.

The harvesting system 4500 may also include one or more environmental control components 4508. The environmental control components 4508 may be utilized to control environmental factors, such as wind, temperatures, humidity, salinity, noise, scents, mechanical vibrations, etc. within the harvesting system 4500 to encourage migration of the live insects onto the shoots.

The harvesting system 4500 includes one or more processors 4510, such as at least one or more access components, control logic circuits, central processing units, or processors, as well as one or more computer-readable media 4512 to perform the function of the harvesting system 4500. Additionally, each of the processors 4510 may itself comprise one or more processors or processing cores.

Depending on the configuration, the computer-readable media 4512 may be an example of tangible non-transitory computer storage media and may include volatile and nonvolatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 4510.

Several modules such as instruction, data stores, and so forth may be stored within the computer-readable media 4512 and configured to execute on the processors 4510. For example, as illustrated, the computer-readable media 4512 stores a monitoring module 4514, a screen control module 4516, an environmental module 4518, and a habitat position control module 4520. The computer-readable media 4512 may also be configured to store data, such as sensor data 4522 collected by the sensors 4504, image data 4524 captured by the camera components 4506, and threshold data 4526 such as maximum amount (e.g., weight) or number of live insects that may be discarded per habitat.

The monitoring module 4514 may be configured to analyze the sensor data 4522 and the image data 4524 and to determine insect activity level, amount or number of insects, remaining weight on the screen, among other factors associated with the contents of a habitat deposited onto the screen. For example, the monitoring module 4518 may be configured to determine when the activity or movement of the live insects on the screen has fallen below a desired threshold 4526 and to cause the height controlling unit to lower the screen to remove the remaining contents (e.g., the dead insects).

The screen control module 4516 may be configured to cause the height controlling unit to raise and lower the screen based on the indications provided by the monitoring module 4518. In some cases, the screen control module 4516 may be configured to cause the height controlling unit to raise and lower the screen, in response to the expiration of a threshold 4526 amount of time. For example, the bin flipping device may cause a timer to initiate in response to the bin flipping device depositing the contents of a habitat onto the screen. The screen control module 4516 may then lower the screen following the expiration of a first threshold and then raise the screen falling the expiration of a second threshold. In some cases, the bin flipping device may be tied to the second threshold, such that the habitat position control module 4520 causes the bin flipping device to rotate a second habitat at a period of time associated with the second threshold (such as five seconds following the expiration of the second threshold or at a third threshold that expires five seconds after the second threshold).

The environmental module 4518 may control various environmental control components 4508 to cause or encourage the live insects to migrate onto the shoots for collection. For example, the environmental module 4518 may cause particular areas, such as the shoot, to have a temperature differential from the screen to encourage the live insects to move into the shoot.

The habitat position control module 4520 may be configured to cause the height controlling unit to raise and/or lower the screen. For example, as discussed above the habitat position control module 4520 may control the position of the screen based at least in part on input form the monitoring module 4514, such as in response to determining the amount of live matter on the screen has fallen below a threshold 4526. Alternatively, the habitat position control module 4520 may cause the habitat position control module 4520 to raise or lower the screen based on a period of elapsed time.

In some examples described above, a system for collecting newly born insects from an egg-bearing medium. In some cases, the system may include a platform having a plurality of holes, each hole sized to pass the medium and to retain eggs and a funnel connected to the platform to receive the medium as the medium passes through the holes. In other example described above, a system for collecting newly born insects from an egg-bearing medium ma include a platform having an area for receiving egg-bearing medium a second area for collecting the newly born insects. In some instances, the second area of the platform may include a funnel for collecting the newly born insects.

In some implementations, a system is described above including a platform having an area for receiving egg-bearing medium a second area for collecting newly born insects. A funnel ay be located within the second area of the platform and an air source may be associated with the platform to apply an air-flow over the first area and the second area, the air source posited with respect to the platform opposite the second area and the air-flow to move the newly born insects from the first area into the second area.

In other examples, a system may include a robotic arm having a coupling device to secure to a habitat insert within a habitat. In some cases, a conveyor may be configured to position a habitat in an area associated with a robotic arm, such that the robotic arm may couple to the habitat insert, remove the habitat insert from the habitat, position the habitat insert over a collection bin, and vibrate the habitat insert to deposit an insect within the collection bin. In other examples, the conveyor may be configured to position a habitat for harvesting, such that a vacuum device may apply suction to the habitat at a predetermined air flow wattage, the flow wattage based at least in part on a percentage of the habitat to experience the suction. In some cases, a collection tube may receive the collected insects and transport insects from the habitat to a collection area.

In one example, a device including a platform having a plurality of holes, each hole sized to pass insect waste product and to retain insects is discussed above. In one instance, a funnel positioned adjacent to the platform has an angle to cause insects to migrate down the funnel towards a collection area. The platform may also have an area for receiving contents of a habitat and a second area for collecting insects. In some cases, the device may include an environmental stimulus device associated with the platform to apply an environmental stimulus to cause the insects to migrate towards the second area.

In one implementation, a system may include a platform having a first area for receiving contents of a habitat, the contents including insects and insect waste product, the first area having holes sized to pass the insect waste product and retain the insects. In some cases low friction surface having a first edge adjacent to the first area and a second edge adjacent to a collection area, the low friction surface having a coefficient of friction and angle to cause insects to move away from the first area toward the collection area.

In one implementation, a device may include a tube for receiving contents of a habitat and a basin area having an inner section that is configured to spin at a first predetermined velocity, the first predetermined velocity selected to cause limbs, heads, and abdomens of insects to separate, the inner section including corrugated exterior portion having holes sized to allow the limbs of the insects to pass and retain the heads and abdomens. In one example, the device may include a powdering section to receive the heads and limbs, the powdering section having a powdering device and configured to spin at a second velocity, the second velocity selected to convert the abdomens into a powder in response to the abdomens contacting the powdering device but maintain the heads in substantially whole form and a corrugated bottom section having holes sized to allow the powder to pass and retain the heads.

In one example, a platform is discussed including a first section configured to vibrate at a first frequency to cause limbs of insects to move in a desired direction at a first pace, heads of insects to move in the desired direction at a second pace, and abdomens of insects to move in the desired direction at a third pace, the first pace different from the second pace and the third pace and the second pace different from the third pace. In one case, a second section configured to vibrate at a first frequency to cause limbs of insects to move in a desired direction at a fourth pace, heads of insects to move in the desired direction at a fifth pace, and abdomens of insects to move in the desired direction at a sixth pace, the fourth pace different from the fifth pace and the sixth pace and the fifth pace different from the sixth pace.

In some instances, a system may include a slicing apparatus to separate the limbs, heads, and abdomen of the insects. For instance, a conveyor to receive insects for processing to move the insects into the slicing apparatus and an impact wall to arrange the insects in a desired orientation prior to the insects reaching the slicing apparatus, the insects to impact the impact wall as the insects are moved by the conveyor.

In one implementation, a system including an incubation area having a rack housing an incubation enclosure is discussed. The system may also include a cultivating area including a rack housing a first insect habitat and an insect collection area for receiving an incubation enclosure. The insect collection area may include an egg collecting device, the egg or newly born insect collecting device to separate the eggs from an incubation medium. In some cases, an egg counting device may be configured to allocated a predetermined number of eggs to an empty insect habitat. The system may also include a waste separation area for receiving the first habitat and including a waste separation device for separating waste product of the first habitat from live insects of the first habitat and a processing area for receiving the live insects and including a processing device to separate the limbs, heads, and abdomens of the insects.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A system for harvesting insects comprising:
   a habitat for insects; and
   a harvesting system, the harvesting system comprising:
      a bin flipping device for receiving the habitat, the bin flipping device configured to secure to the habitat and to rotate the habitat by at least 120 degrees, the habitat having contents including waste, live insects, and dead insects;
      a screen having perforations sized to allow waste material to pass but to retain the live insects on a top surface of the screen;
      a shield to prevent contents of the habitat from escaping the system as the bin flipping device rotates the habitat and to direct the contents onto the screen;
      a first shoot positioned adjacent to at least one edge of the screen, the first shoot formed form a material having a coefficient of friction select to allow the live insect and at a first angle to direct the live insects into a first collection bin;
      a second shoot positioned below the first shoot, the second shoot at a second angle to direct the dead insects into a second collection bin; and
      a height adjusting device coupled to the screen, the height adjusting device configured to automatically lower the screen from a first position to a second position adjacent to the second shoot after the expiration of a predefined period of time, and wherein when the screen is in the second position, the screen is at a third angle to allow gravity to move the dead insects on the screen into the second shoot.

2. The system as recited in claim 1, further comprising:
a third shoot positioned adjacent to the edge of the screen when the screen is in the first position, the third shoot configured at a fourth angle to direct the live insets into the live insect collection bin.

3. The system as recited in claim 1, further comprising:
a third shoot positioned below the screen, the third shoot configured at a fourth angle to direct the waste into a waste collection bin.

4. The system as recited in claim 1, further comprising:
an environmental stimulus device associated with the screen, the environmental stimulus device configured to apply an environmental stimulus to the live insects when the screen is in the first position to encourage the live insects to migrate over the first shoot.

5. The system as recited in claim 4, wherein the environmental stimulus is at least one of:
a vibration; a sound;
a scent;
mechanical stimulus; or
air flow.

6. The system as recited in claim 1, wherein the bin flipping device is configured to rotate the habitat by 180 degrees.

7. The system as recited in claim 1, further comprising an elevator for lifting the habitat from a first level off the ground to a second level higher than the first level, the second level adjacent to the bin flipping device.

8. A system for harvesting insects comprising:
a screen having perforations sized to allow waste material to pass but to retain live insects on a top surface of the screen;
a first shoot positioned adjacent to at least one edge of the screen, the first shoot configured to direct the live insects into a first collection bin;
an environmental stimulus device associated with the screen, the environmental stimulus device configured to apply an environmental stimulus to the live insects to encourage the live insects to migrate over the first shoot, wherein the environmental stimulus includes the environmental stimulus device causing the screen to vibrate;
a second shoot positioned below the first shoot, the second shoot configured to direct dead insects retained on the screen into a second collection bin; and
a height adjusting device coupled to the screen, the height adjusting device configured to automatically lower the screen from a first position to a second position adjacent to the second shoot after the expiration of a predefined period of time, and wherein when the screen is in the second position, the screen is at a third angle to allow gravity to move the dead insects on the screen into the second shoot.

9. The system as recited in claim 8, further comprising a bin flipping device for receiving a habitat, the bin flipping device configured to secure to the habitat and to rotate the habitat by at least 180 degrees, the habitat having contents including waste, live insects, and dead insects.

10. The system as recited in claim 8, further comprising a shield to prevent contents of the habitat from escaping the system as the bin flipping device rotates the habitat and to direct the contents onto the screen.

11. The system as recited in claim 8, further comprising an elevator positioned adjacent to the system, the elevator configured to lift the habitat to a level adjacent to the bin flipping device.

12. The system as recited in claim 8, further comprising:
a third shoot positioned adjacent to the edge of the screen when the screen is in the first position, the third shoot configured at a fourth angle to direct the live insets into the live insect collection bin.

13. A system for harvesting insects comprising:
a screen having perforations sized to allow waste material to pass but to retain live insects and dead insects on a top surface of the screen;
a bin flipping device configured to rotate to deposit the waste, the live insects, and the dead insects onto the screen;
a shield to direct the waste, the live insects, and the dead insects onto the screen and to prevent the live insects from escaping the system as the bin flipping device rotates;
a first shoot positioned adjacent to at least one edge of the screen, the first shoot formed form a material having a coefficient of friction select to allow the live insect and at a first angle to direct the live insects into a first collection bin;
a second shoot positioned below the first shoot, the second shoot at a second angle to direct the dead insects into a second collection bin; and
a height adjusting device coupled to the screen, the height adjusting device configured to automatically lower the screen from a first position to a second position adjacent to the second shoot after the expiration of a predefined period of time, and wherein when the screen is in the second position, the screen is at a third angle to allow gravity to move the dead insects on the screen into the second shoot.

14. The system as recited in claim 13, further comprising:
a third shoot positioned adjacent to the edge of the screen when the screen is in the first position, the third shoot configured at a fourth angle to direct the live insets into the live insect collection bin.

15. The system as recited in claim 13, further comprising:
a third shoot positioned below the screen, the third shoot configured at a fourth angle to direct the waste into a waste collection bin.

16. The system as recited in claim 13, further comprising:
an environmental stimulus device associated with the screen, the environmental stimulus device configured to cause the screen to vibrate when the screen is in the first position to encourage the live insects to migrate over the first shoot.

17. The system as recited in claim 13, further comprising:
an environmental stimulus device associated with the screen, the environmental stimulus device configured to apply an environmental stimulus to the live insects when the screen is in the first position to encourage the live insects to migrate over the first shoot.

18. The system as recited in claim 17, wherein the environmental stimulus is at least one of:
a sound;
a scent;
mechanical stimulus; or
air flow.

19. The system as recited in claim 13, wherein the bin flipping device is configured to rotate the habitat by 180 degrees.

20. The system as recited in claim 13, further comprising:
a habitat containing the waste, the live insects, and the dead insects; and
an elevator for lifting the habitat from a ground level and to cause the habitat to engage with the bin flipping device.

* * * * *